US008580928B2

(12) United States Patent  
Dennis

(10) Patent No.: US 8,580,928 B2  
(45) Date of Patent: Nov. 12, 2013

(54) CDR-REPAIRED ANTIBODIES

(75) Inventor: Mark S. Dennis, San Carlos, CA (US)

(73) Assignee: Genetech, Inc., South San Francisco, CA (US)

( * ) Notice: Subject to any disclaimer, the term of this patent is extended or adjusted under 35 U.S.C. 154(b) by 0 days.

(21) Appl. No.: 12/947,714

(22) Filed: Nov. 16, 2010

(65) Prior Publication Data

US 2011/0237779 A1 Sep. 29, 2011

Related U.S. Application Data

(63) Continuation of application No. 11/061,841, filed on Feb. 18, 2005, now abandoned.

(60) Provisional application No. 60/545,840, filed on Feb. 19, 2004.

(51) Int. Cl.
*C07K 16/00* (2006.01)
*C12P 21/00* (2006.01)
*C40B 30/04* (2006.01)
*C40B 50/06* (2006.01)

(52) U.S. Cl.
USPC ............ 530/387.3; 435/69.6; 506/26; 506/9; 536/23.53

(58) Field of Classification Search
USPC ..................... 530/387.3; 435/69.6; 506/26, 9; 536/23.53
See application file for complete search history.

(56) References Cited

U.S. PATENT DOCUMENTS

| | | | |
|---|---|---|---|
| 5,530,101 A | 6/1996 | Queen et al. |
| 5,824,307 A | 10/1998 | Johnson |
| 6,107,059 A | 8/2000 | Hart |
| 6,407,213 B1 | 6/2002 | Carter et al. |
| 6,849,425 B1 | 2/2005 | Huse et al. |
| 7,175,996 B1 | 2/2007 | Watkins et al. |
| 2003/0045691 A1 | 3/2003 | Ono et al. |
| 2003/0228663 A1 | 12/2003 | Lowman et al. |
| 2004/0162413 A1 | 8/2004 | Watkins et al. |
| 2005/0064438 A1 | 3/2005 | Huse et al. |

FOREIGN PATENT DOCUMENTS

| | | | |
|---|---|---|---|
| WO | 92/22653 | | 12/1992 |
| WO | WO 95/07301 | | 3/1995 |
| WO | 98/45332 | | 10/1998 |
| WO | WO 98/45331 | | 10/1998 |
| WO | WO 01/55217 A1 | | 8/2001 |
| WO | WO 03/046204 A2 | | 6/2003 |
| WO | WO 03/087131 A2 | | 10/2003 |
| WO | WO 03/105782 A2 | | 12/2003 |
| WO | WO 2004/003019 | * | 1/2004 |
| WO | WO 2004/003155 A2 | | 1/2004 |
| WO | WO 2005/062967 | | 7/2005 |
| WO | WO 2007/024921 | | 3/2007 |

OTHER PUBLICATIONS

Soderlind et al (Gene 160:269-72, 1995).*
MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994.*
Baca, M. et al., "A superactive insulin: [B10—Aspartic acid] insulin (human)" *Proc. Natl. Acad. Sci. USA* 94:10063-10064 (1997).
Balint and Larrick, "Antibody engineering by parsimonious mutagenesis" *Gene* 137(1):109-118 (Dec. 27, 1993).
Barbas et al., "In Vitro Evolution of a Neutralizing Human Antibody to Human Immunodeficiency Virus Type 1 to Enhance Affinity and Broaden Strain Cross-Reactivity" *Proc Natl Acad Sci U S A.* 91(9):3809-3813 (Apr. 1994).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" *Journal of Cell Biology* 111:2129-2138 (Nov. 1990).
Carter et al., "Humanization of an Anti-p185$^{HER2}$ Antibody For Human Cancer Therapy" *Proc Natl Acad Sci U S A.* 89(10):4285-4289 (May 1992).
Chothia, C. et al., "Conformations of immunoglobulin hypervariable regions" *Nature* 342(21):877-883 (Dec. 28, 1989).
Co et al., "Humanized antibodies for antiviral therapy" *Proc. Natl. Acad. Sci. USA* 88:2869-2873 (Apr. 1991).
Extended European Search Report mailed on Jun. 24, 2010 in European Application 09179091.5.
Foote et al., "Antibody Framework Residues Affecting the Conformation of the Hypervariable Loops" *J. Mol. Biol.* 224:487-499 (1992).
Gallop et al., "Applications of Combinatorial Technologies to Drug Discovery Background and peptide combinatorial libraries" *Journal of Medicinal Chemistry* 37(9):1233-1251 (Apr. 29, 1994).
Gallop, et al., "Applications of Combinatorial Technologies to Drug Discovery, 1. Background and Peptide Combinatorial Libraries" *Journal of Medicinal Chemistry* 37(9):1233-1251 (Apr. 29, 1994).
Hogrefe et al., "Creating randomized amino acid libraries with the QuikChange Multi Site-Directed Mutagenesis Kit" *Biotechniques* 33(5):1158-1160 (Nov. 2002).
Jones et al., "Replacing the Complementarity-Determining Regions in a Human Antibody with Those From a Mouse" *Nature* 321(6069):522-525 (May 29, 1986).

(Continued)

*Primary Examiner* — Lynn Bristol
(74) *Attorney, Agent, or Firm* — Jennifer L. Davis

(57) ABSTRACT

The present application concerns restoring antigen binding during humanization of antibodies through the selection of repaired hypervariable regions rather than through framework changes.

8 Claims, 14 Drawing Sheets

(56) References Cited

OTHER PUBLICATIONS

Kabat *Sequences of Proteins of Immunological Interest* (pp. 2275-2276), 5th edition 1 (1991).

Kettleborough et al., "Humanization of a Mouse Monoclonal Antibody by CDR-grafting: the Importance of Framework Residues on Loop Conformation" *Protein Engineering* 4(7):773-783 (1991).

Klobeck, et al., "Subgroup IV of human immunoglobulin K light chains is encoded by a single germline gene." *Nucleic Acids Research* 13(18):6515-6529 (1985).

Kunkel, et al., "Rapid and Efficient Site-Specific Mutagenesis without Phenotypic Selection" *Methods in Enzymology* 154:367-382 (1987).

Lazar et al., "Transforming Growth Factor α: Mutation of Aspartic Acid 47 and Leucine 48 Results in Different Biological Activities" *Molecular & Cellular Biology* 8(3):1247-1252 (Mar. 1988).

Lechner et al., "Characterization of Strand Displacement Synthesis Catalyzed by Bacteriophage T7 DNA Polymerase" *The Journal of Biological Chemistry* 258(18):11174-11184 (Sep. 25, 1983).

Lin et al., "Structure Function Relationships in Glucagon: Properties of Highly Purified Des-His$^1$-, Monoido-, and [Des-Asn$^{28}$, Thr$^{29}$] (homoserine lactone$^{27}$)-glucagon" *Biochemistry* 14(8):1559-1563 (1975).

Press, et al., "The Amino Acid Sequences of the Fd Fragments of Two Human γ 1 Heavy Chains" *Biochemical Journal* 117:641-660 (1970).

Presta et al., "Generation of a Humanized, High Affinity Anti-Tissue Factor Antibody for Use as a Novel Antithrombotic Therapeutic" *Thrombosis and Haemostasis* 85(3):379-389 (Mar. 2001).

Presta et al., "Humanization of an Antibody Directed Against IgE" *J Immunol.* 151(5):2623-2632 (Sep. 1, 1993).

Riechmann et al., "Reshaping human antibodies for therapy" *Nature* 332(6162):323-327 (Mar. 24, 1988).

Routledge et al., "A Humanized Monovalent CD3 Antibody which Can Activate Homologous Complement" *European Journal of Immunology* 21:2717-2725 (1991).

Rudikoff et al., "Single amino acid substitution altering antigen-binding specificity" *Proc. Natl. Acad. Sci. USA* 79:1979-1983 (Mar. 1982).

Schwartz et al., "A superactive insulin: [B10—Aspartic acid]insulin(human)" *Proc. Natl. Acad. Sci. USA* 84:6408-6411 (Sep. 1987).

Shearman et al., "Construction, Expression and Characterization of Humanized Antibodies Directed Against the Human α/β T Cell Receptor" *J. Immunol.* 147(12):4366-4373 (Dec. 15, 1991).

Sidhu et al., "Phage Display for Selection of Novel Binding Peptides" *Methods Enzymology* 328:333-363 (2000).

Tan, et al., "'Superhumanized' Antibodies: Reduction of Immunogenic Potential by Complementarity-Determining Region Grafting with Human Germline Sequences: Application to an Anti-CD28 *Journal of Immunology* 169:1119-1125 (2002).

Tempest et al., "Reshaping a Human Monoclonal Antibody to Inhibit Human Respiratory Syncytial Virus Infection In Vivo" *Bio/Technology* 9:266-271 (Mar. 1991).

Tomlinson, et al., "The Repertoire of Human Germline $V_H$ Sequences Reveals about Fifty Groups of $V_H$ Segments with Different Hypervariable Loops" *J. Mol. Biol.* 227:776-798 (1992).

Vasserot, et al., "Optimization of protein therapeutics by directed evolution" *Drug Discovery Today* 8(3):118-126 (Feb. 2003).

Werther et al., "Humanization of an Anti-Lymphocyte Function-Associated Antigen (LFA)-1 Monoclonal Antibody and Reengineering of the Humanized Antibody for Binding to Rhesus LFA-1" *J. of Immunology* 157:4986-4995 (1996).

Wu et al., "Humanization of a Murine Monoclonal Antibody by Simultaneous Optimization of Framework and CDR Residues" *J. Mol. Biol.* 294:151-162 (1999).

Wu, et al., "Stepwise in vitro affinity maturation of Vitzxin, an $\alpha_v\beta_3$-specific humanized mAb" *Proc. Natl. Acad. Sci, USA* 95:6037-6042 (May 1998).

Wu, H., "Simultaneous humanization and affinity optimization of monoclonal antibodies" *Methods in Molecular Biology* 207:197-212 (2003).

Yang et al., "CDR walking mutagenesis for the affinity maturation of a potent human anti-HIV-1 antibody into the picomolar range" *Journal of Molecular Biology* 254(3):392-403 (Dec. 1, 1995).

Boder et al., "Directed evolution of antibody fragments with monovalent femtomolar antigen-binding affinity" P Natl Acad Sci USA 97:10701-10705 (2000).

Janeway et al. Immunobiol Third edition,Garland Publishing Inc., (1997).

Rosok et al., "A combinatorial library strategy for the rapid humanization of anticarcinoma BR96 Fab" J Biol Chem 271(37):22611-22618 (Sep. 13, 1996).

Glaser et al., "Antibody engineering by codon-based mutagenesis in a filamentous phage vector system" J Immunol 149:3903-3013 (Dec. 15, 1992).

Huse et al., "Increased antibody affinity and specificity by codon-based mutagenesis" Intern Rev Immunol 10:129-137 (1993).

\* cited by examiner

VL Domain

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | CDR-L1 | | | | | | | | | |
| huKI | D | I | Q | M | T | Q | S | P | S | S | L | S | A | S | V | G | D | R | V | T | I | T | C | | | | | | | | | | | | | | | W | Y |
| MHM24 | D | V | Q | L | T | Q | S | P | S | Y | L | A | A | S | P | G | E | T | I | S | I | N | C | R | A | S | K | | | | | T | I | S | K | Y | L | A | W | Y |
| Mae11 | D | I | V | L | T | Q | S | P | A | S | L | A | V | S | L | G | Q | R | A | T | I | S | C | K | A | S | Q | S | V | D | Y | D | G | D | S | Y | M | N | W | Y |
| D3 | D | I | K | M | T | Q | S | P | S | S | M | S | A | S | L | G | E | S | V | T | I | T | C | K | A | S | R | | | | | D | I | K | S | Y | L | S | W | Y |

| | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | CDR-L2 | | | | | | | | | | | | | | | | | | | | | | | | | |
| huKI | Q | Q | K | P | G | K | A | P | K | L | L | I | Y | | | | | | | | G | V | P | S | R | F | S | G | S | G | S | G | T | D | F | T | L | T | I |
| MHM24 | Q | Q | E | K | P | G | K | T | N | K | L | L | I | Y | S | G | S | T | L | Q | S | G | I | P | S | R | F | S | G | S | G | S | G | T | D | F | T | L | T | I |
| Mae11 | Q | Q | K | P | G | Q | P | P | I | L | L | I | Y | A | A | S | Y | L | G | S | E | I | P | A | R | F | S | G | S | G | S | G | T | D | F | T | L | N | I |
| D3 | Q | Q | K | P | W | K | S | P | K | T | L | I | Y | Y | A | T | S | L | A | D | G | V | P | S | R | F | S | G | S | G | S | G | Q | D | Y | S | L | T | I |

| | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|
| | | | | | | | | | | | | | | CDR-L3 | | | | | | | | | | | | | | | | | | | |
| huKI | S | S | L | Q | P | E | D | F | A | T | Y | Y | C | | | | | | | | | | F | G | Q | G | T | K | V | E | I | K | R |
| MHM24 | S | S | L | E | P | E | D | F | A | M | Y | Y | C | Q | Q | H | N | E | Y | P | L | T | F | G | T | G | T | K | L | E | L | K | R |
| Mae11 | H | P | V | E | E | E | D | A | A | T | F | Y | C | Q | Q | S | H | E | D | P | Y | T | F | G | A | G | T | K | L | E | L | K | R |
| D3 | S | S | L | E | S | D | D | T | A | T | Y | Y | C | L | Q | H | G | E | S | P | F | T | F | G | S | G | T | K | L | E | L | K | R |

(SEQ ID NOS: 15-18)

FIG._1A

VH Domain

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 36 | 37 | 38 | 39 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | CDR-H1 | | | | | | | | | | |
| Acceptor | E | V | Q | L | V | E | S | G | G | G | L | V | Q | P | G | G | S | L | R | L | S | C | A | A | S | | | | | | | | | | W | | V | R | Q | |
| MHM24 | E | V | Q | L | Q | Q | P | G | A | E | L | M | R | P | G | A | S | V | K | L | S | C | K | A | S | G | Y | S | F | T | G | H | W | M | N | | W | V | R | Q |
| Mae11 | D | V | Q | L | Q | Q | P | G | P | G | L | V | K | P | S | Q | S | L | S | L | A | C | S | V | T | G | Y | S | I | T | S | G | Y | S | W | N | W | I | R | Q |
| D3 | E | V | Q | L | Q | Q | S | G | A | E | L | V | R | P | G | A | L | V | K | L | S | C | K | A | S | G | F | N | I | K | D | Y | Y | M | H | | W | V | K | Q |

| | 40 | 41 | 42 | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | CDR-H2 | | | | | | | | | | | | | | | | | | | | | | | | | | | | |
| Acceptor | A | P | G | K | G | L | E | W | V | | | | | | | | | | | | | | | | | | | R | F | T | I | S | A | D | T | S | K | N | T | A | Y |
| MHM24 | R | P | G | Q | G | L | E | W | I | G | M | I | H | P | S | D | S | E | T | R | L | N | Q | K | F | K | D | K | A | T | L | T | V | D | K | S | S | S | T | A | Y |
| Mae11 | P | P | G | N | K | L | E | W | M | G | S | I | T | | Y | D | G | S | S | N | Y | N | P | S | L | K | N | R | I | S | V | T | R | D | T | S | K | N | Q | F | F |
| D3 | R | P | E | Q | G | L | E | W | I | G | W | I | D | P | E | N | G | N | T | I | Y | D | P | K | F | Q | D | K | A | S | I | T | A | D | T | S | S | N | T | A | Y |

| | 80 | 81 | 82 | 82a | 82b | 82c | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | CDR-H3 | | | | | | | | | | | | | | | | | |
| Acceptor | L | Q | M | N | S | L | R | A | E | D | T | A | V | Y | Y | Y | C | | | | | | | | | | | | | W | G | Q | G | T | L | V | T | V | S | S | |
| MHM24 | M | Q | L | S | S | P | T | S | E | D | S | A | V | Y | Y | C | A | R | G | I | Y | F | Y | G | T | T | Y | F | D | Y | W | G | Q | G | T | T | L | T | V | S | S |
| Mae11 | L | K | L | N | S | A | T | A | E | D | T | A | T | Y | Y | C | A | R | G | S | H | Y | F | G | H | W | H | F | A | V | W | G | A | G | T | T | V | T | V | S | S |
| D3 | L | Q | L | S | S | L | T | S | E | D | T | A | V | Y | Y | C | A | R | D | T | A | A | Y | | | | | F | D | Y | W | G | Q | G | T | T | L | T | V | S | S |

(SEQ ID NOS: 19-22)

FIG._1B

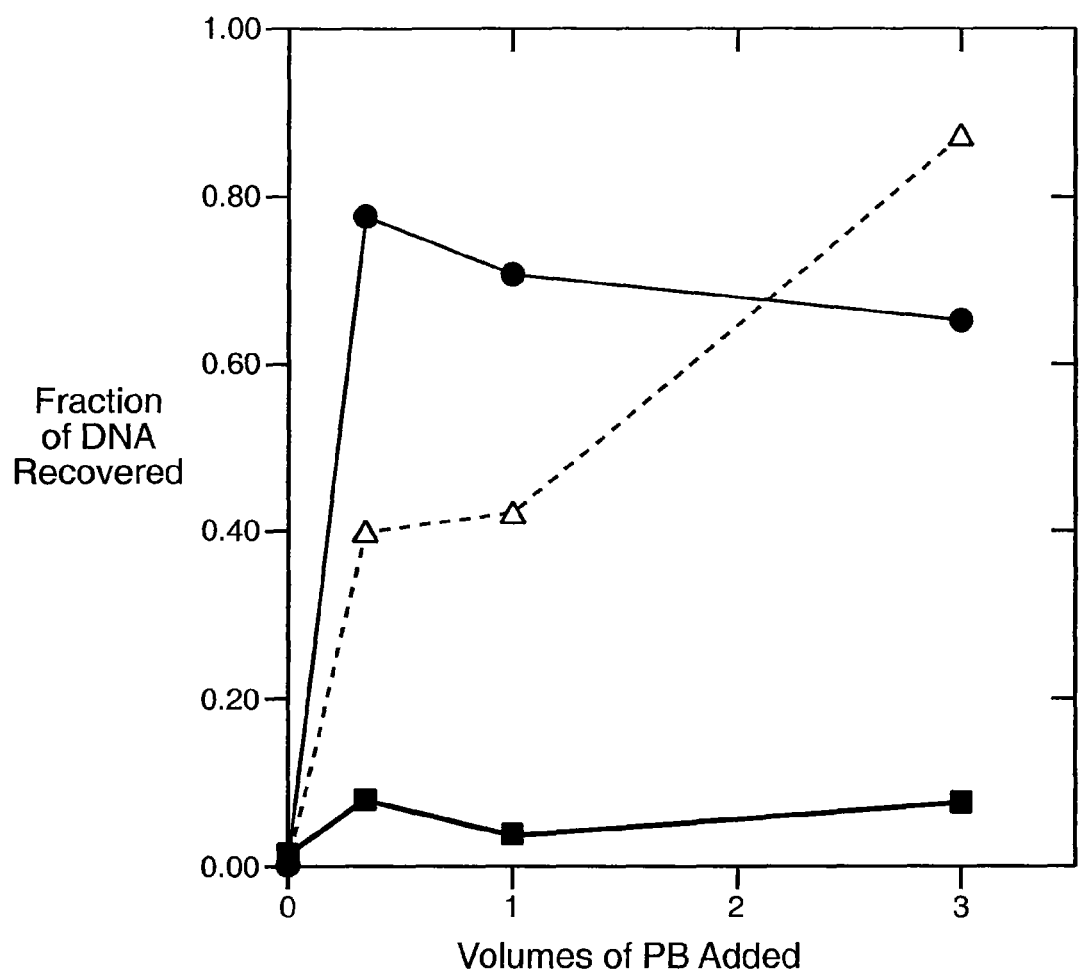
FIG._2

VL Domain of Initial D3 Library

| CDR-L1 | CDR-L2 | CDR-L3 |
|---|---|---|
| K A S R D I K S Y L S | Y A T S L A D | L Q H G E S P F T |
| K A L R Y N E R F L R | Y A S S Q A E | Q Q H G E Y Q S T |
| K A S R D I K S Y L S | Y A T S L A D | L Q H G E S P F T |
| K Q S C T D V Q S K E S | C A T R P A D | G Q Q H V E R P Y A |
| K A T D E H I K Q L S | Y A K C L D K | L Q H G E S S F H |
| K A A K A T I K K Y L S | T A T S L A D | L M H G E H S P F T |
| K A S R D I K S Y L S | Y A T S L A D | L Q H G E S P F T |
| K A S R D I K S Y L S | Y A T S L A D | L Q H G E S P F T |
| L W S L H H T Q I L G | Y A T S L V H | L Q H D E P Q L T |
| K A I R D T R Y L L S | Y A N X K S D | L N V G S P F T |
| K G S R Y N K R Y L R | Y A T S L A D | L Q H G E S P F T |
| I E T R V I S L L Q | E A S N L A G | L Q H G E S P F T |
| K G S R R I S F M S | S A S S P A V | L Q H G E S P F T |
| K A S R D I K S Y L S | Y A T S L A D | L Q H G E S P F T |
| I E S R A F Q K N L S | X G T S L S Y | L Q H G G R H L T |
| K A A G A S H M W H L S | Y P I T L V N | L Q H H G A G T F F T |
| K A S R D I K S Y L S | Y A T S L A D | L Q H G E S P F T |
| K G I V H M K S Y L S | Y A T S L A D | L Q H G E S P F T |
| K S N H S S K C Y L S | Y G S S L E N | P M H R K S P I S |
| T E G R H V K C Y L S | Y A T S L A D | L Q H G E S P F T |

(SEQ ID NOS: 46–65) (SEQ ID NOS: 66–85) (SEQ ID NOS: 86–105)

FIG._3A-1

VH Domain of Initial D3 Library

| CDR-H1 | CDR-H2 | CDR-H3 |
|---|---|---|
| G F N I K D Y Y M H | G W I D P E N G N T I Y D P K F Q D | R D T A A Y F D Y |
| G F N I K D Y Y M H | W W I D P E N G N T H Y D P K F Q D | R N T A A Y F D Y |
| G F N I K D Y Y M H | G W H D P E N G N T H Y D P K F Q D | R D T A A Y F D Y |
| G F N I K D Y Y M H | G W N I H P E N G N T H Y D P K F Q D | R D T A A Y F D Y |
| G F N I K D Y Y M L | G W H H D P E N G N T H Y D P K F Q D | R D T A A Y F V Y |
| C F N I R K S Y L L | G S N A P K Q G Y P S x D T K F x x | K S T L P N F V D Y |
| G F N I H S x G Y T P | S W I D D Q x N C D D P Y x D T K F L D | R D A A A Y Y x Y |
| G F N I H K D Y M M H | G W H D P V K G N K F T T F H L Y G Q D | K D T E A R F G E N |
| G F N H H K D x Y M N | G x I D P A x N G D T T A H N F L D N D | K H T E A R F D Y |
| G F N I H K D Y Y M H | S W M D A x N G K T N S Q Q Q D | R D T A A G F H A S |
| G F N I H K D x Y M H | G L I D P V K K Y R N S I R A Q D | R D A V A N Y Y C F |
| D L N I P N D Y Y K P | G W H D P K Y R N S I R A Q D | R E T A G F H A S |
| G F N I H K D Y Y M H | S W S V R E S G T H Y E T K H A Q D | R D S S A S S x V E D |
| G F S I T N D Y Y V L | G W H D P E N G N T H Y D P K F Q D | R D T A A Y F D Y |
| G F N I H V D Y Y M H | G W I D P E N G N T H Y D P K F Q D | R E T A S I V E Y |
| G F N I S H T Y Y M H | G W H D P E N G N T H Y D P K L H D | K D T A A Y F D Y |
| G F N I H K D Y Y M H | G W I D P E N G N T H Y D P K F Q D | R D T A A Y F D Y |
| G F N I H K D Y Y M H | G W I D P E N G N T H Y D P K F Q D | R D T A A Y F D Y |
| G F N I H K D Y Y M H | G W I D P E N G N T H Y D P K F Q D | R D T A A Y F D Y |
| G F N I H K D Y Y M H | G W I D P E N G N T H Y D P K F Q D | R D T A A Y F D Y |

(SEQ ID NOS: 106–125)   (SEQ ID NOS: 126–145)   (SEQ ID NOS: 146–165)

FIG._3A-2

VL Domain of Initial MHM24 Library

| CDR-L1 | CDR-L2 | CDR-L3 |
|---|---|---|
| R A S K T I S K Y L A | S G S T L Q S | Q Q H N E Y P L T |
| R A S N T M R K Y R A | S X R T L Q S | H X Q H N V S L V T |
| P A A S Y S I K T Y L R | S G S T L E S | X Q H N E Y P L T |
| R E G L R F S K D L A | S G S T L E S | Q Q H N E Y P L T |
| R A S R I M T K T I S | I G C M V P G | Q Q H K E F P Q T |
| T A C T T L R E X V P | S S C T L Q S | Q Q N V Y R L T |
| Y E T K T I T T Y V P | S G G H Q Q S | Q L Q X P T T |
| G S I K S R Q N L A | S A S T F Q T | Q X K I D X P T T |
| R X S T I W K X L T | C G S T P Q N | Y Q C N D Y Q A S |
| Y A S I T T H P A | S D R P L L S | X H C H E X A Q R |
| L A S Q P V S R T H G | S G S P L X S | L R Y T P Y P L T |
| R A S K T I S K Y L A | S G S T L E S | Q Q H N E E L L T |
| R A N K K I H I S R S | R A I R M H T | L Q K K E S E H |
| R A T N R N I S N N M L | S C W S P Q S | K R H N E X L L T |
| R T N R N I G K F P A | S G I T L K S | Q Q X S R Y P L A |
| R A S K T I S I Y R A | S G S T L E S | Q Q H N E Y P L T |
| G A S K T Q R M S T Y L A | S G S T L E S | H K H N E Y P L T |
| R A R R E A F T X H L A | S V D S Q E S | Q Q H N E Y P L T |
| L A R K T L S T D L A | S G S T L E S | P P T N E Y A L T |
| R A S K T I S K Y L A | S G S T L E S | Q Q H N E Y P L T |

(SEQ ID NOS: 166-186) (SEQ ID NOS: 187-207) (SEQ ID NOS: 208-228)

*FIG._3B-1*

VH Domain of Initial MHM24 Library

| CDR-H1 | CDR-H2 | CDR-H3 |
|---|---|---|
| G Y S F T G H W M N | G M I H P S D S E T R L N Q K F K D | R G I Y F Y G T T Y F D Y |
| G F G F M G L W G N | H H P S D S E T R L N Q K F K D | R G I Y F Y G T T Y F D Y |
| G Y S F T G H W M N | H H P S D S E T R L N Q K F K D | R G I Y F Y G T T Y F D Y |
| G C D F N G P W L N | H H P S D S E T R L N Q K F K D | R G I Y F Y G T T V G Y |
| G Y S F T G H W M N | H H P S D S E T R L N Q K F K D | R G F H L Y G T T Y F D Y |
| G Y T Y T S H X M N | H H P S D S E T R L N Q K F K V | R G F I Y Y G R T L I D Y |
| G Y S F T G H W M N | H L S D T E S R L N H K F M E | R G I H H Y G T T Y F D Y |
| G Y I S T G P W M D | H R V S X S G K N Q K F M E | R G I Y F Y G T T Y F D H |
| V E A L H R S L D E | F T L R V S X S G K N Q K F M E | R G N D L Y C T T X F D H |
| G Y G Y T R T G K S | D P P E R X L F P S E S V I Q R | R G I H H Y G T T Y F D Y |
| D D C L S G H W T N | H Q P S Y V T R L K P G F Q D | R G I Y F Y G T T Y F D Y |
| G Y S F T G H W M N | H H P S D S E T R L N Q K F K D | R G I Y F Y G T T Y F D N |
| G F T F P L H W M N | S L P I E K P V W T I N F X N | R G I Y F Y G T T Y F D Y |
| T S S S L P I E K ? | H P S D S E R L K Q N I H F K E | R G I Y F Y G T T Y F N C |
| G Y S F T G H W M N | H H P S D S E T R M N N T F K E | K G R Y D N S P T Y C D Y |
| S M I L R S A S D T | R M N N T F K E | |
| G Y S F T G H W M N | H H P S D S E T R L N Q K F K D | R G I Y F Y G T T Y F D Y |

(SEQ ID NOS: 229-245)   (SEQ ID NOS: 246-262)   (SEQ ID NOS: 263-278)

FIG._3B-2

VL Domain of Initial Mae11 Library

| CDR-L1 | CDR-L2 | CDR-L3 |
|---|---|---|
| K A S Q S V D Y D G D S Y M N | A A S Y L G S | Q Q S H E D P Y T |
| K A S R R V D F Y N I S Y R K | A A S Y L G S | Q Q S H E D P Y T |
| P A S H N V I D G F I Y L Y | A V L Y L V S | D Q Q S H Q V Y P Y T |
| K A S Q S V D Y D G D S Y M N | S A R H L G T | Q Q S H E E A Y T |
| K A A Q S V D D D G D S Y M N | A A S Y L G S | Q Q S H E D P Y T |
| T V S H L D D V G D N Y I H | M G S Y R G R | Q G S H G G P N T |
| K A S Q S V D Y D G D S Y M N | S G L Y L G S | H L S H G G P N T |
| K A S Q X T V D Y D G Y S V L L | A A S Y L G S | Q Q S H E D P Y T |
| H D I L S V D D D G D S Y M N | A A S Y L G S | Q Q S H E D P Y T |
| H T S Q S V D Y D G D S Y M N | A A S Y L G S | Q Q S H E D P Y T |
| K A S Q S V D Y D G D S Y M N | A S S Y L G S | Q Q S Q V E I P Y T |
| K A S Q C Q R S V D D K L G D I D S H | A A S Y L G S | Q Q S H E D P Y T |
| K A V Q S G D Y D G K G G N Y I N | A A S Y L G S | Q Q S H E D P Y T |
| K S R Q S G D Y D G D S Y M N | A A S Y L G S | Q Q S H K D P Y P |
| D V S S V V D Y D G D S Y M N | A S S Y L G S | Q Q S H E D P Y N |
| K A S Q S V D Y D G D S Y M N | A A S Y L G S | Q Q S H E D P Y T |

(SEQ ID NOS: 279-296) (SEQ ID NOS: 297-314) (SEQ ID NOS: 315-332)

FIG._3C-1

VH Domain of Initial Mae11 Library

| CDR-H1 | CDR-H2 | CDR-H3 |
|---|---|---|
| G Y S I T S G Y S W N | G S I T Y D G S S N Y N P S L K N | R G S H Y F G H W H F A V |
| G X S L T S S E C M S | G S S Y X D A Y S D Y I K S L L N | R G S H Y F G H W H F A V |
| G Y S H T T S G Y S W N | G S I T Y D G S S N Y N P S L K N | R G S H Y F G H W H F A V |
| G Y S H T T S G Y S W N | G S V H T Y V S S S X N L S R R N | K G R H Y F S E S H F A V |
| G Y S H T T S G Y S W N | G S I T Y D G S S N Y N P S L K N | R G S H Y F G H W H F A V |
| V S Y F T R D S C W N H | S V I T C Y R S S S X N W S L K N | K G R H H L A I R N F A G |
| G C W H F S G Y R W I | S G E R F P L R I N Y N P G L K Y | R G S R C C S Y X H F A S |
| G Y S H T T S G Y S W N | G R V T F A G S S V N F D P S L K N | R G R D N F V N W H V S V |
| G Y C H Y T G Y T W N | G C I T Y D G R S S X R N Y N L S L K Y | R G C L H Y H R X C G H R R F A F |
| C S G L A D G Y C H | S W H P Y A C S R N Y N P S L K N | R G G Q Y L G H W H V M V |
| G Y S H T T S G Y S W N | G S I T S H E D G S D X N P S P K N | R G S H Y F G H W H F A V |
| G Y F H T T N G Y S W N | G T I S H E D G S D X N P S P K N | R G S H Y F G H W H F A V |
| G Y S H T T S G Y S W N | G S I T Y D G S S N Y N L S L K Y | R G S H Y F G H W H F A V |
| G Y S H T T S G Y S W N | G S I T Y D G S S N Y N P S L K N | R G S H Y F G H W H F A V |
| G Y S H T T S G Y S W N | G S I T Y D G S S N Y N P S L K N | R G S H Y F G H W H F A V |

(SEQ ID NOS: 333-350) (SEQ ID NOS: 351-368) (SEQ ID NOS: 369-386)

*FIG._3C-2*

Selected Clones from the Mae11 Humanization Library

| IC50 (nM) | CDR-H1 | Additional Changes | | |
|---|---|---|---|---|
| | A A S [G Y S I T S G Y S W N] W V R | VL Domain | VH Domain | Siblings |
| 7 | A A S G Y S I S G G Y H L N W V R | | E46K | 3 |
| 4 | A A S G Y S I S G G Y R L N W V R | | | |
| 7 | A A S G Y I I T S G Y K L N W V R | | | |
| 6 | A A S G N S I T S G Y K L N W V R | | | |
| 9 | A A S G Y S I T S G H K L N W V R | | | |
| 6 | A A S G Y S I T S G Y K L N W V R | P80Q | | |
| 6 | A A S G Y S I T S G Y K L N W V R | | D72Y | |
| 2 | A A S G Y S I T S G Y K L N W V R | | S57I | |
| 4 | A A S G Y S I T S G Y K L N W V R | | | 37 |
| 6 | A A S G Y S I T S G Y N L N W V R | | | |
| 3 | A A S G Y S I T S G Y S L H W V R | | | 12 |

(SEQ ID NOS: 387-398)

Selected Clones from the MHM24 Humanization Library

| IC50 (nM) | CDR-L2 | Additional Changes | | |
|---|---|---|---|---|
| | L L I Y [S G S T L Q S] G V P S | VL Domain | VH Domain | Siblings |
| 9 | L L I Y S G S T L E S G V P S | | | 11 |
| 8 | L L I Y S G S T L E S G V P S | | D101E | |
| 4 | L L I Y T G S T L E S G V P S | S26T | | |
| 4 | L L I Y S G S T L E S G V P S | | S55I | |
| 6 | L L I Y S G G T L H R G V P S | | | |
| 41 | L L I Y S G Y S L H R G V P S | K27E, L96V | | |
| 11 | L L I Y S G R A M Q R G V P S | | | 2 |
| 9 | L L I Y S G R A L Q S G V P S | | | |
| 17 | L L I Y S G R S L Q S G V P S | | S28R | |
| 32 | L L I Y N A R S L Q S G V P S | | | |
| 8 | L L I Y S G S A L Q S G V P S | | | |
| 6 | L L I Y S G S T L Q S G V P S | | | |
| 11 | L L I Y S G S I F Q Y G V P S | | Y100dT | |
| 17 | L L I Y S G R T L W P G V P S | | | |
| 27 | L L I Y S G R S L Q R G V P S | | L45P | 8 |

(SEQ ID NOS: 399-414)

*FIG._4A*

Selected Clones from the D3 Humanization Library

CDR-L1

| IC50 (nM) | Sequence | VL Domain | VH Domain | Siblings |
|---|---|---|---|---|
| | I T C [K A S R D I K S Y L S] W Y Q | | | |
| 9 | I T C K G S G Y I K H F V S W Y Q | | | 2 |
| 19 | I T C K G S R D T T S F V S W Y Q | | | |
| 16 | I T C N A S L V I N R W L S W Y Q | | | |
| 21 | I T C K G Q R V L N S W L S W Y Q | | | |
| 19 | I T C K A S R D I K S Y L S W Y Q | | | 5 |

(SEQ ID NOS: 415-420)

CDR-L2

| IC50 (nM) | Sequence | Additional Changes | Siblings |
|---|---|---|---|
| | L I Y [Y A T S L A D] G V P | | |
| 17 | L I Y D A I G L A D G V P | | |
| 8 | L I Y Y A P G L A D G V P | | 2 |
| 4 | L I Y Y A P S L A D G V P | | |
| 10 | L I Y Y A P G P A D G V P | | |
| 11 | L I Y Y A P R R A R G V P | | 2 |
| 7 | L I Y Y E P G L A D G V P | | |
| 8 | L I Y Y E S G P A D G V P | | 2 |
| 16 | L I Y Y A T G E T D G V P | | 2 |
| 10 | L I Y Y E T G W A E G V P | | |
| 12 | L I Y Y E G S G K R G V P | | 8 |
| 11 | L I Y Y E T G E P E G V P | | |
| 9 | L I Y Y E T G P T D G V P | | |
| 10 | L I Y R G T S L F E G V P | K24E, D28V, Y32F | |
| 16 | L I Y Y T A G P S D G V P | | |
| 21 | L I Y Y T T G P V D G V P | | |
| 10 | L I Y Y V P W T A D G V P | | |

(SEQ ID NOS: 421-437)

CDR-L3

| IC50 (nM) | Sequence | Additional Changes | Siblings |
|---|---|---|---|
| | Y Y C [L Q H G E S P F T] F G Q | | |
| 13 | Y Y C L Q D G E S P F T F G Q | | 5 |
| 8 | Y Y C L Q D G E S P F T F G Q | I58F, N82aI, D95N | |
| 15 | Y Y C L S D G S S P F T F G Q | | |

(SEQ ID NOS: 438-441)

*FIG. 4B*

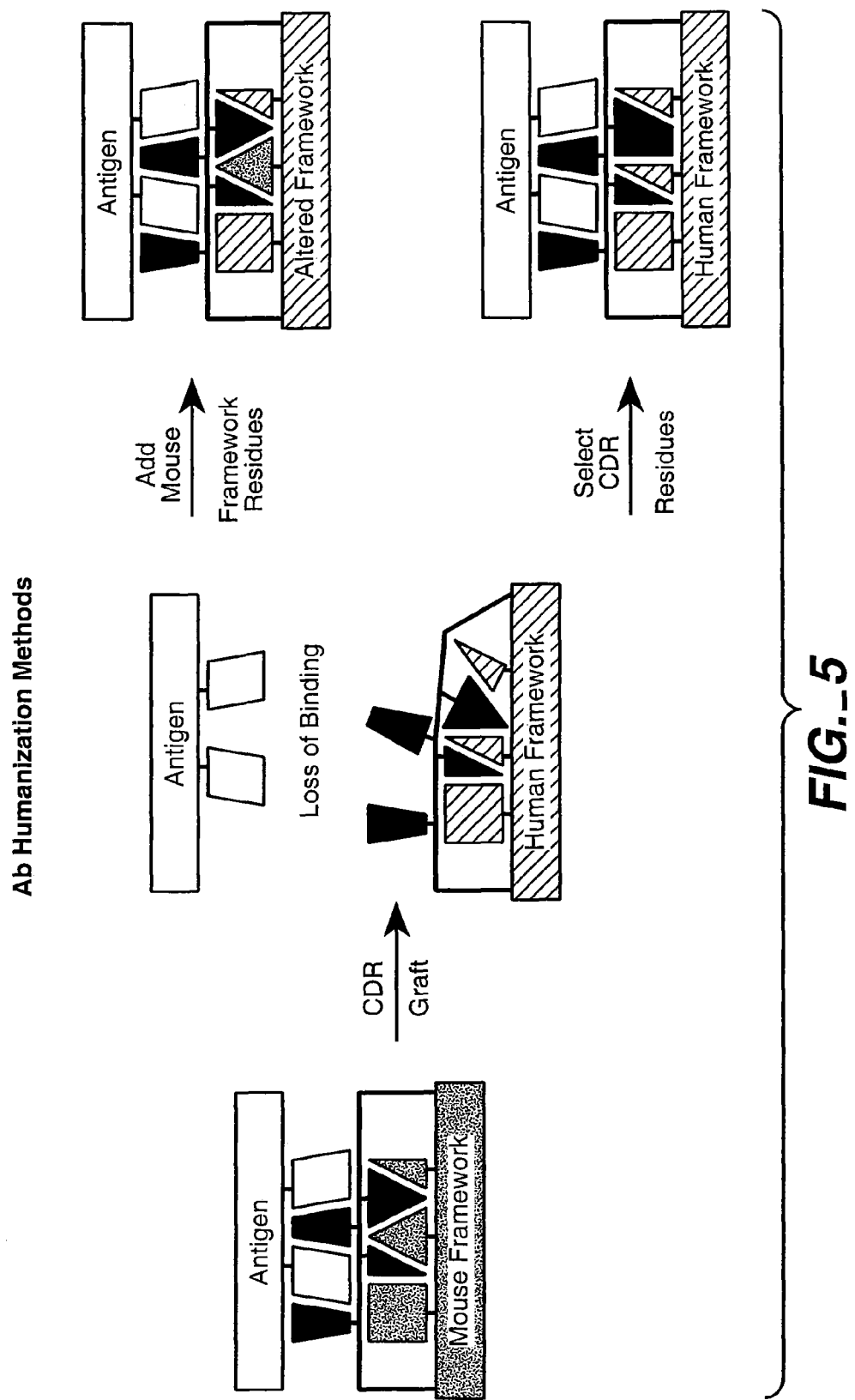
FIG._5 humhv1

| | | | |
|---|---|---|---|
| A | QVQLVQSGAEVKKPGASVKVSCKASGYTFT | -H1- | WVRQAPGQGLEWMG | -H2- | RVTI |
| B | QVQLVQSGAEVKKPGASVKVSCKAS | -H1- | WVRQAPGQGLEWM | -H2- | RVTI |
| C | QVQLVQSGAEVKKPGASVKVSCKAS | -H1- | WVRQAPGQGLEWM | -H2- | RVTI |
| D | QVQLVQSGAEVKKPGASVKVSCKAS | -H1- | WVRQAPGQGLEWM | -H2- | RVTI | humhv2

| | | | |
|---|---|---|---|
| A | QVQLQESGPGLVKPSQTLSLTCTVSGGSVS | -H1- | WIRQPPGKGLEWIG | -H2- | RVTI |
| B | QVQLQESGPGLVKPSQTLSLTCTVS | -H1- | WIRQPPGKGLEWI | -H2- | RVTI |
| C | QVQLQESGPGLVKPSQTLSLTCTVS | -H1- | WIRQPPGKGLEWI | -H2- | RVTI |
| D | QVQLQESGPGLVKPSQTLSLTCTVS | -H1- | WIRQPPGKGLEWI | -H2- | RVTI | humhv3

| | | | |
|---|---|---|---|
| A | EVQLVESGGGLVQPGGSLRLSCAASGFTFS | -H1- | WVRQAPGKGLEWVS | -H2- | RVTI |
| B | EVQLVESGGGLVQPGGSLRLSCAAS | -H1- | WVRQAPGKGLEWV | -H2- | RVTI |
| C | EVQLVESGGGLVQPGGSLRLSCAAS | -H1- | WVRQAPGKGLEWV | -H2- | RVTI |
| D | EVQLVESGGGLVQPGGSLRLSCAAS | -H1- | WVRQAPGKGLEWV | -H2- | RVTI |

Acceptor

| | | | |
|---|---|---|---|
| A | EVQLVESGGGLVQPGGSLRLSCAASGFNIK | -H1- | WVRQAPGKGLEWVS | -H2- | RVTI |
| B | EVQLVESGGGLVQPGGSLRLSCAAS | -H1- | WVRQAPGKGLEWV | -H2- | RVTI |
| C | EVQLVESGGGLVQPGGSLRLSCAAS | -H1- | WVRQAPGKGLEWV | -H2- | RVTI |

Second Acceptor

| | | | |
|---|---|---|---|
| A | EVQLVESGGGLVQPGGSLRLSCAASGFNIK | -H1- | WVRQAPGKGLEWVS | -H2- | RVTI |
| B | EVQLVESGGGLVQPGGSLRLSCAAS | -H1- | WVRQAPGKGLEWV | -H2- | RVTI |
| C | EVQLVESGGGLVQPGGSLRLSCAAS | -H1- | WVRQAPGKGLEWV | -H2- | RVTI |
| D | EVQLVESGGGLVQPGGSLRLSCAAS | -H1- | WVRQAPGKGLEWV | -H2- | RVTI |

| | | | | |
|---|---|---|---|---|
| humkv1 | DIQMTQSPSSLSASVGDRVTITC | -L1- | WYQQKPGKAPKLLIY | -L2- | GVPSRFSGSGS |
| humkv2 | DIVMTQSPLSLPVTPGEPASISC | -L1- | WYLQKPGQSPQLLIY | -L2- | GVPDRFSGSGS |
| humkv3 | EIVLTQSPGTLSLSPGERATLSC | -L1- | WYQQKPGQAPRLLIY | -L2- | GIPDRFSGSGS |
| humkv4 | DIVMTQSPDSLAVSLGERATINC | -L1- | WYQQKPGQPPKLLIY | -L2- | GVPDRFSGSGS |

FIG._6A

```
humhv1
A    TADTSTSTAYMELSSLRSEDTAVYYCAR    -H3-    WGQGTLVTVSS    SEQ ID NO.:23
B    TADTSTSTAYMELSSLRSEDTAVYYCAR    -H3-    WGQGTLVTVSS    SEQ ID NO.:24
C    TADTSTSTAYMELSSLRSEDTAVYYCAR    -H3-    WGQGTLVTVSS    SEQ ID NO.:25
D    TADTSTSTAYMELSSLRSEDTAVYYCA     -H3-    WGQGTLVTVSS    SEQ ID NO.:26 humhv2
A    SVDTSKNQFSLKLSSVTAADTAVYYCAR    -H3-    WGQGTLVTVSS    SEQ ID NO.:27
B    SVDTSKNQFSLKLSSVTAADTAVYYCAR    -H3-    WGQGTLVTVSS    SEQ ID NO.:28
C    SVDTSKNQFSLKLSSVTAADTAVYYCAR    -H3-    WGQGTLVTVSS    SEQ ID NO.:29
D    SVDTSKNQFSLKLSSVTAADTAVYYC      -H3-    WGQGTLVTVSS    SEQ ID NO.:30 humhv3
A    SRDNSKNTLYLQMNSLRAEDTAVYYCAR    -H3-    WGQGTLVTVSS    SEQ ID NO.:31
B    SRDNSKNTLYLQMNSLRAEDTAVYYCAR    -H3-    WGQGTLVTVSS    SEQ ID NO.:32
C    SRDNSKNTLYLQMNSLRAEDTAVYYCA     -H3-    WGQGTLVTVSS    SEQ ID NO.:33
D    SRDNSKNTLYLQMNSLRAEDTAVYYC      -H3-    WGQGTLVTVSS    SEQ ID NO.:34

Acceptor
A    SADTSKNTAYLQMNSLRAEDTAVYYCSR    -H3-    WGQGTLVTVSS    SEQ ID NO.:35
B    SADTSKNTAYLQMNSLRAEDTAVYYCSR    -H3-    WGQGTLVTVSS    SEQ ID NO.:36
C    SADTSKNTAYLQMNSLRAEDTAVYYCS     -H3-    WGQGTLVTVSS    SEQ ID NO.:37

Second Acceptor
A    SADTSKNTAYLQMNSLRAEDTAVYYCAR    -H3-    WGQGTLVTVSS    SEQ ID NO.:38
B    SADTSKNTAYLQMNSLRAEDTAVYYCAR    -H3-    WGQGTLVTVSS    SEQ ID NO.:39
C    SADTSKNTAYLQMNSLRAEDTAVYYCA     -H3-    WGQGTLVTVSS    SEQ ID NO.:40
D    SADTSKNTAYLQMNSLRAEDTAVYYC      -H3-    WGQGTLVTVSS    SEQ ID NO.:41 humkv1    GTDFTLTISSLQPEDFATYYC    -L3-    FGQGTKVEIK    SEQ ID NO.:42
humkv2    GTDFTLKISRVEAEDVGVYYC    -L3-    FGQGTKVEIK    SEQ ID NO.:43
humkv3    GTDFTLTISRLEPEDFAVYYC    -L3-    FGQGTKVEIK    SEQ ID NO.:44
humkv4    GTDFTLTISSLQAEDVAVYYC    -L3-    FGQGTKVEIK    SEQ ID NO.:45
```

*FIG._6B*

SEQUENCE LISTING

<160> NUMBER OF SEQ ID NOS: 441

<210> SEQ ID NO 1
<211> LENGTH: 25
<212> TYPE: PRT
<213> ORGANISM: Artificial sequence
<220> FEATURE:
<223> OTHER INFORMATION: Sequence is synthesized.

<400> SEQUENCE: 1

Glu Val Gln Leu Val Glu Ser Gly Gly Gly Leu Val Gln Pro Gly
 1               5                  10                  15

Gly Ser Leu Arg Leu Ser Cys Ala Ala Ser
            20                  25

<210> SEQ ID NO 2
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 2

Trp Val Arg Gln Ala Pro Gly Lys Gly Leu Glu Trp Val
 1               5                  10

<210> SEQ ID NO 3
<211> LENGTH: 30
<212> TYPE: PRT
<213> ORGANISM: Artificial sequence
<220> FEATURE:
<223> OTHER INFORMATION: Sequence is synthesized.

<400> SEQUENCE: 3

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
            20                  25                  30

<210> SEQ ID NO 4
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 4

Trp Gly Gln Gly Thr Leu Val Thr Val Ser Ser
 1               5                  10

<210> SEQ ID NO 5
<211> LENGTH: 23
<212> TYPE: PRT
<213> ORGANISM: Artificial sequence
<220> FEATURE:
<223> OTHER INFORMATION: Sequence is synthesized.

<400> SEQUENCE: 5

Asp Ile Gln Met Thr Gln Ser Pro Ser Ser Leu Ser Ala Ser Val
 1               5                  10                  15

Gly Asp Arg Val Thr Ile Thr Cys
            20

<210> SEQ ID NO 6

-continued

<211> LENGTH: 15
<212> TYPE: PRT
<213> ORGANISM: Artificial sequence
<220> FEATURE:
<223> OTHER INFORMATION: Sequence is synthesized.

<400> SEQUENCE: 6

Trp Tyr Gln Gln Lys Pro Gly Lys Ala Pro Lys Leu Leu Ile Tyr
 1               5                  10                  15

<210> SEQ ID NO 7
<211> LENGTH: 32
<212> TYPE: PRT
<213> ORGANISM: Artificial sequence
<220> FEATURE:
<223> OTHER INFORMATION: Sequence is synthesized.

<400> SEQUENCE: 7

Gly Val Pro Ser Arg Phe Ser Gly Ser Gly Ser Gly Thr Asp Phe
 1               5                  10                  15

Thr Leu Thr Ile Ser Ser Leu Gln Pro Glu Asp Phe Ala Thr Tyr
                20                  25                  30

Tyr Cys

<210> SEQ ID NO 8
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 8

Phe Gly Gln Gly Thr Lys Val Glu Ile Lys
 1               5                  10

<210> SEQ ID NO 9
<211> LENGTH: 30
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 6
<223> OTHER INFORMATION: Xaa is A or R
<220> FEATURE:
<221> NAME/KEY: Xaa
<222> LOCATION: 8
<223> OTHER INFORMATION: Xaa is T or N
<220> FEATURE:
<221> NAME/KEY: Xaa
<222> LOCATION: 13
<223> OTHER INFORMATION: Xaa is A or L

<400> SEQUENCE: 9

Arg Phe Thr Ile Ser Xaa Asp Xaa Ser Lys Asn Thr Xaa Tyr Leu
 1               5                  10                  15

Gln Met Asn Ser Leu Arg Ala Glu Asp Thr Ala Val Tyr Tyr Cys
                20                  25                  30

<210> SEQ ID NO 10
<211> LENGTH: 30
<212> TYPE: PRT
<213> ORGANISM: Artificial sequence
<220> FEATURE:
<223> OTHER INFORMATION: Sequence is synthesized.

<400> SEQUENCE: 10

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

<210> SEQ ID NO 11
<211> LENGTH: 31
<212> TYPE: PRT
<213> ORGANISM: Artificial sequence
<220> FEATURE:
<223> OTHER INFORMATION: Sequence is synthesized.

<400> SEQUENCE: 11

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

Ala

<210> SEQ ID NO 12
<211> LENGTH: 32
<212> TYPE: PRT
<213> ORGANISM: Artificial sequence
<220> FEATURE:
<223> OTHER INFORMATION: Sequence is synthesized.

<400> SEQUENCE: 12

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

Ala Arg

<210> SEQ ID NO 13
<211> LENGTH: 31
<212> TYPE: PRT
<213> ORGANISM: Artificial sequence
<220> FEATURE:
<223> OTHER INFORMATION: Sequence is synthesized.

<400> SEQUENCE: 13

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

Ser

<210> SEQ ID NO 14
<211> LENGTH: 32
<212> TYPE: PRT
<213> ORGANISM: Artificial sequence
<220> FEATURE:
<223> OTHER INFORMATION: Sequence is synthesized.

<400> SEQUENCE: 14

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
            20                  25                  30

Ser Arg

<210> SEQ ID NO 15

```
<211> LENGTH: 81
<212> TYPE: PRT
<213> ORGANISM: Artificial sequence
<220> FEATURE:
<223> OTHER INFORMATION: Sequence is synthesized.

<400> SEQUENCE: 15

Asp Ile Gln Met Thr Gln Ser Pro Ser Ser Leu Ser Ala Ser Val
 1               5                  10                  15

Gly Asp Arg Val Thr Ile Thr Cys Trp Tyr Gln Gln Lys Pro Gly
                20                  25                  30

Lys Ala Pro Lys Leu Leu Ile Tyr Gly Val Pro Ser Arg Phe Ser
                35                  40                  45

Gly Ser Gly Ser Gly Thr Asp Phe Thr Leu Thr Ile Ser Ser Leu
                50                  55                  60

Gln Pro Glu Asp Phe Ala Thr Tyr Tyr Cys Phe Gly Gln Gly Thr
                65                  70                  75

Lys Val Glu Ile Lys Arg
                80

<210> SEQ ID NO 16
<211> LENGTH: 108
<212> TYPE: PRT
<213> ORGANISM: Artificial sequence
<220> FEATURE:
<223> OTHER INFORMATION: Sequence is synthesized.

<400> SEQUENCE: 16

Asp Val Gln Ile Thr Gln Ser Pro Ser Tyr Leu Ala Ala Ser Pro
 1               5                  10                  15

Gly Glu Thr Ile Ser Ile Asn Cys Arg Ala Ser Lys Thr Ile Ser
                20                  25                  30

Lys Tyr Leu Ala Trp Tyr Gln Glu Lys Pro Gly Lys Thr Asn Lys
                35                  40                  45

Leu Leu Ile Tyr Ser Gly Ser Thr Leu Gln Ser Gly Ile Pro Ser
                50                  55                  60

Arg Phe Ser Gly Ser Gly Ser Gly Thr Asp Phe Thr Leu Thr Ile
                65                  70                  75

Ser Ser Leu Glu Pro Glu Asp Phe Ala Met Tyr Tyr Cys Gln Gln
                80                  85                  90

His Asn Glu Tyr Pro Leu Thr Phe Gly Thr Gly Thr Lys Leu Glu
                95                 100                 105

Leu Lys Arg

<210> SEQ ID NO 17
<211> LENGTH: 112
<212> TYPE: PRT
<213> ORGANISM: Artificial sequence
<220> FEATURE:
<223> OTHER INFORMATION: Sequence is synthesized.

<400> SEQUENCE: 17

Asp Ile Val Leu Thr Gln Ser Pro Ala Ser Leu Ala Val Ser Leu
 1               5                  10                  15

Gly Gln Arg Ala Thr Ile Ser Cys Lys Ala Ser Gln Ser Val Asp
                20                  25                  30

Tyr Asp Gly Asp Ser Tyr Met Asn Trp Tyr Gln Gln Lys Pro Gly
                35                  40                  45

Gln Pro Pro Ile Leu Leu Ile Tyr Ala Ala Ser Tyr Leu Gly Ser
                50                  55                  60
```

```
Glu Ile Pro Ala Arg Phe Ser Gly Ser Gly Ser Gly Thr Asp Phe
                65                  70                  75

Thr Leu Asn Ile His Pro Val Glu Glu Asp Ala Ala Thr Phe
            80                  85                  90

Tyr Cys Gln Gln Ser His Glu Asp Pro Tyr Thr Phe Gly Ala Gly
                95                  100                 105

Thr Lys Leu Glu Ile Lys Arg
            110
```

<210> SEQ ID NO 18
<211> LENGTH: 108
<212> TYPE: PRT
<213> ORGANISM: Artificial sequence
<220> FEATURE:
<223> OTHER INFORMATION: Sequence is synthesized.

<400> SEQUENCE: 18

```
Asp Ile Lys Met Thr Gln Ser Pro Ser Ser Met Ser Ala Ser Leu
 1               5                  10                  15

Gly Glu Ser Val Thr Ile Thr Cys Lys Ala Ser Arg Asp Ile Lys
                20                  25                  30

Ser Tyr Leu Ser Trp Tyr Gln Gln Lys Pro Trp Lys Ser Pro Lys
                35                  40                  45

Thr Leu Ile Tyr Tyr Ala Thr Ser Leu Ala Asp Gly Val Pro Ser
                50                  55                  60

Arg Phe Ser Gly Ser Gly Ser Gly Gln Asp Tyr Ser Leu Thr Ile
                65                  70                  75

Ser Ser Leu Glu Ser Asp Asp Thr Ala Thr Tyr Tyr Cys Leu Gln
                80                  85                  90

His Gly Glu Ser Pro Phe Thr Phe Gly Ser Gly Thr Lys Leu Glu
                95                  100                 105

Leu Lys Arg
```

<210> SEQ ID NO 19
<211> LENGTH: 79
<212> TYPE: PRT
<213> ORGANISM: Artificial sequence
<220> FEATURE:
<223> OTHER INFORMATION: Sequence is synthesized.

<400> SEQUENCE: 19

```
Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Ala Asp
                35                  40                  45

Thr Ser Lys Asn Thr Ala Tyr Leu Gln Met Asn Ser Leu Arg Ala
                50                  55                  60

Glu Asp Thr Ala Val Tyr Tyr Cys Trp Gly Gln Gly Thr Leu Val
                65                  70                  75

Thr Val Ser Ser
```

<210> SEQ ID NO 20
<211> LENGTH: 121
<212> TYPE: PRT
<213> ORGANISM: Artificial sequence
<220> FEATURE:
<223> OTHER INFORMATION: Sequence is synthesized.

<400> SEQUENCE: 20

Glu Val Gln Leu Gln Gln Pro Gly Ala Glu Leu Met Arg Pro Gly
1               5                   10                  15

Ala Ser Val Lys Leu Ser Cys Lys Ala Ser Gly Tyr Ser Phe Thr
            20                  25                  30

Gly His Trp Met Asn Trp Val Arg Gln Arg Pro Gly Gln Gly Leu
        35                  40                  45

Glu Trp Ile Gly Met Ile His Pro Ser Asp Ser Glu Thr Arg Leu
    50                  55                  60

Asn Gln Lys Phe Lys Asp Lys Ala Thr Leu Thr Val Asp Lys Ser
65                  70                  75

Ser Ser Ser Ala Tyr Met Gln Leu Ser Ser Pro Thr Ser Glu Asp
            80                  85                  90

Ser Ala Val Tyr Tyr Cys Ala Arg Gly Ile Tyr Phe Tyr Gly Thr
            95                  100                 105

Thr Tyr Phe Asp Tyr Trp Gly Gln Gly Thr Thr Leu Thr Val Ser
            110                 115                 120

Ser

<210> SEQ ID NO 21
<211> LENGTH: 121
<212> TYPE: PRT
<213> ORGANISM: Artificial sequence
<220> FEATURE:
<223> OTHER INFORMATION: Sequence is synthesized.

<400> SEQUENCE: 21

Asp Val Gln Leu Gln Glu Ser Gly Pro Gly Leu Val Lys Pro Ser
1               5                   10                  15

Gln Ser Leu Ser Leu Ala Cys Ser Val Thr Gly Tyr Ser Ile Thr
            20                  25                  30

Ser Gly Tyr Ser Trp Asn Trp Ile Arg Gln Phe Pro Gly Asn Lys
        35                  40                  45

Leu Glu Trp Met Gly Ser Ile Thr Tyr Asp Gly Ser Ser Asn Tyr
    50                  55                  60

Asn Pro Ser Leu Lys Asn Arg Ile Ser Val Thr Arg Asp Thr Ser
65                  70                  75

Gln Asn Gln Phe Phe Leu Lys Leu Asn Ser Ala Thr Ala Glu Asp
            80                  85                  90

Thr Ala Thr Tyr Tyr Cys Ala Arg Gly Ser His Tyr Phe Gly His
            95                  100                 105

Trp His Phe Ala Val Trp Gly Ala Gly Thr Thr Val Thr Val Ser
            110                 115                 120

Ser

<210> SEQ ID NO 22
<211> LENGTH: 117
<212> TYPE: PRT
<213> ORGANISM: Artificial sequence
<220> FEATURE:
<223> OTHER INFORMATION: Sequence is synthesized.

<400> SEQUENCE: 22

Glu Val Gln Leu Gln Gln Ser Gly Ala Glu Leu Val Arg Pro Gly
1               5                   10                  15

Ala Leu Val Lys Leu Ser Cys Lys Ala Ser Gly Phe Asn Ile Lys
            20                  25                  30

```
Asp Tyr Tyr Met His Trp Val Lys Gln Arg Pro Glu Gln Gly Leu
                35                  40                  45

Glu Leu Ile Gly Trp Ile Asp Pro Glu Asn Gly Asn Thr Ile Tyr
         50                  55                  60

Asp Pro Lys Phe Gln Asp Lys Ala Ser Ile Thr Ala Asp Thr Ser
     65                  70                  75

Ser Asn Thr Ala Tyr Leu Gln Leu Ser Ser Leu Thr Ser Glu Asp
 80                  85                  90

Thr Ala Val Tyr Tyr Cys Ala Arg Asp Thr Ala Ala Tyr Phe Asp
             95                 100                 105

Tyr Trp Gly Gln Gly Thr Thr Leu Thr Val Ser Ser
                110                 115

<210> SEQ ID NO 23
<211> LENGTH: 87
<212> TYPE: PRT
<213> ORGANISM: Artificial sequence
<220> FEATURE:
<223> OTHER INFORMATION: Sequence is synthesized.

<400> SEQUENCE: 23

Gln Val Gln Leu Val Gln Ser Gly Ala Glu Val Lys Lys Pro Gly
  1               5                  10                  15

Ala Ser Val Lys Val Ser Cys Lys Ala Ser Gly Tyr Thr Phe Thr
             20                  25                  30

Trp Val Arg Gln Ala Pro Gly Gln Gly Leu Glu Trp Met Gly Arg
         35                  40                  45

Val Thr Ile Thr Ala Asp Thr Ser Thr Ser Thr Ala Tyr Met Glu
     50                  55                  60

Leu Ser Ser Leu Arg Ser Glu Asp Thr Ala Val Tyr Tyr Cys Ala
 65                  70                  75

Arg Trp Gly Gln Gly Thr Leu Val Thr Val Ser Ser
             80                  85

<210> SEQ ID NO 24
<211> LENGTH: 81
<212> TYPE: PRT
<213> ORGANISM: Artificial sequence
<220> FEATURE:
<223> OTHER INFORMATION: Sequence is synthesized.

<400> SEQUENCE: 24

Gln Val Gln Leu Val Gln Ser Gly Ala Glu Val Lys Lys Pro Gly
  1               5                  10                  15

Ala Ser Val Lys Val Ser Cys Lys Ala Ser Trp Val Arg Gln Ala
             20                  25                  30

Pro Gly Gln Gly Leu Glu Trp Met Arg Val Thr Ile Thr Ala Asp
         35                  40                  45

Thr Ser Thr Ser Thr Ala Tyr Met Glu Leu Ser Ser Leu Arg Ser
     50                  55                  60

Glu Asp Thr Ala Val Tyr Tyr Cys Ala Arg Trp Gly Gln Gly Thr
 65                  70                  75

Leu Val Thr Val Ser Ser
             80

<210> SEQ ID NO 25
<211> LENGTH: 80
<212> TYPE: PRT
<213> ORGANISM: Artificial sequence
```

```
<220> FEATURE:
<223> OTHER INFORMATION: Sequence is synthesized.

<400> SEQUENCE: 25

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
                20                  25                  30

Pro Gly Gln Gly Leu Glu Trp Met Arg Val Thr Ile Thr Ala Asp
            35                  40                  45

Thr Ser Thr Ser Thr Ala Tyr Met Glu Leu Ser Ser Leu Arg Ser
        50                  55                  60

Glu Asp Thr Ala Val Tyr Tyr Cys Ala Trp Gly Gln Gly Thr Leu
 65                  70                  75

Val Thr Val Ser Ser
            80

<210> SEQ ID NO 26
<211> LENGTH: 79
<212> TYPE: PRT
<213> ORGANISM: Artificial sequence
<220> FEATURE:
<223> OTHER INFORMATION: Sequence is synthesized.

<400> SEQUENCE: 26

Gln Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
                20                  25                  30

Pro Gly Gln Gly Leu Glu Trp Met Arg Val Thr Ile Thr Ala Asp
            35                  40                  45

Thr Ser Thr Ser Thr Ala Tyr Met Glu Leu Ser Ser Leu Arg Ser
        50                  55                  60

Glu Asp Thr Ala Val Tyr Tyr Cys Trp Gly Gln Gly Thr Leu Val
 65                  70                  75

Thr Val Ser Ser

<210> SEQ ID NO 27
<211> LENGTH: 87
<212> TYPE: PRT
<213> ORGANISM: Artificial sequence
<220> FEATURE:
<223> OTHER INFORMATION: Sequence is synthesized.

<400> SEQUENCE: 27

Gln Val Gln Leu Gln Glu Ser Gly Pro Gly Leu Val Lys Pro Ser
 1               5                  10                  15

Gln Thr Leu Ser Leu Thr Cys Thr Val Ser Gly Gly Ser Val Ser
                20                  25                  30

Trp Ile Arg Gln Pro Pro Gly Lys Gly Leu Glu Trp Ile Gly Arg
            35                  40                  45

Val Thr Ile Ser Val Asp Thr Ser Lys Asn Gln Phe Ser Leu Lys
        50                  55                  60

Leu Ser Ser Val Thr Ala Ala Asp Thr Ala Val Tyr Tyr Cys Ala
 65                  70                  75

Arg Trp Gly Gln Gly Thr Leu Val Thr Val Ser Ser
            80                  85

<210> SEQ ID NO 28
```

```
<211> LENGTH: 81
<212> TYPE: PRT
<213> ORGANISM: Artificial sequence
<220> FEATURE:
<223> OTHER INFORMATION: Sequence is synthesized.

<400> SEQUENCE: 28

Gln Val Gln Leu Gln Glu Ser Gly Pro Gly Leu Val Lys Pro Ser
  1               5                  10                  15

Gln Thr Leu Ser Leu Thr Cys Thr Val Ser Trp Ile Arg Gln Pro
             20                  25                  30

Pro Gly Lys Gly Leu Glu Trp Ile Arg Val Thr Ile Ser Val Asp
         35                  40                  45

Thr Ser Lys Asn Gln Phe Ser Leu Lys Leu Ser Ser Val Thr Ala
     50                  55                  60

Ala Asp Thr Ala Val Tyr Tyr Cys Ala Arg Trp Gly Gln Gly Thr
 65                  70                  75

Leu Val Thr Val Ser Ser
             80

<210> SEQ ID NO 29
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 29

Gln Val Gln Leu Gln Glu Ser Gly Pro Gly Leu Val Lys Pro Ser
  1               5                  10                  15

Gln Thr Leu Ser Leu Thr Cys Thr Val Ser Trp Ile Arg Gln Pro
             20                  25                  30

Pro Gly Lys Gly Leu Glu Trp Ile Arg Val Thr Ile Ser Val Asp
         35                  40                  45

Thr Ser Lys Asn Gln Phe Ser Leu Lys Leu Ser Ser Val Thr Ala
     50                  55                  60

Ala Asp Thr Ala Val Tyr Tyr Cys Ala Trp Gly Gln Gly Thr Leu
 65                  70                  75

Val Thr Val Ser Ser
             80

<210> SEQ ID NO 30
<211> LENGTH: 79
<212> TYPE: PRT
<213> ORGANISM: Artificial sequence
<220> FEATURE:
<223> OTHER INFORMATION: Sequence is synthesized.

<400> SEQUENCE: 30

Gln Val Gln Leu Gln Glu Ser Gly Pro Gly Leu Val Lys Pro Ser
  1               5                  10                  15

Gln Thr Leu Ser Leu Thr Cys Thr Val Ser Trp Ile Arg Gln Pro
             20                  25                  30

Pro Gly Lys Gly Leu Glu Trp Ile Arg Val Thr Ile Ser Val Asp
         35                  40                  45

Thr Ser Lys Asn Gln Phe Ser Leu Lys Leu Ser Ser Val Thr Ala
     50                  55                  60

Ala Asp Thr Ala Val Tyr Tyr Cys Trp Gly Gln Gly Thr Leu Val
 65                  70                  75

Thr Val Ser Ser
```

```
<210> SEQ ID NO 31
<211> LENGTH: 87
<212> TYPE: PRT
<213> ORGANISM: Artificial sequence
<220> FEATURE:
<223> OTHER INFORMATION: Sequence is synthesized.

<400> SEQUENCE: 31

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Trp Val Arg Gln Ala Pro Gly Lys Gly Leu Glu Trp Val Ser Arg
                35                  40                  45

Phe Thr Ile Ser Arg Asp Asn Ser Lys Asn Thr Leu Tyr Leu Gln
                50                  55                  60

Met Asn Ser Leu Arg Ala Glu Asp Thr Ala Val Tyr Tyr Cys Ala
                65                  70                  75

Arg Trp Gly Gln Gly Thr Leu Val Thr Val Ser Ser
                80                  85

<210> SEQ ID NO 32
<211> LENGTH: 81
<212> TYPE: PRT
<213> ORGANISM: Artificial sequence
<220> FEATURE:
<223> OTHER INFORMATION: Sequence is synthesized.

<400> SEQUENCE: 32

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Arg Asp
                35                  40                  45

Asn Ser Lys Asn Thr Leu Tyr Leu Gln Met Asn Ser Leu Arg Ala
                50                  55                  60

Glu Asp Thr Ala Val Tyr Tyr Cys Ala Arg Trp Gly Gln Gly Thr
                65                  70                  75

Leu Val Thr Val Ser Ser
                80

<210> SEQ ID NO 33
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 33

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Arg Asp
                35                  40                  45

Asn Ser Lys Asn Thr Leu Tyr Leu Gln Met Asn Ser Leu Arg Ala
                50                  55                  60

Glu Asp Thr Ala Val Tyr Tyr Cys Ala Trp Gly Gln Gly Thr Leu
```

```
                65                  70                  75

Val Thr Val Ser Ser
                80

<210> SEQ ID NO 34
<211> LENGTH: 79
<212> TYPE: PRT
<213> ORGANISM: Artificial sequence
<220> FEATURE:
<223> OTHER INFORMATION: Sequence is synthesized.

<400> SEQUENCE: 34

Glu Val Gln Leu Val Glu Ser Gly Gly Gly Leu Val Gln Pro Gly
1               5                   10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Arg Asp
                35                  40                  45

Asn Ser Lys Asn Thr Leu Tyr Leu Gln Met Asn Ser Leu Arg Ala
                50                  55                  60

Glu Asp Thr Ala Val Tyr Tyr Cys Trp Gly Gln Gly Thr Leu Val
                65                  70                  75

Thr Val Ser Ser

<210> SEQ ID NO 35
<211> LENGTH: 87
<212> TYPE: PRT
<213> ORGANISM: Artificial sequence
<220> FEATURE:
<223> OTHER INFORMATION: Sequence is synthesized.

<400> SEQUENCE: 35

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys
                20                  25                  30

Trp Val Arg Gln Ala Pro Gly Lys Gly Leu Glu Trp Val Ser Arg
                35                  40                  45

Phe Thr Ile Ser Ala Asp Thr Ser Lys Asn Thr Ala Tyr Leu Gln
                50                  55                  60

Met Asn Ser Leu Arg Ala Glu Asp Thr Ala Val Tyr Tyr Cys Ser
                65                  70                  75

Arg Trp Gly Gln Gly Thr Leu Val Thr Val Ser Ser
                80                  85

<210> SEQ ID NO 36
<211> LENGTH: 81
<212> TYPE: PRT
<213> ORGANISM: Artificial sequence
<220> FEATURE:
<223> OTHER INFORMATION: Sequence is synthesized.

<400> SEQUENCE: 36

Glu Val Gln Leu Val Glu Ser Gly Gly Gly Leu Val Gln Pro Gly
1               5                   10                  15

Gly Ser Leu Arg Leu Ser Cys Ala Ala Ser Trp Val Arg Gln Ala
                20                  25                  30

Pro Gly Lys Gly Leu Glu Trp Val Arg Phe Thr Ile Ser Ala Asp
                35                  40                  45

Thr Ser Lys Asn Thr Ala Tyr Leu Gln Met Asn Ser Leu Arg Ala
```

```
                            50                  55                  60
Glu Asp Thr Ala Val Tyr Tyr Cys Ser Arg Trp Gly Gln Gly Thr
                65                  70                  75
Leu Val Thr Val Ser Ser
                80

<210> SEQ ID NO 37
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 37

Glu Val Gln Leu Val Glu Ser Gly Gly Gly Leu Val Gln Pro Gly
  1               5                  10                  15

Gly Ser Leu Arg Leu Ser Cys Ala Ala Ser Trp Val Arg Gln Ala
                 20                  25                  30

Pro Gly Lys Gly Leu Glu Trp Val Arg Phe Thr Ile Ser Ala Asp
                 35                  40                  45

Thr Ser Lys Asn Thr Ala Tyr Leu Gln Met Asn Ser Leu Arg Ala
                 50                  55                  60

Glu Asp Thr Ala Val Tyr Tyr Cys Ser Trp Gly Gln Gly Thr Leu
                 65                  70                  75

Val Thr Val Ser Ser
                 80

<210> SEQ ID NO 38
<211> LENGTH: 87
<212> TYPE: PRT
<213> ORGANISM: Artificial sequence
<220> FEATURE:
<223> OTHER INFORMATION: Sequence is synthesized.

<400> SEQUENCE: 38

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
                 20                  25                  30

Trp Val Arg Gln Ala Pro Gly Lys Gly Leu Glu Trp Val Ser Arg
                 35                  40                  45

Phe Thr Ile Ser Ala Asp Thr Ser Lys Asn Thr Ala Tyr Leu Gln
                 50                  55                  60

Met Asn Ser Leu Arg Ala Glu Asp Thr Ala Val Tyr Tyr Cys Ala
                 65                  70                  75

Arg Trp Gly Gln Gly Thr Leu Val Thr Val Ser Ser
                 80                  85

<210> SEQ ID NO 39
<211> LENGTH: 81
<212> TYPE: PRT
<213> ORGANISM: Artificial sequence
<220> FEATURE:
<223> OTHER INFORMATION: Sequence is synthesized.

<400> SEQUENCE: 39

Glu Val Gln Leu Val Glu Ser Gly Gly Gly Leu Val Gln Pro Gly
  1               5                  10                  15

Gly Ser Leu Arg Leu Ser Cys Ala Ala Ser Trp Val Arg Gln Ala
                 20                  25                  30
```

Pro Gly Lys Gly Leu Glu Trp Val Arg Phe Thr Ile Ser Ala Asp
            35                  40                  45

Thr Ser Lys Asn Thr Ala Tyr Leu Gln Met Asn Ser Leu Arg Ala
            50                  55                  60

Glu Asp Thr Ala Val Tyr Tyr Cys Ala Arg Trp Gly Gln Gly Thr
            65                  70                  75

Leu Val Thr Val Ser Ser
            80

<210> SEQ ID NO 40
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 40

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
            35                  40                  45

Thr Ser Lys Asn Thr Ala Tyr Leu Gln Met Asn Ser Leu Arg Ala
            50                  55                  60

Glu Asp Thr Ala Val Tyr Tyr Cys Ala Trp Gly Gln Gly Thr Leu
            65                  70                  75

Val Thr Val Ser Ser
            80

<210> SEQ ID NO 41
<211> LENGTH: 79
<212> TYPE: PRT
<213> ORGANISM: Artificial sequence
<220> FEATURE:
<223> OTHER INFORMATION: Sequence is synthesized.

<400> SEQUENCE: 41

Glu Val Gln Leu Val Glu Ser Gly Gly Gly Leu Val Gln Pro Gly
 1               5                  10                  15

Gly Ser Leu Arg Leu Ser Cys Ala Ala Ser Trp Val Arg Gln Ala
            20                  25                  30

Pro Gly Lys Gly Leu Glu Trp Val Arg Phe Thr Ile Ser Ala Asp
            35                  40                  45

Thr Ser Lys Asn Thr Ala Tyr Leu Gln Met Asn Ser Leu Arg Ala
            50                  55                  60

Glu Asp Thr Ala Val Tyr Tyr Cys Trp Gly Gln Gly Thr Leu Val
            65                  70                  75

Thr Val Ser Ser

<210> SEQ ID NO 42
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 42

Asp Ile Gln Met Thr Gln Ser Pro Ser Ser Leu Ser Ala Ser Val
 1               5                  10                  15

```
Gly Asp Arg Val Thr Ile Thr Cys Trp Tyr Gln Gln Lys Pro Gly
            20                  25                  30

Lys Ala Pro Lys Leu Leu Ile Tyr Gly Val Pro Ser Arg Phe Ser
            35                  40                  45

Gly Ser Gly Ser Gly Thr Asp Phe Thr Leu Thr Ile Ser Ser Leu
            50                  55                  60

Gln Pro Glu Asp Phe Ala Thr Tyr Tyr Cys Phe Gly Gln Gly Thr
            65                  70                  75

Lys Val Glu Ile Lys
            80

<210> SEQ ID NO 43
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 43

Asp Ile Val Met Thr Gln Ser Pro Leu Ser Leu Pro Val Thr Pro
  1               5                  10                  15

Gly Glu Pro Ala Ser Ile Ser Cys Trp Tyr Leu Gln Lys Pro Gly
            20                  25                  30

Gln Ser Pro Gln Leu Leu Ile Tyr Gly Val Pro Asp Arg Phe Ser
            35                  40                  45

Gly Ser Gly Ser Gly Thr Asp Phe Thr Leu Lys Ile Ser Arg Val
            50                  55                  60

Glu Ala Glu Asp Val Gly Val Tyr Tyr Cys Phe Gly Gln Gly Thr
            65                  70                  75

Lys Val Glu Ile Lys
            80

<210> SEQ ID NO 44
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 44

Glu Ile Val Leu Thr Gln Ser Pro Gly Thr Leu Ser Leu Ser Pro
  1               5                  10                  15

Gly Glu Arg Ala Thr Leu Ser Cys Trp Tyr Gln Gln Lys Pro Gly
            20                  25                  30

Gln Ala Pro Arg Leu Leu Ile Tyr Gly Ile Pro Asp Arg Phe Ser
            35                  40                  45

Gly Ser Gly Ser Gly Thr Asp Phe Thr Leu Thr Ile Ser Arg Leu
            50                  55                  60

Glu Pro Glu Asp Phe Ala Val Tyr Tyr Cys Phe Gly Gln Gly Thr
            65                  70                  75

Lys Val Glu Ile Lys
            80

<210> SEQ ID NO 45
<211> LENGTH: 80
<212> TYPE: PRT
<213> ORGANISM: Artificial sequence
<220> FEATURE:
<223> OTHER INFORMATION: Sequence is synthesized.

<400> SEQUENCE: 45
```

Asp Ile Val Met Thr Gln Ser Pro Asp Ser Leu Ala Val Ser Leu
1               5                   10                  15

Gly Glu Arg Ala Thr Ile Asn Cys Trp Tyr Gln Gln Lys Pro Gly
            20                  25                  30

Gln Pro Pro Lys Leu Leu Ile Tyr Gly Val Pro Asp Arg Phe Ser
            35                  40                  45

Gly Ser Gly Ser Gly Thr Asp Phe Thr Leu Thr Ile Ser Ser Leu
            50                  55                  60

Gln Ala Glu Asp Val Ala Val Tyr Tyr Cys Phe Gly Gln Gly Thr
            65                  70                  75

Lys Val Glu Ile Lys
            80

<210> SEQ ID NO 46
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 46

Lys Ala Ser Arg Asp Ile Lys Ser Tyr Leu Ser
1               5                   10

<210> SEQ ID NO 47
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 47

Lys Ala Leu Arg Tyr Asn Glu Arg Phe Leu Arg
1               5                   10

<210> SEQ ID NO 48
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 48

Lys Ala Ser Arg Asp Ile Lys Ser Tyr Leu Ser
1               5                   10

<210> SEQ ID NO 49
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 49

Gln Ser Cys Thr Asp Val Gln Ser Lys Glu Ser
1               5                   10

<210> SEQ ID NO 50
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 50

```
Lys Ala Thr Asp Glu Ile Lys Ser Gln Leu Ser
  1               5                  10
```

<210> SEQ ID NO 51
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 51

```
Lys Ala Ser Arg Asp Ile Lys Ser Tyr Leu Ser
  1               5                  10
```

<210> SEQ ID NO 52
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 52

```
Lys Ala Ser Arg Asp Ile Lys Ser Tyr Leu Ser
  1               5                  10
```

<210> SEQ ID NO 53
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 53

```
Leu Trp Ser Leu His Ile Lys Arg Tyr Leu Ser
  1               5                  10
```

<210> SEQ ID NO 54
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 54

```
Lys Ala Ile Arg Asp Thr Gln Ile Ser Leu Gly
  1               5                  10
```

<210> SEQ ID NO 55
<211> LENGTH: 11
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Unknown amino acid

<400> SEQUENCE: 55

```
Ile Glu Thr Arg Val Ile Thr Ser Xaa Leu Gln
  1               5                  10
```

<210> SEQ ID NO 56
<211> LENGTH: 11
<212> TYPE: PRT
<213> ORGANISM: Artificial sequence
<220> FEATURE:
<223> OTHER INFORMATION: Sequence is synthesized.

```
<220> FEATURE:
<221> NAME/KEY: Xaa
<222> LOCATION: 8
<223> OTHER INFORMATION: Unknown amino acid

<400> SEQUENCE: 56

Lys Gly Ser Arg Tyr Asn Lys Xaa Asn Leu Arg
 1               5                  10

<210> SEQ ID NO 57
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 57

Lys Ala Ser Ser Asp Ile Asn Ser Gln Leu Ser
 1               5                  10

<210> SEQ ID NO 58
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 58

Ile Glu Ser Arg Ala Phe Gln Ser Phe Met Ser
 1               5                  10

<210> SEQ ID NO 59
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 59

Lys Ala Ser Arg Asp Ile Lys Ser Tyr Leu Ser
 1               5                  10

<210> SEQ ID NO 60
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 60

Lys Gly Ile Val His Ile Met Trp His Leu Ser
 1               5                  10

<210> SEQ ID NO 61
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 61

Lys Ala Ser Arg Asp Ile Lys Ser Tyr Leu Ser
 1               5                  10

<210> SEQ ID NO 62
<211> LENGTH: 11
<212> TYPE: PRT
<213> ORGANISM: Artificial sequence
```

```
<220> FEATURE:
<223> OTHER INFORMATION: Sequence is synthesized.

<400> SEQUENCE: 62

Lys Ala Ser Arg Asp Ile Lys Ser Tyr Leu Ser
 1               5                   10

<210> SEQ ID NO 63
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 63

Lys Ser Asn His Ser Ser Lys Ser Tyr Leu Ser
 1               5                   10

<210> SEQ ID NO 64
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 64

Thr Glu Gly Arg His Val Lys Cys Tyr Leu Ser
 1               5                   10

<210> SEQ ID NO 65
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 65

Lys Ala Ser Arg Asp Ile Lys Ser Tyr Leu Ser
 1               5                   10

<210> SEQ ID NO 66
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 66

Tyr Ala Thr Ser Leu Ala Asp
 1               5

<210> SEQ ID NO 67
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 67

Tyr Ala Ser Ser Gln Ala Glu
 1               5

<210> SEQ ID NO 68
<211> LENGTH: 7
<212> TYPE: PRT
<213> ORGANISM: Artificial sequence
<220> FEATURE:
<223> OTHER INFORMATION: Sequence is synthesized.
```

```
<400> SEQUENCE: 68

Tyr Ala Thr Ser Leu Ala Asp
  1               5

<210> SEQ ID NO 69
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 69

Cys Ala Thr Arg Pro Ala Asp
  1               5

<210> SEQ ID NO 70
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 70

Tyr Ala Lys Cys Leu Asp Lys
  1               5

<210> SEQ ID NO 71
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 71

Thr Ala Thr Ser Leu Ala Asp
  1               5

<210> SEQ ID NO 72
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 72

Tyr Ala Thr Ser Leu Ala Asp
  1               5

<210> SEQ ID NO 73
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 73

Tyr Ala Thr Ser Leu Ala Asp
  1               5

<210> SEQ ID NO 74
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 74
```

Tyr Ala Thr Ser Leu Val His
  1               5

<210> SEQ ID NO 75
<211> LENGTH: 7
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 4
<223> OTHER INFORMATION: Unknown amino acid

<400> SEQUENCE: 75

Tyr Ala Asn Xaa Lys Ser Asp
  1               5

<210> SEQ ID NO 76
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 76

Glu Ala Ser Asn Leu Ala Gly
  1               5

<210> SEQ ID NO 77
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 77

Ser Ala Ser Ser Pro Ala Val
  1               5

<210> SEQ ID NO 78
<211> LENGTH: 7
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 1
<223> OTHER INFORMATION: Unknown amino acid

<400> SEQUENCE: 78

Xaa Gly Thr Ser Leu Ser Tyr
  1               5

<210> SEQ ID NO 79
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 79

Tyr Pro Ile Thr Leu Val Asn
  1               5

<210> SEQ ID NO 80
<211> LENGTH: 7

```
<212> TYPE: PRT
<213> ORGANISM: Artificial sequence
<220> FEATURE:
<223> OTHER INFORMATION: Sequence is synthesized.

<400> SEQUENCE: 80

Tyr Ala Thr Ser Leu Ala Asp
  1               5

<210> SEQ ID NO 81
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 81

Tyr Ala Thr Ser Leu Ala Asp
  1               5

<210> SEQ ID NO 82
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 82

Tyr Ala Thr Ser Leu Ala Asp
  1               5

<210> SEQ ID NO 83
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 83

Tyr Ala Thr Ser Leu Ala Asp
  1               5

<210> SEQ ID NO 84
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 84

Tyr Gly Ser Ser Leu Glu Asn
  1               5

<210> SEQ ID NO 85
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 85

Tyr Ala Thr Ser Leu Ala Asp
  1               5

<210> SEQ ID NO 86
<211> LENGTH: 9
<212> TYPE: PRT
<213> ORGANISM: Artificial sequence
```

```
<220> FEATURE:
<223> OTHER INFORMATION: Sequence is synthesized.

<400> SEQUENCE: 86

Leu Gln His Gly Glu Ser Pro Phe Thr
 1               5

<210> SEQ ID NO 87
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 87

Gln Gln His Gly Glu Tyr Gln Ser Thr
 1               5

<210> SEQ ID NO 88
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 88

Leu Gln His Gly Glu Ser Pro Phe Thr
 1               5

<210> SEQ ID NO 89
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 89

Gly Gln His Val Glu Arg Pro Tyr Ala
 1               5

<210> SEQ ID NO 90
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 90

Leu Gln His Gly Glu Ser Ser Phe Ile
 1               5

<210> SEQ ID NO 91
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 91

Leu Met His Gly Glu Ser Pro Phe Thr
 1               5

<210> SEQ ID NO 92
<211> LENGTH: 9
<212> TYPE: PRT
<213> ORGANISM: Artificial sequence
<220> FEATURE:
<223> OTHER INFORMATION: Sequence is synthesized.
```

<400> SEQUENCE: 92

Leu Gln His Gly Glu Ser Pro Phe Thr
 1               5

<210> SEQ ID NO 93
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 93

Leu Gln His Asp Glu Pro Gln Phe Thr
 1               5

<210> SEQ ID NO 94
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 94

Leu Gln Asn Val Gly Ser Pro Leu Thr
 1               5

<210> SEQ ID NO 95
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 95

Leu Gln His Gly Glu Ser Pro Phe Thr
 1               5

<210> SEQ ID NO 96
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 96

Leu Gln His Gly Glu Ser Pro Phe Thr
 1               5

<210> SEQ ID NO 97
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 97

Leu Gln Pro Arg His Gly Pro Phe Ile
 1               5

<210> SEQ ID NO 98
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 98

Leu Gln His Gly Glu Ser Pro Phe Thr
  1               5

<210> SEQ ID NO 99
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 99

Leu Gln His Gly Glu Ser Pro Phe Thr
  1               5

<210> SEQ ID NO 100
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 100

Leu Gln His Gly Glu Ser Pro Phe Thr
  1               5

<210> SEQ ID NO 101
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 101

Leu Gln Gln Gly Gly Arg His Leu Thr
  1               5

<210> SEQ ID NO 102
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 102

Leu His His Gly Ala Gly Thr Phe Thr
  1               5

<210> SEQ ID NO 103
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 103

Leu Gln His Gly Glu Ser Pro Phe Thr
  1               5

<210> SEQ ID NO 104
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 104

Pro Met His Arg Lys Ser Pro Ile Ser

```
<210> SEQ ID NO 105
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 105

Leu Gln His Gly Glu Ser Pro Phe Thr
 1               5

<210> SEQ ID NO 106
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 106

Gly Phe Asn Ile Lys Asp Tyr Tyr Met His
 1               5                  10

<210> SEQ ID NO 107
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 107

Gly Phe Asn Ile Lys Asp Tyr Tyr Met His
 1               5                  10

<210> SEQ ID NO 108
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 108

Gly Phe Asn Ile Lys Asp Tyr Tyr Met His
 1               5                  10

<210> SEQ ID NO 109
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 109

Gly Phe Asn Ile Lys Asp Tyr Tyr Met His
 1               5                  10

<210> SEQ ID NO 110
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 110

Gly Phe Asn Ile Lys Asp Tyr Tyr Met His
 1               5                  10
```

```
<210> SEQ ID NO 111
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 7
<223> OTHER INFORMATION: Unknown amino acid

<400> SEQUENCE: 111

Gly Phe Asn Ile Arg Lys Xaa Ser Leu Leu
 1               5                  10

<210> SEQ ID NO 112
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 8
<223> OTHER INFORMATION: Unknown amino acid

<400> SEQUENCE: 112

Cys Phe Asn Ser Lys Ala Gly Xaa Thr Pro
 1               5                  10

<210> SEQ ID NO 113
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 113

Gly Phe Asn Ile Lys Asp Tyr Tyr Met His
 1               5                  10

<210> SEQ ID NO 114
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 114

Gly Phe Asn Ile Lys Asp Tyr Tyr Met His
 1               5                  10

<210> SEQ ID NO 115
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 6
<223> OTHER INFORMATION: Unknown amino acid

<400> SEQUENCE: 115

Gly Phe His Ile Lys Xaa Tyr Tyr Met Asn
 1               5                  10

<210> SEQ ID NO 116
<211> LENGTH: 10
```

```
<212> TYPE: PRT
<213> ORGANISM: Artificial sequence
<220> FEATURE:
<223> OTHER INFORMATION: Sequence is synthesized.

<400> SEQUENCE: 116

Gly Phe Asn Ile Lys Asp Tyr Tyr Met His
1               5                   10

<210> SEQ ID NO 117
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 117

Gly Phe Asn Ile Lys Asp Tyr Tyr Met His
1               5                   10

<210> SEQ ID NO 118
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 5
<223> OTHER INFORMATION: Unknown amino acid

<400> SEQUENCE: 118

Gly Phe Pro Asn Xaa Gly Tyr Tyr Lys Pro
1               5                   10

<210> SEQ ID NO 119
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 119

Asp Leu Asn Ile Lys Tyr Asp Tyr Ile Pro
1               5                   10

<210> SEQ ID NO 120
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 120

Gly Phe Asn Ile Lys Asp Tyr Tyr Met His
1               5                   10

<210> SEQ ID NO 121
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 121

Gly Phe Asn Val Asp Tyr Tyr Tyr Val Leu
1               5                   10
```

```
<210> SEQ ID NO 122
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 122

Gly Phe Ser Ile Thr Asn Tyr Tyr Met His
 1               5                  10

<210> SEQ ID NO 123
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 123

Gly Phe Asn Ile Lys Asp Tyr Tyr Met His
 1               5                  10

<210> SEQ ID NO 124
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 124

Gly Phe Asn Ile Lys Asp Tyr Tyr Met His
 1               5                  10

<210> SEQ ID NO 125
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 125

Gly Phe Asn Ile Lys Asp Tyr Tyr Met His
 1               5                  10

<210> SEQ ID NO 126
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 126

Gly Trp Ile Asp Pro Glu Asn Gly Asn Thr Ile Tyr Asp Pro Lys
 1               5                  10                  15

Phe Gln Asp

<210> SEQ ID NO 127
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 127

Gly Trp Ile Asp Pro Glu Asn Gly Asn Thr Ile Tyr Asp Pro Lys
 1               5                  10                  15

Phe Gln Asp
```

```
<210> SEQ ID NO 128
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 128

Gly Trp Ile Asp Pro Glu Asn Gly Asn Thr Ile Tyr Asp Pro Lys
 1               5                  10                  15

Phe Gln Asp

<210> SEQ ID NO 129
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 129

Gly Trp Ile Asp Pro Glu Asn Gly Asn Thr Ile Tyr Asp Pro Lys
 1               5                  10                  15

Phe Gln Asp

<210> SEQ ID NO 130
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 130

Gly Trp Ile Asp Pro Glu Asn Gly Asn Thr Ile Tyr Asp Pro Lys
 1               5                  10                  15

Phe Gln Asp

<210> SEQ ID NO 131
<211> LENGTH: 18
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 12, 17
<223> OTHER INFORMATION: Unknown amino acid

<400> SEQUENCE: 131

Gly Ser Asn Ala Pro Lys Gln Gly Tyr Pro Ser Xaa Asp Thr Lys
 1               5                  10                  15

Phe Xaa Asp

<210> SEQ ID NO 132
<211> LENGTH: 18
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 6
<223> OTHER INFORMATION: Unknown amino acid

<400> SEQUENCE: 132

Ser Trp Ile Asp Gln Xaa Asn Cys Asp Thr Asn Cys Glu Pro Asn
```

-continued

```
          1               5                  10                 15
Phe Leu Asp

<210> SEQ ID NO 133
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 133

Gly Trp Ile Asp Pro Glu Asn Gly Asn Thr Ile Tyr Asp Pro Lys
          1               5                  10                 15
Phe Gln Asp

<210> SEQ ID NO 134
<211> LENGTH: 18
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 2
<223> OTHER INFORMATION: Unknown amino acid

<400> SEQUENCE: 134

Gly Xaa Ile Asp Pro Val Lys Gly Asn Thr Ser Cys Asp Pro Tyr
          1               5                  10                 15
Leu Tyr Gly

<210> SEQ ID NO 135
<211> LENGTH: 18
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 6, 12
<223> OTHER INFORMATION: Unknown amino acid

<400> SEQUENCE: 135

Ser Trp Met Asp Ala Xaa Asn Gly Lys Thr Phe Xaa Asp Ser Ile
          1               5                  10                 15
Ser Gln Asn

<210> SEQ ID NO 136
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 136

Gly Trp Ile Asp Pro Glu Asn Gly Asp Thr Ile Tyr Asp Pro Lys
          1               5                  10                 15
Phe Gln Asp

<210> SEQ ID NO 137
<211> LENGTH: 18
<212> TYPE: PRT
<213> ORGANISM: Artificial sequence
<220> FEATURE:
<223> OTHER INFORMATION: Sequence is synthesized.
```

-continued

```
<400> SEQUENCE: 137

Ser Leu Ile Val Pro Lys Tyr Arg Asn Thr Leu Tyr Asp Ser Arg
1               5                   10                  15

Phe Gln His

<210> SEQ ID NO 138
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 138

Gly Trp Val His Ser Glu Ile Ala Lys Ala Ile His Asn Ser Ile
1               5                   10                  15

Arg Gln Val

<210> SEQ ID NO 139
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 139

Ser Trp Ser Val Arg Glu Ser Gly Thr Thr Ile Tyr Glu Thr Ile
1               5                   10                  15

Ala Gln Asp

<210> SEQ ID NO 140
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 140

Gly Trp Ile Asp Pro Glu Asn Gly Asn Thr Ile Tyr Asp Pro Lys
1               5                   10                  15

Phe Gln Asp

<210> SEQ ID NO 141
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 141

Gly Trp Ile Asp Pro Glu Asn Gly Asn Thr Ile Tyr Asp Pro Lys
1               5                   10                  15

Phe Gln Asp

<210> SEQ ID NO 142
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 142

Gly Trp Ile Asp Pro Glu Asn Gly Asn Thr Ile Tyr Asp Pro Lys
1               5                   10                  15
```

Leu His Asp

<210> SEQ ID NO 143
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 143

Gly Trp Ile Asp Pro Glu Asn Gly Asn Thr Ile Tyr Asp Pro Lys
 1               5                  10                  15

Phe Gln Asp

<210> SEQ ID NO 144
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 144

Gly Trp Ile Asp Pro Glu Asn Gly Asn Thr Ile Tyr Asp Pro Lys
 1               5                  10                  15

Phe Gln Asp

<210> SEQ ID NO 145
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 145

Gly Trp Ile Asp Pro Glu Asn Gly Asn Thr Ile Tyr Asp Pro Lys
 1               5                  10                  15

Phe Gln Asp

<210> SEQ ID NO 146
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 146

Arg Asp Thr Ala Ala Tyr Phe Asp Tyr
 1               5

<210> SEQ ID NO 147
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 147

Arg Asn Thr Ala Ala Tyr Phe Asp Tyr
 1               5

<210> SEQ ID NO 148
<211> LENGTH: 9
<212> TYPE: PRT
<213> ORGANISM: Artificial sequence
<220> FEATURE:
<223> OTHER INFORMATION: Sequence is synthesized.

```
<400> SEQUENCE: 148

Arg Asp Thr Ala Ala Tyr Phe Asp Tyr
 1               5

<210> SEQ ID NO 149
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 149

Arg Asp Thr Ala Ala Tyr Phe Asp Tyr
 1               5

<210> SEQ ID NO 150
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 150

Lys Ser Thr Leu Pro Asn Phe Val Tyr
 1               5

<210> SEQ ID NO 151
<211> LENGTH: 9
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Unknown amino acid

<400> SEQUENCE: 151

Arg Asp Thr Ala Glu Tyr Val Asp Xaa
 1               5

<210> SEQ ID NO 152
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 152

Lys Asp Ala Ala Ala Tyr Cys Gln Tyr
 1               5

<210> SEQ ID NO 153
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 153

Arg Asp Thr Ala Ala Tyr Phe Asp Tyr
 1               5

<210> SEQ ID NO 154
<211> LENGTH: 9
<212> TYPE: PRT
<213> ORGANISM: Artificial sequence
```

```
<220> FEATURE:
<223> OTHER INFORMATION: Sequence is synthesized.

<400> SEQUENCE: 154

Lys Asp Thr Glu Ala Phe Gly Glu Asn
 1               5

<210> SEQ ID NO 155
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 155

Arg His Thr Glu Ala Arg Phe Asp Tyr
 1               5

<210> SEQ ID NO 156
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 156

Arg Asp Thr Ala Ala Tyr Phe Asp Tyr
 1               5

<210> SEQ ID NO 157
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 157

Lys Glu Thr Ala Gly Phe His Ala Ser
 1               5

<210> SEQ ID NO 158
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 158

Arg Asp Ala Val Ala Asn Tyr Asp Cys
 1               5

<210> SEQ ID NO 159
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 159

Arg Asp Thr Ala Ala Val Tyr Cys Phe
 1               5

<210> SEQ ID NO 160
<211> LENGTH: 9
<212> TYPE: PRT
<213> ORGANISM: Artificial sequence
<220> FEATURE:
<223> OTHER INFORMATION: Sequence is synthesized.
```

```
<220> FEATURE:
<221> NAME/KEY: Xaa
<222> LOCATION: 6
<223> OTHER INFORMATION: Unknown amino acid

<400> SEQUENCE: 160

Arg Asp Ser Ser Ser Xaa Val Glu Asp
 1               5

<210> SEQ ID NO 161
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 161

Arg Asp Thr Ala Ala Tyr Phe Asp Tyr
 1               5

<210> SEQ ID NO 162
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 162

Arg Glu Thr Ala Ser Ile Val Glu Tyr
 1               5

<210> SEQ ID NO 163
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 163

Arg Asp Thr Ala Ala Tyr Phe Asp Tyr
 1               5

<210> SEQ ID NO 164
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 164

Arg Asp Thr Ala Ala Tyr Phe Asp Tyr
 1               5

<210> SEQ ID NO 165
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 165

Arg Asp Thr Ala Ala Tyr Phe Asp Tyr
 1               5

<210> SEQ ID NO 166
<211> LENGTH: 11
<212> TYPE: PRT
<213> ORGANISM: Artificial sequence
```

```
<220> FEATURE:
<223> OTHER INFORMATION: Sequence is synthesized.

<400> SEQUENCE: 166

Arg Ala Ser Lys Thr Ile Ser Lys Tyr Leu Ala
 1               5                  10

<210> SEQ ID NO 167
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 167

Arg Ala Ser Asn Thr Met Arg Lys Tyr Arg Ala
 1               5                  10

<210> SEQ ID NO 168
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 168

Pro Ala Ser Tyr Ser Ile Lys Thr Tyr Leu Arg
 1               5                  10

<210> SEQ ID NO 169
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 169

Arg Glu Gly Leu Arg Phe Ser Lys Asp Leu Ala
 1               5                  10

<210> SEQ ID NO 170
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 170

Arg Ala Ser Arg Ile Met Thr Lys Thr Ile Ser
 1               5                  10

<210> SEQ ID NO 171
<211> LENGTH: 11
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Unknown amino acid

<400> SEQUENCE: 171

Thr Ala Cys Thr Thr Leu Arg Glu Xaa Val Pro
 1               5                  10

<210> SEQ ID NO 172
<211> LENGTH: 11
```

```
<212> TYPE: PRT
<213> ORGANISM: Artificial sequence
<220> FEATURE:
<223> OTHER INFORMATION: Sequence is synthesized.

<400> SEQUENCE: 172

Tyr Glu Thr Lys Thr Ile Thr Thr Tyr Val Pro
 1               5                  10

<210> SEQ ID NO 173
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 173

Gly Ser Ile Lys Ser Ser Arg Gln Asn Leu Ala
 1               5                  10

<210> SEQ ID NO 174
<211> LENGTH: 11
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 2, 9
<223> OTHER INFORMATION: Unknown amino acid

<400> SEQUENCE: 174

Arg Xaa Ser Ser Thr Ile Trp Lys Xaa Leu Thr
 1               5                  10

<210> SEQ ID NO 175
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 175

Tyr Ala Ser Ile Thr Ile Ser Thr His Pro Ala
 1               5                  10

<210> SEQ ID NO 176
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 176

Leu Ala Ser Gln Pro Val Ser Arg Thr His Gly
 1               5                  10

<210> SEQ ID NO 177
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 177

Arg Ala Ser Lys Thr Ile Ser Lys Tyr Leu Ala
 1               5                  10
```

```
<210> SEQ ID NO 178
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 178

Arg Ala Asn Lys Ile Asn Arg Ile Ser Arg Ser
 1               5                  10

<210> SEQ ID NO 179
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 179

Arg Ala Ser Lys Ile Ile Ser Asn Asn Met Leu
 1               5                  10

<210> SEQ ID NO 180
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 180

Arg Thr Asn Arg Asn Ile Gly Lys Phe Pro Ala
 1               5                  10

<210> SEQ ID NO 181
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 181

Arg Ala Ser Lys Thr Ile Ser Ile Tyr Arg Ala
 1               5                  10

<210> SEQ ID NO 182
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 182

Gly Ala Ser Lys Thr Ile Ser Lys Tyr Leu Ala
 1               5                  10

<210> SEQ ID NO 183
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 183

Arg Ala Arg Gln Arg Met Ser Thr Tyr Leu Ala
 1               5                  10

<210> SEQ ID NO 184
<211> LENGTH: 11
```

```
<212> TYPE: PRT
<213> ORGANISM: Artificial sequence
<220> FEATURE:
<223> OTHER INFORMATION: sequence is synthesized
<220> FEATURE:
<221> NAME/KEY: Unsure
<222> LOCATION: 8
<223> OTHER INFORMATION: Unknown amino acid

<400> SEQUENCE: 184

Arg Ala Arg Glu Ala Phe Thr Xaa His Leu Ala
 1               5                  10

<210> SEQ ID NO 185
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 185

Leu Ala Arg Lys Thr Leu Ser Thr Asp Leu Ala
 1               5                  10

<210> SEQ ID NO 186
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 186

Arg Ala Ser Lys Thr Ile Ser Lys Tyr Leu Ala
 1               5                  10

<210> SEQ ID NO 187
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 187

Ser Gly Ser Thr Leu Gln Ser
 1               5

<210> SEQ ID NO 188
<211> LENGTH: 7
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 2
<223> OTHER INFORMATION: Unknown amino acid

<400> SEQUENCE: 188

Ser Xaa Arg Thr Leu Gln Ser
 1               5

<210> SEQ ID NO 189
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 189
```

Ser Gly Ser Thr Leu Gln Ser
1               5

<210> SEQ ID NO 190
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 190

Ser Gly Ser Thr Leu Gln Ser
1               5

<210> SEQ ID NO 191
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 191

Ile Gly Cys Met Val Pro Gly
1               5

<210> SEQ ID NO 192
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 192

Ser Ser Cys Thr Leu Gln Ser
1               5

<210> SEQ ID NO 193
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 193

Ser Gly Gly Ile Gln Gln Ser
1               5

<210> SEQ ID NO 194
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 194

Ser Ala Ser Thr Phe Gln Thr
1               5

<210> SEQ ID NO 195
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 195

Cys Gly Ser Thr Pro Gln Asn
1               5

```
<210> SEQ ID NO 196
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 196

Ser Asp Arg Pro Leu Leu Ser
1               5

<210> SEQ ID NO 197
<211> LENGTH: 7
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 6
<223> OTHER INFORMATION: Unknown amino acid

<400> SEQUENCE: 197

Ser Gly Ser Pro Leu Xaa Ser
1               5

<210> SEQ ID NO 198
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 198

Ser Gly Ser Thr Leu Gln Ser
1               5

<210> SEQ ID NO 199
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 199

Ser Gly Ser Thr Leu Gln Ser
1               5

<210> SEQ ID NO 200
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 200

Arg Ala Ile Arg Met His Thr
1               5

<210> SEQ ID NO 201
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 201
```

Ser Cys Trp Ser Pro Gln Ser
1               5

<210> SEQ ID NO 202
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 202

Ser Gly Ile Thr Leu Lys Ser
1               5

<210> SEQ ID NO 203
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 203

Ser Gly Ser Thr Leu Gln Ser
1               5

<210> SEQ ID NO 204
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 204

Ser Gly Ser Thr Leu Gln Ser
1               5

<210> SEQ ID NO 205
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 205

Ser Gly Ser Thr Leu Gln Ser
1               5

<210> SEQ ID NO 206
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 206

Ser Val Asp Ser Gln Glu Ser
1               5

<210> SEQ ID NO 207
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 207

Ser Gly Ser Thr Leu Gln Ser
1               5

<210> SEQ ID NO 208
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 208

Gln Gln His Asn Glu Tyr Pro Leu Thr
 1               5

<210> SEQ ID NO 209
<211> LENGTH: 9
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 2
<223> OTHER INFORMATION: Unknown amino acid

<400> SEQUENCE: 209

His Xaa His Asn Val Ser Leu Val Thr
 1               5

<210> SEQ ID NO 210
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 210

Gln Gln His Asn Glu Tyr Pro Leu Thr
 1               5

<210> SEQ ID NO 211
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 211

Gln Gln His Asn Glu Tyr Pro Leu Thr
 1               5

<210> SEQ ID NO 212
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 212

Gln Gln His Asn Glu Tyr Pro Leu Thr
 1               5

<210> SEQ ID NO 213
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 213

```
Gln Gln His Lys Glu Phe Pro Gln Thr
  1               5

<210> SEQ ID NO 214
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 214

Gln Leu Gln Asn Val Tyr Arg Leu Thr
  1               5

<210> SEQ ID NO 215
<211> LENGTH: 9
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 2, 6
<223> OTHER INFORMATION: Unknown amino acid

<400> SEQUENCE: 215

Gln Xaa Lys Ile Asp Xaa Pro Thr Thr
  1               5

<210> SEQ ID NO 216
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 216

Tyr Gln Cys Asn Asp Tyr Gln Ala Ser
  1               5

<210> SEQ ID NO 217
<211> LENGTH: 9
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 1, 6
<223> OTHER INFORMATION: Unknown amino acid

<400> SEQUENCE: 217

Xaa His Cys Asn Glu Xaa Ala Gln Arg
  1               5

<210> SEQ ID NO 218
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 218

Leu Arg Tyr Thr Pro Tyr Pro Leu Thr
  1               5

<210> SEQ ID NO 219
<211> LENGTH: 9
<212> TYPE: PRT
```

```
<213> ORGANISM: Artificial sequence
<220> FEATURE:
<223> OTHER INFORMATION: Sequence is synthesized.

<400> SEQUENCE: 219

Gln Gln His Asn Glu Tyr Pro Leu Thr
 1               5

<210> SEQ ID NO 220
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 220

Leu Gln Gln Lys Lys Glu Ser Glu Ile
 1               5

<210> SEQ ID NO 221
<211> LENGTH: 9
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 6
<223> OTHER INFORMATION: Unknown amino acid

<400> SEQUENCE: 221

Lys Arg His Asn Glu Xaa Leu Leu Thr
 1               5

<210> SEQ ID NO 222
<211> LENGTH: 9
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 3
<223> OTHER INFORMATION: Unknown amino acid

<400> SEQUENCE: 222

Gln Gln Xaa Ser Arg Tyr Pro Leu Ala
 1               5

<210> SEQ ID NO 223
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 223

His Lys His Asn Glu Tyr Pro Leu Thr
 1               5

<210> SEQ ID NO 224
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 224

Gln Gln His Asn Glu Tyr Pro Leu Thr
```

<210> SEQ ID NO 225
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 225

Gln Gln His Asn Glu Tyr Pro Leu Thr
 1               5

<210> SEQ ID NO 226
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 226

Gln Gln His Asn Glu Tyr Pro Leu Thr
 1               5

<210> SEQ ID NO 227
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 227

Pro Pro Thr Asn Glu Tyr Ala Leu Thr
 1               5

<210> SEQ ID NO 228
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 228

Gln Gln His Asn Glu Tyr Pro Leu Thr
 1               5

<210> SEQ ID NO 229
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 229

Gly Tyr Ser Phe Thr Gly His Trp Met Asn
 1               5                  10

<210> SEQ ID NO 230
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 230

Gly Phe Gly Phe Met Gly Leu Trp Gly Asn
 1               5                  10

```
<210> SEQ ID NO 231
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 231

Gly Tyr Ser Phe Thr Gly His Trp Met Asn
 1               5                  10

<210> SEQ ID NO 232
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 232

Gly Cys Asp Phe Asn Gly Pro Trp Leu Asn
 1               5                  10

<210> SEQ ID NO 233
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 233

Gly Tyr Ser Phe Thr Gly His Trp Met Asn
 1               5                  10

<210> SEQ ID NO 234
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 234

Gly Tyr Ser Phe Thr Gly His Trp Met Asn
 1               5                  10

<210> SEQ ID NO 235
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 8
<223> OTHER INFORMATION: Unknown amino acid

<400> SEQUENCE: 235

Gly Tyr Thr Tyr Thr Ser His Xaa Met Asn
 1               5                  10

<210> SEQ ID NO 236
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 236

Gly Tyr Ser Phe Thr Gly His Trp Met Asn
```

```
                1               5                   10
```

<210> SEQ ID NO 237
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 237

```
Gly Tyr Ile Ser Thr Gly Pro Trp Met Asp
 1               5                   10
```

<210> SEQ ID NO 238
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 238

```
Val Glu Ala Leu His Arg Ser Leu Asp Glu
 1               5                   10
```

<210> SEQ ID NO 239
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 239

```
Gly Tyr Gly Tyr Thr Arg Thr Gly Lys Ser
 1               5                   10
```

<210> SEQ ID NO 240
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 240

```
Asp Asp Cys Leu Ser Gly His Trp Thr Asn
 1               5                   10
```

<210> SEQ ID NO 241
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 241

```
Gly Tyr Ser Phe Thr Gly His Trp Met Asn
 1               5                   10
```

<210> SEQ ID NO 242
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 242

```
Gly Phe Thr Phe Pro Leu His Trp Met Asn
 1               5                   10
```

<210> SEQ ID NO 243
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 243

Gly Tyr Ser Phe Thr Gly His Trp Met Asn
1               5                   10

<210> SEQ ID NO 244
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 8
<223> OTHER INFORMATION: Unknown amino acid

<400> SEQUENCE: 244

Gly Tyr Ser Phe Ser Gly Tyr Xaa Met Tyr
1               5                   10

<210> SEQ ID NO 245
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 245

Gly Tyr Ser Phe Thr Gly His Trp Met Asn
1               5                   10

<210> SEQ ID NO 246
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 246

Gly Met Ile His Pro Ser Asp Ser Glu Thr Arg Leu Asn Gln Lys
1               5                   10                  15

Phe Lys Asp

<210> SEQ ID NO 247
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 247

Gly Met Ile His Pro Ser Asp Ser Glu Thr Arg Leu Asn Gln Lys
1               5                   10                  15

Phe Lys Asp

<210> SEQ ID NO 248
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 248

Gly Met Ile His Pro Ser Asp Ser Glu Thr Arg Leu Asn Gln Lys
 1               5                  10                  15

Phe Lys Asp

<210> SEQ ID NO 249
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 249

Gly Met Ile His Pro Ser Asp Ser Glu Thr Arg Leu Asn Gln Lys
 1               5                  10                  15

Phe Lys Asp

<210> SEQ ID NO 250
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 250

Gly Met Ile His Pro Ser Asp Ser Glu Thr Arg Leu Asn Gln Lys
 1               5                  10                  15

Phe Lys Asp

<210> SEQ ID NO 251
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 251

Gly Met Ile His Pro Ser Asp Ser Glu Thr Arg Leu Asn Gln Lys
 1               5                  10                  15

Phe Lys Asp

<210> SEQ ID NO 252
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 252

Ser Met Ile His Leu Ser Asp Thr Glu Ser Arg Leu Asn His Lys
 1               5                  10                  15

Phe Lys Val

<210> SEQ ID NO 253
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 253

Gly Met Ile His Pro Ser Asp Ser Glu Thr Arg Leu Asn Gln Lys
 1               5                  10                  15

Phe Lys Asp

<210> SEQ ID NO 254
<211> LENGTH: 18
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Unknown amino acid

<400> SEQUENCE: 254

Ser Ile Phe Thr Leu Arg Val Ser Xaa Ser Gly Lys Asn Gln Lys
 1               5                  10                  15

Phe Met Glu

<210> SEQ ID NO 255
<211> LENGTH: 18
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 8
<223> OTHER INFORMATION: Unknown amino acid

<400> SEQUENCE: 255

Trp Arg Asp Pro Pro Glu Arg Xaa Leu Phe Pro Ser Glu Ser Val
 1               5                  10                  15

Ile Gln Arg

<210> SEQ ID NO 256
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 256

Gly Met Ile His Pro Ser Asp Ser Glu Thr Arg Leu Asn Gln Lys
 1               5                  10                  15

Phe Lys Asp

<210> SEQ ID NO 257
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 257

Gly Arg Ile Gln Pro Ser Asp Tyr Val Thr Arg Leu Lys Pro Gly
 1               5                  10                  15

Phe Gln Asp

<210> SEQ ID NO 258
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 258

Gly Met Ile His Pro Ser Asp Ser Glu Thr Arg Leu Asn Gln Lys
 1               5                  10                  15

Phe Lys Asp

<210> SEQ ID NO 259
<211> LENGTH: 18
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 17
<223> OTHER INFORMATION: Unknown amino acid

<400> SEQUENCE: 259

Thr Ser Ser Ser Leu Pro Ile Glu Lys Pro Val Trp Thr Ile Asn
 1               5                  10                  15

Phe Xaa Asn

<210> SEQ ID NO 260
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 260

Gly Met Ile His Pro Ser Asp Ser Glu Ser Arg Leu Lys Gln Asn
 1               5                  10                  15

Ile Ile Asp

<210> SEQ ID NO 261
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 261

Ser Met Ile Leu Arg Ser Ala Ser Asp Thr Arg Met Asn Asn Thr
 1               5                  10                  15

Phe Lys Glu

<210> SEQ ID NO 262
<211> LENGTH: 18
<212> TYPE: PRT
<213> ORGANISM: Artificial sequence
<220> FEATURE:
<223> OTHER INFORMATION: Sequence is synthesized.

<400> SEQUENCE: 262

Gly Met Ile His Pro Ser Asp Ser Glu Thr Arg Leu Asn Gln Lys
 1               5                  10                  15

Phe Lys Asp

<210> SEQ ID NO 263
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 263

Arg Gly Ile Tyr Phe Tyr Gly Thr Thr Tyr Phe Asp Tyr
 1               5                   10

<210> SEQ ID NO 264
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 264

Arg Gly Ile Tyr Phe Tyr Gly Thr Thr Tyr Phe Asp Tyr
 1               5                   10

<210> SEQ ID NO 265
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 265

Arg Gly Ile Tyr Phe Tyr Gly Thr Thr Tyr Phe Asp Tyr
 1               5                   10

<210> SEQ ID NO 266
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 266

Arg Gly Ile Tyr Ser Tyr Glu Thr Phe Thr Val Gly Tyr
 1               5                   10

<210> SEQ ID NO 267
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 267

Arg Gly Ile Tyr Phe Tyr Gly Thr Thr Tyr Phe Asp Tyr
 1               5                   10

<210> SEQ ID NO 268
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 268

Arg Gly Phe His Leu Tyr Gly Arg Thr Leu Ile Asp Tyr
 1               5                   10

<210> SEQ ID NO 269
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 269

Arg Gly Ile Tyr Phe Tyr Gly Thr Thr Tyr Phe Asp Tyr
 1               5                   10

<210> SEQ ID NO 270
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 270

Arg Gly Ile Tyr Phe Tyr Gly Thr Thr Tyr Phe Asp Tyr
1               5                   10

<210> SEQ ID NO 271
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 271

Arg Gly Ile Tyr Phe Tyr Gly Thr Thr Tyr Phe Asp Tyr
1               5                   10

<210> SEQ ID NO 272
<211> LENGTH: 13
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 10
<223> OTHER INFORMATION: Unknown amino acid

<400> SEQUENCE: 272

Arg Gly Asn Asp Leu Tyr Cys Thr Thr Xaa Phe Asp His
1               5                   10

<210> SEQ ID NO 273
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 273

Arg Gly Ile Tyr Phe Tyr Gly Thr Thr Tyr Phe Asp Tyr
1               5                   10

<210> SEQ ID NO 274
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 274

Arg Gly Ile Tyr Phe Tyr Gly Thr Thr Tyr Phe Asp Tyr
1               5                   10

<210> SEQ ID NO 275
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 275

-continued

Arg Gly Ile Tyr Phe Tyr Gly Thr Thr Tyr Phe Asp Tyr
1               5                   10

<210> SEQ ID NO 276
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 276

Arg Gly Ile Tyr Phe Tyr Gly Thr Thr Tyr Phe Asn Cys
1               5                   10

<210> SEQ ID NO 277
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 277

Lys Gly Arg Tyr Asp Asn Ser Pro Thr Tyr Cys Asp Tyr
1               5                   10

<210> SEQ ID NO 278
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 278

Arg Gly Ile Tyr Phe Tyr Gly Thr Thr Tyr Phe Asp Tyr
1               5                   10

<210> SEQ ID NO 279
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 279

Lys Ala Ser Gln Ser Val Asp Tyr Asp Gly Asp Ser Tyr Met Asn
1               5                   10                  15

<210> SEQ ID NO 280
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 280

Lys Ala Ser Arg Arg Val Asp Phe Tyr Asn Ile Ser Tyr Arg Lys
1               5                   10                  15

<210> SEQ ID NO 281
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 281

Pro Ala Ser His Asn Val Ile Cys Asp Gly Phe Ile Tyr Leu Tyr
1               5                   10                  15

```
<210> SEQ ID NO 282
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 282

Lys Ala Ser Gln Ser Val Asp Tyr Asp Gly Asp Ser Tyr Met Asn
 1               5                  10                  15

<210> SEQ ID NO 283
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 283

Lys Ala Ser Gln Ser Val Asp Tyr Asp Gly Asp Ser Tyr Met Asn
 1               5                  10                  15

<210> SEQ ID NO 284
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 284

Thr Val Ser Thr Ile Leu Asp Asp Val Gly Asp Asn Tyr Ile Ile
 1               5                  10                  15

<210> SEQ ID NO 285
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 285

Lys Ala Ser Gln Ser Val Asp Tyr Asp Gly Asp Ser Tyr Met Asn
 1               5                  10                  15

<210> SEQ ID NO 286
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 286

Lys Ala Ser Gln Ser Val Asp Tyr Asp Gly Asp Ser Tyr Met Asn
 1               5                  10                  15

<210> SEQ ID NO 287
<211> LENGTH: 15
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 4
<223> OTHER INFORMATION: Unknown amino acid

<400> SEQUENCE: 287
```

Ile Thr Ser Xaa Thr Val Val Tyr Asp Gly Tyr Ser Val Leu Leu
1               5                   10                  15

<210> SEQ ID NO 288
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 288

Ile Asp Ile Leu Ser Val Asp Tyr Asp Gly Asp Ser Tyr Met Asn
1               5                   10                  15

<210> SEQ ID NO 289
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 289

Lys Ala Ser Gln Ser Val Asp Tyr Asp Gly Asp Ser Tyr Met Asn
1               5                   10                  15

<210> SEQ ID NO 290
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 290

Lys Ala Ser Gln Ser Val Asp Tyr Asp Gly Asp Ser Tyr Met Asn
1               5                   10                  15

<210> SEQ ID NO 291
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 291

Lys Ala Ser Gln Ser Val Asp Tyr Asp Gly Asp Ser Tyr Met Asn
1               5                   10                  15

<210> SEQ ID NO 292
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 292

Asp Val Cys Gln Arg Val Asp Lys Leu Gly Asp Ile Asp Ser His
1               5                   10                  15

<210> SEQ ID NO 293
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 293

Lys Ser Arg Gln Ser Val Asp Gly Lys Gly Gly Asn Tyr Ile Asn
1               5                   10                  15

```
<210> SEQ ID NO 294
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 294

Lys Ala Ser Gln Ser Gly Asp Tyr Asp Gly Asp Ser Tyr Met Asn
 1               5                  10                  15

<210> SEQ ID NO 295
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 295

Lys Ala Ser Gln Ser Val Asp Tyr Asp Gly Asp Ser Tyr Met Asn
 1               5                  10                  15

<210> SEQ ID NO 296
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 296

Lys Ala Ser Gln Ser Val Asp Tyr Asp Gly Asp Ser Tyr Met Asn
 1               5                  10                  15

<210> SEQ ID NO 297
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 297

Ala Ala Ser Tyr Leu Gly Ser
 1               5

<210> SEQ ID NO 298
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 298

Ala Ala Ser Tyr Leu Gly Ser
 1               5

<210> SEQ ID NO 299
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 299

Ala Val Leu Tyr Leu Val Ser
 1               5
```

```
<210> SEQ ID NO 300
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 300

Ser Ala Arg His Leu Gly Thr
1               5

<210> SEQ ID NO 301
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 301

Ala Ala Ser Tyr Leu Gly Ser
1               5

<210> SEQ ID NO 302
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 302

Met Gly Ser Tyr Arg Gly Arg
1               5

<210> SEQ ID NO 303
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 303

Ser Gly Leu Tyr Leu Gly Ser
1               5

<210> SEQ ID NO 304
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 304

Ala Ala Ser Tyr Leu Gly Ser
1               5

<210> SEQ ID NO 305
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 305

Ala Ala Ser Tyr Leu Gly Ser
1               5

<210> SEQ ID NO 306
<211> LENGTH: 7
```

```
<212> TYPE: PRT
<213> ORGANISM: Artificial sequence
<220> FEATURE:
<223> OTHER INFORMATION: Sequence is synthesized.

<400> SEQUENCE: 306

Ala Ala Ser Tyr Leu Gly Ser
 1               5

<210> SEQ ID NO 307
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 307

Ala Ala Ser Tyr Leu Gly Ser
 1               5

<210> SEQ ID NO 308
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 308

Ala Ala Ser Tyr Leu Gly Ser
 1               5

<210> SEQ ID NO 309
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 309

Ala Ala Ser Tyr Leu Gly Ser
 1               5

<210> SEQ ID NO 310
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 310

Ala Ser Ser Tyr Leu Gly Ser
 1               5

<210> SEQ ID NO 311
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 311

Ala Ala Ser Tyr Leu Gly Ser
 1               5

<210> SEQ ID NO 312
<211> LENGTH: 7
<212> TYPE: PRT
<213> ORGANISM: Artificial sequence
```

```
<220> FEATURE:
<223> OTHER INFORMATION: Sequence is synthesized.

<400> SEQUENCE: 312

Ala Ala Ser Tyr Leu Gly Ser
 1               5

<210> SEQ ID NO 313
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 313

Ala Ala Ser Tyr Leu Gly Ser
 1               5

<210> SEQ ID NO 314
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 314

Ala Ala Ser Tyr Leu Gly Ser
 1               5

<210> SEQ ID NO 315
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 315

Gln Gln Ser His Glu Asp Pro Tyr Thr
 1               5

<210> SEQ ID NO 316
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 316

Gln Gln Ser His Glu Asp Pro Tyr Thr
 1               5

<210> SEQ ID NO 317
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 317

Asp Gln Ser Gln Val Tyr Pro Tyr Thr
 1               5

<210> SEQ ID NO 318
<211> LENGTH: 9
<212> TYPE: PRT
<213> ORGANISM: Artificial sequence
<220> FEATURE:
<223> OTHER INFORMATION: Sequence is synthesized.
```

```
<400> SEQUENCE: 318

Gln Gln Ser His Glu Glu Ala Tyr Thr
 1               5

<210> SEQ ID NO 319
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 319

Gln Gln Ser His Glu Asp Pro Tyr Thr
 1               5

<210> SEQ ID NO 320
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 320

Gln Gln Ser His Glu Asp Pro Tyr Thr
 1               5

<210> SEQ ID NO 321
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 321

His Leu Ser His Gly Gly Pro Asn Thr
 1               5

<210> SEQ ID NO 322
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 322

Gln Gln Ser His Glu Asp Pro Tyr Thr
 1               5

<210> SEQ ID NO 323
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 323

Gln Gln Ser His Glu Asp Pro Tyr Thr
 1               5

<210> SEQ ID NO 324
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 324
```

Gln Gln Ser His Glu Asp Pro Tyr Thr
  1               5

<210> SEQ ID NO 325
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 325

Gln Gln Ser Gln Val Glu Ile Tyr Thr
  1               5

<210> SEQ ID NO 326
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 326

Gln Gln Ser His Glu Asp Pro Tyr Thr
  1               5

<210> SEQ ID NO 327
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 327

Gln Gln Ser His Glu Asp Pro Tyr Thr
  1               5

<210> SEQ ID NO 328
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 328

Gln Gln Ser His Glu Asp Pro Tyr Thr
  1               5

<210> SEQ ID NO 329
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 329

Gln Gln Ser His Glu Asp Pro Tyr Thr
  1               5

<210> SEQ ID NO 330
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 330

Gln Gln Ser His Lys Asp Pro Tyr Pro

<210> SEQ ID NO 331
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 331

Gln Gln Ser His Glu Asp Pro Tyr Asn
1               5

<210> SEQ ID NO 332
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 332

Gln Gln Ser His Glu Asp Pro Tyr Thr
1               5

<210> SEQ ID NO 333
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 333

Gly Tyr Ser Ile Thr Ser Gly Tyr Ser Trp Asn
1               5                   10

<210> SEQ ID NO 334
<211> LENGTH: 11
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 2
<223> OTHER INFORMATION: Unknown amino acid

<400> SEQUENCE: 334

Gly Xaa Ser Leu Thr Ser Ser Glu Cys Met Ser
1               5                   10

<210> SEQ ID NO 335
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 335

Gly Tyr Ser Ile Thr Ser Gly Tyr Ser Trp Asn
1               5                   10

<210> SEQ ID NO 336
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 336

Gly Tyr Ser Ile Thr Ser Gly Tyr Ser Trp Asn
1               5                   10

<210> SEQ ID NO 337
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 337

Gly Tyr Ser Ile Thr Ser Gly Tyr Ser Trp Asn
1               5                   10

<210> SEQ ID NO 338
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 338

Gly Tyr Ser Ile Thr Ser Gly Tyr Ser Trp Asn
1               5                   10

<210> SEQ ID NO 339
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 339

Val Ser Tyr Phe Thr Arg Asp Ser Cys Trp Asn
1               5                   10

<210> SEQ ID NO 340
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 340

Gly Cys Trp Ile Phe Ser Gly Tyr Arg Trp Ile
1               5                   10

<210> SEQ ID NO 341
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 341

Gly Tyr Ser Ile Thr Ser Gly Tyr Ser Trp Asn
1               5                   10

<210> SEQ ID NO 342
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 342

Gly Tyr Ser Ile Thr Ser Gly Tyr Ser Trp Asn

```
<210> SEQ ID NO 343
<211> LENGTH: 11
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Unknown amino acid

<400> SEQUENCE: 343

Gly Tyr Cys Ile Tyr Thr Gly Tyr Xaa Ile Asn
 1               5                  10

<210> SEQ ID NO 344
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 344

Gly Tyr Ser Ile Thr Ser Gly Tyr Ser Trp Asn
 1               5                  10

<210> SEQ ID NO 345
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 345

Cys Ser Gly Leu Ala Asp Gly Tyr Cys Ile His
 1               5                  10

<210> SEQ ID NO 346
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 346

Gly Tyr Ser Ile Thr Ser Gly Tyr Ser Trp Asn
 1               5                  10

<210> SEQ ID NO 347
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 347

Gly Tyr Phe Ile Thr Asn Gly Asp Cys Trp Asn
 1               5                  10

<210> SEQ ID NO 348
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 348
```

Gly Tyr Ser Ile Thr Ser Gly Tyr Ser Trp Asn
 1               5                   10

<210> SEQ ID NO 349
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 349

Gly Tyr Ser Ile Thr Ser Gly Tyr Ser Trp Asn
 1               5                   10

<210> SEQ ID NO 350
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 350

Gly Tyr Ser Ile Thr Ser Gly Tyr Ser Trp Asn
 1               5                   10

<210> SEQ ID NO 351
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 351

Gly Ser Ile Thr Tyr Asp Gly Ser Ser Asn Tyr Asn Pro Ser Leu
 1               5                   10                  15

Lys Asn

<210> SEQ ID NO 352
<211> LENGTH: 17
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 5
<223> OTHER INFORMATION: Unknown amino acid

<400> SEQUENCE: 352

Gly Ser Ser Tyr Xaa Asp Ala Tyr Ser Asp Tyr Ile Lys Ser Leu
 1               5                   10                  15

Leu Asn

<210> SEQ ID NO 353
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 353

Gly Ser Ile Thr Tyr Asp Gly Ser Ser Asn Tyr Asn Pro Ser Leu
 1               5                   10                  15

Lys Asn

```
<210> SEQ ID NO 354
<211> LENGTH: 17
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 5, 11
<223> OTHER INFORMATION: Unknown amino acid

<400> SEQUENCE: 354

Gly Ser Val Ile Xaa Val Ser Ser Ser Xaa Asn Leu Ser Arg
  1               5                  10                  15

Arg Asn

<210> SEQ ID NO 355
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 355

Gly Ser Ile Thr Tyr Asp Gly Ser Ser Asn Tyr Asn Pro Ser Leu
  1               5                  10                  15

Lys Asn

<210> SEQ ID NO 356
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 356

Gly Ser Ile Thr Tyr Asp Gly Ser Ser Asn Tyr Asn Pro Ser Leu
  1               5                  10                  15

Lys Asn

<210> SEQ ID NO 357
<211> LENGTH: 17
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 11
<223> OTHER INFORMATION: Unknown amino acid

<400> SEQUENCE: 357

Ser Val Ile Thr Cys Tyr Arg Ser Ser Ser Xaa Asn Trp Ser Leu
  1               5                  10                  15

Lys Asn

<210> SEQ ID NO 358
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 358

Ser Gly Glu Arg Phe Pro Leu Arg Ile Asn Tyr Asn Pro Gly Leu
  1               5                  10                  15
```

Lys Tyr

<210> SEQ ID NO 359
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 359

Gly Ser Ile Thr Tyr Asp Gly Ser Ser Asn Tyr Asn Pro Ser Leu
 1               5                  10                  15

Lys Asn

<210> SEQ ID NO 360
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 360

Gly Arg Val Thr Phe Ala Gly Ser Val Asn Phe Asp Pro Ser Leu
 1               5                  10                  15

Lys Asn

<210> SEQ ID NO 361
<211> LENGTH: 17
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 10
<223> OTHER INFORMATION: Unknown amino acid

<400> SEQUENCE: 361

Gly Cys Ile Thr Tyr Asp Gly Arg Ser Xaa His Asn Gln Ser Pro
 1               5                  10                  15

Lys Asn

<210> SEQ ID NO 362
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 362

Gly Ser Ile Thr Tyr Asp Gly Ser Ser Asn Tyr Asn Pro Ser Leu
 1               5                  10                  15

Lys Asn

<210> SEQ ID NO 363
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 363

Ser Trp His Pro Tyr Ala Cys Ser Arg Asn Tyr Asn Leu Ser Leu
 1               5                  10                  15

Lys Tyr

<210> SEQ ID NO 364
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 364

Gly Ser Ile Thr Tyr Asp Gly Ser Ser Asn Tyr Asn Pro Ser Leu
 1               5                  10                  15

Lys Asn

<210> SEQ ID NO 365
<211> LENGTH: 17
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 11
<223> OTHER INFORMATION: Unknown amino acid

<400> SEQUENCE: 365

Gly Thr Ile Ser His Glu Asp Gly Ser Asp Xaa Asn Pro Ser Pro
 1               5                  10                  15

Lys Asn

<210> SEQ ID NO 366
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 366

Gly Ser Ile Thr Tyr Asp Gly Ser Ser Asn Tyr Asn Pro Ser Leu
 1               5                  10                  15

Lys Asn

<210> SEQ ID NO 367
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 367

Gly Ser Ile Thr Tyr Asp Gly Ser Ser Asn Tyr Asn Pro Ser Leu
 1               5                  10                  15

Lys Asn

<210> SEQ ID NO 368
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 368

Gly Ser Ile Thr Tyr Asp Gly Ser Ser Asn Tyr Asn Pro Ser Leu
 1               5                  10                  15

Lys Asn

```
<210> SEQ ID NO 369
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 369

Arg Gly Ser His Tyr Phe Gly His Trp His Phe Ala Val
 1               5                  10

<210> SEQ ID NO 370
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 370

Arg Gly Ser His Tyr Phe Gly His Trp His Phe Ala Val
 1               5                  10

<210> SEQ ID NO 371
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 371

Arg Gly Ser His Tyr Phe Gly His Trp His Phe Ala Val
 1               5                  10

<210> SEQ ID NO 372
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 372

Lys Gly Ser His Tyr Phe Ser Glu Ser His Phe Ala Val
 1               5                  10

<210> SEQ ID NO 373
<211> LENGTH: 13
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 5
<223> OTHER INFORMATION: Unknown amino acid

<400> SEQUENCE: 373

Lys Gly Arg His Xaa Val Gly Arg Trp Asp Phe Thr Ile
 1               5                  10

<210> SEQ ID NO 374
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 374

Arg Gly Ser His Tyr Phe Gly His Trp His Phe Ala Val
```

```
                    1               5                   10

<210> SEQ ID NO 375
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 375

Lys Gly Ser His Tyr Phe Ser His Trp Pro Phe Pro Val
  1               5                   10

<210> SEQ ID NO 376
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 376

Arg Gly Arg His His Leu Ala Ile Arg Asn Phe Ala Gly
  1               5                   10

<210> SEQ ID NO 377
<211> LENGTH: 13
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Unknown amino acid

<400> SEQUENCE: 377

Arg Gly Ser Arg Cys Cys Ser Tyr Xaa His Phe Ala Ser
  1               5                   10

<210> SEQ ID NO 378
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 378

Arg Gly Arg Asp Asn Phe Val Asn Trp His Val Ser Val
  1               5                   10

<210> SEQ ID NO 379
<211> LENGTH: 13
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 9
<223> OTHER INFORMATION: Unknown amino acid

<400> SEQUENCE: 379

Arg Gly Cys Leu His Tyr His Arg Xaa His Phe Ala Val
  1               5                   10

<210> SEQ ID NO 380
<211> LENGTH: 13
<212> TYPE: PRT
<213> ORGANISM: Artificial sequence
```

```
<220> FEATURE:
<223> OTHER INFORMATION: Sequence is synthesized.
<220> FEATURE:
<221> NAME/KEY: Xaa
<222> LOCATION: 5
<223> OTHER INFORMATION: Unknown amino acid

<400> SEQUENCE: 380

Arg Gly Thr Asp Xaa Cys Gly His Arg Arg Phe Ala Phe
 1               5                  10

<210> SEQ ID NO 381
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 381

Arg Gly Gly Gln Tyr Leu Gly His Trp His Val Met Val
 1               5                  10

<210> SEQ ID NO 382
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 382

Arg Gly Ser His Tyr Phe Gly His Trp His Phe Ala Val
 1               5                  10

<210> SEQ ID NO 383
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 383

Arg Gly Ser His Tyr Phe Gly His Trp His Phe Ala Val
 1               5                  10

<210> SEQ ID NO 384
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 384

Arg Gly Ser His Tyr Phe Gly His Trp His Phe Ala Val
 1               5                  10

<210> SEQ ID NO 385
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 385

Arg Gly Ser His Tyr Phe Gly His Trp His Phe Ala Val
 1               5                  10

<210> SEQ ID NO 386
<211> LENGTH: 13
```

```
<212> TYPE: PRT
<213> ORGANISM: Artificial sequence
<220> FEATURE:
<223> OTHER INFORMATION: Sequence is synthesized.

<400> SEQUENCE: 386

Arg Gly Ser His Tyr Phe Gly His Trp His Phe Ala Val
 1               5                  10

<210> SEQ ID NO 387
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 387

Ala Ala Ser Gly Tyr Ser Ile Thr Ser Gly Tyr Ser Trp Asn Trp
 1               5                  10                  15

Val Arg

<210> SEQ ID NO 388
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 388

Ala Ala Ser Gly Tyr Ser Ile Ser Gly Gly Tyr His Leu Asn Trp
 1               5                  10                  15

Val Arg

<210> SEQ ID NO 389
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 389

Ala Ala Ser Gly Tyr Ser Ile Ser Gly Gly Tyr Arg Leu Asn Trp
 1               5                  10                  15

Val Arg

<210> SEQ ID NO 390
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 390

Ala Ala Ser Gly Tyr Ile Ile Thr Ser Gly Tyr Lys Leu Asn Trp
 1               5                  10                  15

Val Arg

<210> SEQ ID NO 391
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 391
```

Ala Ala Ser Gly Asn Ser Ile Thr Ser Gly Tyr Lys Leu Asn Trp
1               5                   10                  15

Val Arg

<210> SEQ ID NO 392
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 392

Ala Ala Ser Gly Tyr Ser Ile Thr Ser Gly His Lys Leu Asn Trp
1               5                   10                  15

Val Arg

<210> SEQ ID NO 393
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 393

Ala Ala Ser Gly Tyr Ser Ile Thr Ser Gly Tyr Lys Leu Asn Trp
1               5                   10                  15

Val Arg

<210> SEQ ID NO 394
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 394

Ala Ala Ser Gly Tyr Ser Ile Thr Ser Gly Tyr Lys Leu Asn Trp
1               5                   10                  15

Val Arg

<210> SEQ ID NO 395
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 395

Ala Ala Ser Gly Tyr Ser Ile Thr Ser Gly Tyr Lys Leu Asn Trp
1               5                   10                  15

Val Arg

<210> SEQ ID NO 396
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 396

Ala Ala Ser Gly Tyr Ser Ile Thr Ser Gly Tyr Lys Leu Asn Trp
1               5                   10                  15

Val Arg

<210> SEQ ID NO 397
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 397

Ala Ala Ser Gly Tyr Ser Ile Thr Ser Gly Tyr Asn Leu Asn Trp
1               5                   10                  15

Val Arg

<210> SEQ ID NO 398
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 398

Ala Ala Ser Gly Tyr Ser Ile Thr Ser Gly Tyr Ser Leu His Trp
1               5                   10                  15

Val Arg

<210> SEQ ID NO 399
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 399

Leu Leu Ile Tyr Ser Gly Ser Thr Leu Gln Ser Gly Val Pro Ser
1               5                   10                  15

<210> SEQ ID NO 400
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 400

Leu Leu Ile Tyr Ser Gly Ser Thr Leu Glu Ser Gly Val Pro Ser
1               5                   10                  15

<210> SEQ ID NO 401
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 401

Leu Leu Ile Tyr Ser Gly Ser Thr Leu Glu Ser Gly Val Pro Ser
1               5                   10                  15

<210> SEQ ID NO 402
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 402

Leu Leu Ile Tyr Thr Gly Ser Thr Leu Glu Ser Gly Val Pro Ser

-continued

<210> SEQ ID NO 403
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 403

Leu Leu Ile Tyr Ser Gly Ser Thr Leu Glu Ser Gly Val Pro Ser
 1               5                  10                  15

<210> SEQ ID NO 404
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 404

Leu Leu Ile Tyr Ser Gly Gly Thr Leu His Arg Gly Val Pro Ser
 1               5                  10                  15

<210> SEQ ID NO 405
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 405

Leu Leu Ile Tyr Ser Gly Tyr Ser Leu His Arg Gly Val Pro Ser
 1               5                  10                  15

<210> SEQ ID NO 406
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 406

Leu Leu Ile Tyr Ser Gly Arg Ala Met Gln Arg Gly Val Pro Ser
 1               5                  10                  15

<210> SEQ ID NO 407
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 407

Leu Leu Ile Tyr Ser Gly Arg Ala Leu Gln Ser Gly Val Pro Ser
 1               5                  10                  15

<210> SEQ ID NO 408
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 408

Leu Leu Ile Tyr Ser Gly Arg Ser Leu Gln Ser Gly Val Pro Ser
 1               5                  10                  15

<210> SEQ ID NO 409
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 409

Leu Leu Ile Tyr Asn Ala Arg Ser Leu Gln Ser Gly Val Pro Ser
 1               5                  10                  15

<210> SEQ ID NO 410
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 410

Leu Leu Ile Tyr Ser Gly Ser Ala Leu Gln Ser Gly Val Pro Ser
 1               5                  10                  15

<210> SEQ ID NO 411
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 411

Leu Leu Ile Tyr Ser Gly Ser Thr Leu Gln Ser Gly Val Pro Ser
 1               5                  10                  15

<210> SEQ ID NO 412
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 412

Leu Leu Ile Tyr Ser Gly Ser Ile Phe Gln Tyr Gly Val Pro Ser
 1               5                  10                  15

<210> SEQ ID NO 413
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 413

Leu Leu Ile Tyr Ser Gly Arg Thr Leu Trp Pro Gly Val Pro Ser
 1               5                  10                  15

<210> SEQ ID NO 414
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 414

Leu Leu Ile Tyr Ser Gly Arg Ser Leu Gln Arg Gly Val Pro Ser
 1               5                  10                  15

<210> SEQ ID NO 415

```
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 415

Ile Thr Cys Lys Ala Ser Arg Asp Ile Lys Ser Tyr Leu Ser Trp
 1               5                  10                  15

Tyr Gln

<210> SEQ ID NO 416
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 416

Ile Thr Cys Lys Gly Ser Gly Tyr Ile Lys His Phe Val Ser Trp
 1               5                  10                  15

Tyr Gln

<210> SEQ ID NO 417
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 417

Ile Thr Cys Lys Gly Ser Arg Asp Thr Thr Ser Phe Val Ser Trp
 1               5                  10                  15

Tyr Gln

<210> SEQ ID NO 418
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 418

Ile Thr Cys Asn Ala Ser Leu Val Ile Asn Arg Trp Leu Ser Trp
 1               5                  10                  15

Tyr Gln

<210> SEQ ID NO 419
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 419

Ile Thr Cys Lys Gly Gln Arg Val Leu Asn Ser Trp Leu Ser Trp
 1               5                  10                  15

Tyr Gln

<210> SEQ ID NO 420
<211> LENGTH: 17
<212> TYPE: PRT
<213> ORGANISM: Artificial sequence
<220> FEATURE:
<223> OTHER INFORMATION: Sequence is synthesized.
```

<400> SEQUENCE: 420

Ile Thr Cys Lys Ala Ser Arg Asp Ile Lys Ser Tyr Leu Ser Trp
1               5                   10                  15

Tyr Gln

<210> SEQ ID NO 421
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 421

Leu Ile Tyr Tyr Ala Thr Ser Leu Ala Asp Gly Val Pro
1               5                   10

<210> SEQ ID NO 422
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 422

Leu Ile Tyr Asp Ala Ile Gly Leu Ala Asp Gly Val Pro
1               5                   10

<210> SEQ ID NO 423
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 423

Leu Ile Tyr Tyr Ala Pro Gly Leu Ala Asp Gly Val Pro
1               5                   10

<210> SEQ ID NO 424
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 424

Leu Ile Tyr Tyr Ala Pro Ser Leu Ala Asp Gly Val Pro
1               5                   10

<210> SEQ ID NO 425
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 425

Leu Ile Tyr Tyr Ala Pro Gly Pro Ala Asp Gly Val Pro
1               5                   10

<210> SEQ ID NO 426
<211> LENGTH: 13
<212> TYPE: PRT
<213> ORGANISM: Artificial sequence
<220> FEATURE:
<223> OTHER INFORMATION: Sequence is synthesized.

```
<400> SEQUENCE: 426

Leu Ile Tyr Tyr Ala Pro Arg Arg Ala Arg Gly Val Pro
 1               5                  10

<210> SEQ ID NO 427
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 427

Leu Ile Tyr Tyr Glu Pro Gly Leu Ala Asp Gly Val Pro
 1               5                  10

<210> SEQ ID NO 428
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 428

Leu Ile Tyr Tyr Glu Ser Gly Pro Ala Asp Gly Val Pro
 1               5                  10

<210> SEQ ID NO 429
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 429

Leu Ile Tyr Tyr Ala Thr Gly Glu Thr Asp Gly Val Pro
 1               5                  10

<210> SEQ ID NO 430
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 430

Leu Ile Tyr Tyr Glu Thr Gly Trp Ala Glu Gly Val Pro
 1               5                  10

<210> SEQ ID NO 431
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 431

Leu Ile Tyr Tyr Glu Gly Ser Gly Lys Arg Gly Val Pro
 1               5                  10

<210> SEQ ID NO 432
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 432
```

Leu Ile Tyr Tyr Glu Thr Gly Glu Pro Glu Gly Val Pro
 1               5                   10

<210> SEQ ID NO 433
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 433

Leu Ile Tyr Tyr Glu Thr Gly Pro Thr Asp Gly Val Pro
 1               5                   10

<210> SEQ ID NO 434
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 434

Leu Ile Tyr Arg Gly Thr Ser Leu Phe Glu Gly Val Pro
 1               5                   10

<210> SEQ ID NO 435
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 435

Leu Ile Tyr Tyr Thr Ala Gly Pro Ser Asp Gly Val Pro
 1               5                   10

<210> SEQ ID NO 436
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 436

Leu Ile Tyr Tyr Thr Thr Gly Pro Val Asp Gly Val Pro
 1               5                   10

<210> SEQ ID NO 437
<211> LENGTH: 13
<212> TYPE: PRT
<213> ORGANISM: Artificial sequence
<220> FEATURE:
<223> OTHER INFORMATION: Sequence is synthesized.

<400> SEQUENCE: 437

Leu Ile Tyr Tyr Val Pro Trp Thr Ala Asp Gly Val Pro
 1               5                   10

<210> SEQ ID NO 438
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 438

Tyr Tyr Cys Leu Gln His Gly Glu Ser Pro Phe Thr Phe Gly Gln

-continued

```
 1               5                   10                  15

<210> SEQ ID NO 439
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 439

Tyr Tyr Cys Leu Gln Asp Gly Glu Ser Pro Phe Thr Phe Gly Gln
 1               5                   10                  15

<210> SEQ ID NO 440
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 440

Tyr Tyr Cys Leu Gln Asp Gly Glu Ser Pro Phe Thr Phe Gly Gln
 1               5                   10                  15

<210> SEQ ID NO 441
<211> LENGTH: 15
<212> TYPE: PRT
<213> ORGANISM: Artificial sequence
<220> FEATURE:
<223> OTHER INFORMATION: Sequence is synthesized.

<400> SEQUENCE: 441

Tyr Tyr Cys Leu Ser Asp Gly Ser Ser Pro Phe Thr Phe Gly Gln
 1               5                   10                  15
```

CDR-REPAIRED ANTIBODIES

This application is a continuation of U.S. application Ser. No. 11/061,841 filed on Feb. 18, 2005, now abandoned which is a non-provisional application claiming priority to provisional application No. 60/545,840 filed Feb. 19, 2004, the entire disclosures of which are hereby incorporated by reference.

FIELD OF THE INVENTION

The present invention concerns restoring antigen binding during humanization of antibodies through the selection of repaired hypervariable regions rather than through framework changes.

BACKGROUND OF THE INVENTION

Many potentially interesting monoclonal antibodies can rapidly be produced by the mouse immune system for biological study. In a clinical setting however, the use of these murine antibodies can result in a human anti-mouse antibody response (HAMA) thus negating their utility. A method to transfer the murine antigen binding information to a non-immunogenic human antibody acceptor, a process known as humanization, has resulted in many therapeutically useful drugs. The method of humanization generally begins by transferring all six murine complementarity determining regions (CDRs) onto a human antibody framework (Jones et al., Nature 321, 522-525 (1986)). These CDR-grafted antibodies generally do not retain their original affinity for antigen binding, and in fact, affinity is often severely impaired. Besides the CDRs, select non-human antibody framework residues must also be incorporated to maintain proper CDR conformation (Chothia et al., Nature 342:877 (1989)). The transfer of key mouse framework residues to the human acceptor in order to support the structural conformation of the grafted CDRs has been shown to restore antigen binding and affinity (Riechmann et al., Nature 332:323-327 (Mar. 24, 1988); Foote and Winter, J. Mol. Biol. 224:487-499 (1992); Presta et al., J. Immunol. 151, 2623-2632 (1993); Werther et al., J. Immunol. 157:4986-4995 (1996); and Presta et al., Thromb. Haemost. 85:379-389 (2001)). Many of the framework positions that are likely to affect affinity have been identified, thus structural modeling to select new residues in a stepwise fashion can generally lead to variants with restored antigen binding. Alternatively, phage antibody libraries targeted at these residues can also be used to enhance and speed up the affinity maturation process (Wu et al., J. Mol. Biol. 294:151-162 (1999) and Wu, H., Methods in Mol. Biol. 207: 197-212 (2003)).

Two approaches have been taken when choosing a starting human acceptor. One approach compares the sequence of the murine antibody to a list of known human antibody sequences in order to choose the human antibody most homologous to the murine antibody (Shearman et al., J. Immunol. 147:4366 (1991); Kettleborough et al., Protein Eng. 4, 773 (1991); Tempest et al., Biotechnology 9:266 (1991); Co et al, Proc. Natl. Acad. Sci. USA 88:2869 (1991); Routledge et al., Eur. J. Immunol. 21:2717 (1991)). This approach is designed to reduce the likelihood of disrupting the integrity of the CDRs upon grafting them onto the new human acceptor. A second approach utilizes a consensus human framework derived from human VL and VH subgroups. By choosing the most frequently used sequence as a acceptor, this approach has been shown to reduce the potential of an immunological response to the humanized antibody (Presta et al., J. Immunol. 151:2623-2632 (1993)). Following transfer of CDR residues into an acceptor chosen by either of these methods, it has been necessary to alter framework residues in the acceptor in order to restore and enhance antigen binding affinity.

Humanized anti-IgE, anti-CD 11 a and anti-tissue factor (TF) antibodies have been described in Presta et al., J. Immunol. 151, 2623-2632 (1993), Werther et al., J. Immunol. 157: 4986-4995 (1996), and Presta et al., Thromb. Haemost. 85:379389 (2001), respectively.

Patent publications describing humanized antibody variants include U.S. Pat. No. 6,407,213 and WO92/22653 (Carter and Presta), WO98/45332 (Wells et al.), WO98/45331 (Baca et al.), as well as US2003/0228663A1 and WO03/087131A2 (Lowman et al.).

US 2004/0162413, Watkins et al., published August, 2004 refers to methods of optimizing antibody variable region binding affinity. WO03/105782 A2, Rybak et al., published December 2003, references specificity grafting of a murine antibody onto a human framework.

SUMMARY OF THE INVENTION

Molecular interactions between hypervariable regions and the old framework are often lost upon grafting hypervariable regions onto a new framework, resulting in a perturbation of these hypervariable regions and a loss in antigen binding affinity. Rather than transferring murine residues that interact with the hypervariable region(s) to the new framework, the present application demonstrates that the molecular fit between the new framework and the grafted hypervariable region can be restored by changing residues residing within the hypervariable region(s). Utilizing a phage library designed to maintain a sequence bias towards the grafted hypervariable regions, mutations were introduced into all six hypervariable regions and clones with high antigen binding affinity, but lacking any framework changes, were selected. In this application, it is demonstrated that high affinity binding can rapidly be restored through slight modifications to murine hypervariable regions grafted to a human acceptor without any changes to framework residues.

Accordingly, in a first aspect, the invention concerns an altered antibody which binds an antigen with a binding affinity ($K_d$) value of no more than about $5 \times 10^{-7}$ M, the altered antibody comprising variable heavy (VH) and variable light (VL) acceptor human frameworks and one or more altered hypervariable regions derived from a non-human antibody which binds the antigen, wherein the VH and VL frameworks lack human to non-human amino acid substitutions therein.

Various forms of the altered antibody are contemplated herein. For example, the altered antibody may be an intact antibody (e.g. a human IgG1 antibody) or an antibody fragment (e.g. a Fab or F(ab')$_2$). Furthermore, the altered antibody may be labeled with a detectable label, immobilized on a solid phase and/or conjugated with a heterologous compound (such as a cytotoxic agent).

Diagnostic uses for the altered antibody are contemplated. In one diagnostic application, the invention provides a method for determining the presence of an antigen of interest comprising exposing a sample suspected of containing the antigen to the altered antibody and determining binding of the altered antibody to the sample. For this use, the invention provides a kit comprising the altered antibody and instructions for using the altered antibody to detect the antigen.

The invention further provides: isolated nucleic acid encoding the altered antibody; a vector comprising the nucleic acid, optionally, operably linked to control sequences recognized by a host cell transformed with the vector; a host cell transformed with the nucleic acid; a process for producing the altered antibody comprising culturing the host cell so that the nucleic acid is expressed and, optionally, recovering the altered antibody from the host cell culture (e.g. from the host cell culture medium).

The invention also provides a composition comprising the altered antibody and a pharmaceutically acceptable carrier or diluent. This composition for therapeutic use is sterile and may be lyophilized.

The invention further provides a method for treating a mammal comprising administering an effective amount of the altered antibody to the mammal.

In addition, the invention provides a method of making an altered antibody comprising incorporating non-human hypervariable region residues into an acceptor human framework and further comprising introducing one or more amino acid substitutions in one or more hypervariable regions, without modifying the acceptor human framework sequence, and selecting an antibody with a binding affinity ($K_d$) value of no more than about $5 \times 10^{-7}$ M.

Moreover, the invention provides a method of mutating a nucleic acid sequence comprising:
(a) annealing from about two to about 20 oligonucleotides to a single stranded nucleic acid template, wherein the oligonucleotide:template ratio for each oligonucleotide is greater than 1;
(b) removing excess unannealed oligonucleotides; and
(c) filling in a nucleic acid strand which is complementary to the template.

In yet a further aspect, the invention provides a method of selecting an altered antibody comprising:
(a) preparing nucleic acid encoding at least the variable heavy (VH) and variable light (VL) domains of an antibody, each comprising an acceptor human framework and hypervariable regions of a non-human antibody;
(b) substituting hypervariable region residues by introducing an approximately 10-50 percent mutation rate into the nucleic acid so as to maintain a bias towards the non-human hypervariable region sequences; and
(c) selecting one or more altered antibodies that bind antigen.

BRIEF DESCRIPTION OF THE DRAWINGS

FIGS. 1A-1B depict amino acid sequences of the acceptor human consensus framework and the murine monoclonal antibodies: MHM24 (which binds CD11a), MaeII (which binds IgE) and D3 (which binds tissue factor, TF). Numbering is according to Kabat et al. (Kabat et al., *Sequences of Proteins of Immunological Interest*, 5th Ed., Public Health Service, National Institutes of Health, Bethesda, Md. (1991)). The extended hypervariable regions are boxed. Differences between the acceptor human consensus framework and the human consensus sequence of the Kabat heavy chain subgroup III are in bold. These include R71A, N73T, and L78A (Carter et al., *Proc. Natl. Acad. Sci. USA* 89:4285 (1992)). For the library design and direct hypervariable region grafts, the hypervariable regions were L1 (24-34), L2 (50-56), L3 (89-97), H1 (26-35a), H2 (49-65), H3 (93-102). The diversity in positions 49 and 94 was limited to A, G, S and T for position 49 and R or K for position 94.

FIG. 2 shows affect of reagent (PB) on DNA binding to silica. The binding of plasmid DNA (Δ), single stranded template DNA (●), and an 81 base pair oligonucleotide (■) to a silica column was monitored by A260 as a function of the amount of reagent (PB) added. The silica column and PB reagent were obtained from a QIAquick® PCR purification kit (Qiagen kit 28106).

FIGS. 3A-1, 3A-2, 3B-1, 3B-2, 3C-1 and 3C-2 represent distribution and sequence of hypervariable regions replaced during mutagenesis using 6 oligonucleotides. Hypervariable region sequences from the initial Fab displayed phage libraries designed for humanization of the murine monoclonal antibodies D3 (FIGS. 3A-1 and 3A-2), MHM24 (FIGS. 3B-1 and 3B-2) and MaeII (FIGS. 3C-1 and 3C-2) are shown. The hypervariable region sequences of the original murine antibodies are boxed. Hypervariable regions that were not replaced during the mutagenesis are shown in bold. Each hypervariable region in each library was replaced approximately 50 percent of the time. The sequence of the hypervariable regions that were replaced during mutagenesis reflects a bias towards the original murine hypervarible region sequence.

FIGS. 4A-4B depict sequence analysis and phage ELISA affinities of clones following selection on antigen. Partial sequences are shown for clones selected for binding to IgE (sequences in H1), LFA-1 (sequences in L2) and TF (sequences in L1, L2 or L3). Additional sequences changes in the VL or VH domains observed in regions outside these areas are noted. Amino acids identical to the direct hypervariable region grafted sequence are shaded and the hypervariable regions are boxed. The number of siblings of identical DNA sequence and the affinity of each clone as determined by phage ELISA is noted. From the MaeII humanization library, 60 complete sequences were analyzed; 33 and 49 complete sequences were analyzed for the MHM24 and D3 humanization libraries, respectively. The affinity of the direct hypervariable region grafted variants were 4 and 20 nM for the MHM24 and D3 grafted variants, respectively. No detectable binding was observed with the MaeII hypervariable region grafted variant.

FIG. 5 depicts schematically a comparison between prior humanization techniques (upper right), and the present method for making "CDR-repaired" antibodies (lower right).

FIGS. 6A-6B depict exemplary acceptor human consensus framework sequences for use in practicing the instant invention with sequence identifiers as follows:

VARIABLE HEAVY (VH) CONSENSUS FRAMEWORKS human VH subgroup I consensus framework minus Kabat CDRs (SEQ ID NO:23)
human VH subgroup I consensus framework minus extended hypervariable regions (SEQ ID NOs:24-26)
human VH subgroup II consensus framework minus Kabat CDRs (SEQ ID NO:27)
human VH subgroup II consensus framework minus extended hypervariable regions (SEQ ID NOs:28-30)
human VH subgroup II consensus framework minus extended
human VH subgroup III consensus framework minus Kabat CDRs (SEQ ID NO:31)
human VH subgroup III consensus framework minus extended hypervariable regions (SEQ ID NOs:32-34)
human VH acceptor framework minus Kabat CDRs (SEQ ID NO:35)
human VH acceptor framework minus extended hypervariable regions (SEQ ID NOs:36-37)
human VH acceptor 2 framework minus Kabat CDRs (SEQ ID NO:38)
human VH acceptor 2 framework minus extended hypervariable regions (SEQ ID NOs:39-41)

VARIABLE LIGHT (VL) CONSENSUS FRAMEWORKS human VL kappa subgroup I consensus framework (SEQ ID NO:42)

human VL kappa subgroup II consensus framework (SEQ ID NO:43)

human VL kappa subgroup III consensus framework (SEQ ID NO:44)

human VL kappa subgroup IV consensus framework (SEQ ID NO:45)

DETAILED DESCRIPTION OF THE PREFERRED EMBODIMENTS

I. Definitions

The present application uses "variable domain residue numbering as in Kabat" which refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

A "non-human antibody" is an antibody comprising variable domain sequences from a non-human species. Preferred non-human antibodies are rodent or murine antibodies. Such antibodies are generally made by immortalization of a non-human B cell, e.g. via hybridoma technology.

An "altered antibody" herein is an antibody comprising variable light (VL) and variable heavy (VH) amino acid sequences which differ from a naturally occurring antibody amino acid sequence.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

An "acceptor human framework" for the purposes herein is a framework comprising the amino acid sequence of a VL or VH framework derived from a human immunoglobulin framework, or from a human consensus framework.

An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at positions four, three or less of 71H, 73H, 78H and 93H (if the framework includes position 93H); for instance, the amino acid residues at those positions may be 71A, 73T, 78A, and/or 93S. Preferably, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Preferably the selection of human immunoglobulin VL or VH sequences is from a subgroup of variable domain sequences. Preferably, the subgroup of sequences is a subgroup as in Kabat et al. For the VL, the most preferred subgroup is subgroup kappa I as in Kabat et al. As to VH, the most preferred subgroup is subgroup III as in Kabat et al.

A "VH subgroup III consensus framework" comprises the consensus sequence obtained from the amino acid sequences in variable heavy subgroup III of Kabat et al. Preferably, the VH subgroup III consensus framework amino acid sequence comprises:

```
                                    (SEQ ID NO: 1)
    EVQLVESGGGLVQPGGSLRLSCAAS-

H1-
                                    (SEQ ID NO: 2)
    WVRQAPGKGLEWV-

H2-
                                    (SEQ ID NO: 3)
    RFTISRDNSKNTLYLQMNSLRAEDTAVYYC-

H3-
                                    (SEQ ID NO: 4)
    WGQGTLVTVSS.
```

A "VL subgroup I consensus framework" comprises the consensus sequence obtained from the amino acid sequences in variable light kappa subgroup I of Kabat et al. Preferably, the VH subgroup I consensus framework amino acid sequence comprises:

```
                                    (SEQ ID NO: 5)
    DIQMTQSPSSLSASVGDRVTITC-

L1-
                                    (SEQ ID NO: 6)
    WYQQKPGKAPKLLIY-

L2-
                                    (SEQ ID NO: 7)
    GVPSRFSGSGSGTDFTLTISSLQPEDFATYYC-

L3-
                                    (SEQ ID NO: 8)
    FGQGTKVEIK.
```

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "antibody" is used in the broadest sense and specifically covers monoclonal antibodies (including intact antibodies), polyclonal antibodies, multispecific antibodies (e.g., bispecific antibodies), and antibody fragments so long as they exhibit the desired biological activity.

The term "hypervariable region" when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196: 901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32...34 | H30-H35B |
| (Kabat Numbering) | | | | |
| H1 | H31-H35 | H26-H35 | H26-H32 | H30-H35 |
| (Chothia Numbering) | | | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-34 (L1), 50-56 or 49-56 (L2) and 89-97 (L3) in the VL and 26-35, 26-35A or 26-35B (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

An "intact antibody" herein is one comprising a VL and VH domains, as well as complete light and heavy chain constant domains.

A "human IgG1" antibody herein comprises constant region sequences of a human IgG1 antibody.

The term "monoclonal antibody" as used herein refers to an antibody obtained from a population of substantially homogeneous antibodies, i.e., the individual antibodies comprising the population are identical and/or bind the same epitope except for possible variants that may arise during production of the monoclonal antibody, such variants generally being present in minor amounts. In contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence, except for possible FR substitution(s) as noted above. The humanized antibody optionally also will comprise at least a portion of an immunoglobulin constant region, typically a human immunoglobulin Fc region. For further details, see Jones et al., *Nature* 321:522-525 (1986); Riechmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the techniques for making human antibodies as disclosed herein. Human antibodies can be produced using various techniques known in the art. In one embodiment, the human antibody is selected from a phage library, where that phage library expresses human antibodies (Vaughan et al. *Nature Biotechnology* 14:309-314 (1996): Sheets et al. *PNAS (USA)* 95:6157-6162 (1998)); Hoogenboom and Winter, *J. Mol. Biol.,* 227:381 (1991); Marks et al., *J. Mol. Biol.,* 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10: 779-783 (1992); Lonberg et al., *Nature* 368: 856-859 (1994); Morrison, *Nature* 368:812-13 (1994); Fishwild et al., *Nature Biotechnology* 14: 845-51 (1996); Neuberger, *Nature Biotech-* nology 14: 826 (1996); Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The expression "linear antibodies" when used throughout this application refers to the antibodies described in Zapata et al. *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

An "amino acid substitution" refers to the replacement of an existing amino acid residue in a predetermined amino acid sequence with another different amino acid residue.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disorder as well as those in which the disorder is to be prevented.

A "disorder" is any condition that would benefit from treatment with the altered antibody. This includes chronic and acute disorders or diseases including those pathological conditions which predispose the mammal to the disorder in question.

The term "CD11a" when used herein refers to the alpha subunit of LFA-1 from any mammal, but preferably from a human. The CD11a may be isolated from a natural source of the molecule or may be produced by synthetic means (e.g., using recombinant DNA technology.) The amino acid sequence for human CD11a is described in EP 362 526B1, for example.

The term "LFA-1-mediated disorder" refers to a pathological state caused by cell adherence interactions involving the LFA-1 receptor on lymphocytes. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitis; allergic conditions such as eczema and asthma; conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; chronic obstructive pulmonary disease (COPD); bronchitis; insulinitis; rhinitis; urticaria; glomerulonephritis; diseases involving leukocyte diapedesis; CNS inflammatory disorder; multiple organ injury syndrome secondary to septicaemia or trauma; autoimmune hemolytic anemia; myethemia gravis; antigen-antibody complex mediated diseases; nephrotic syndrome; malignancies (e.g., B-cell malignancies such as chronic lymphocytic leukemia or hairy cell leukemia); all types of transplantations, including graft vs. host or host vs. graft disease; HIV and rhinovirus infection; pulmonary fibrosis; invasion of tumor cells into secondary organs etc.

A "hypercoagulable state" is one in which due to an inherited or acquired disorder there is an increased propensity for thrombosis. This state is manifested clinically by either an increase in number of thrombotic events or episodes, thrombosis at an early age, a familial tendency toward thrombosis, and thrombosis at unusual sites. Patients that are susceptible to developing a hypercoagulable state include those having the following history: (1) thrombosis at a young age (age under 50 years); (2) family history of thrombosis; (3) recurrent thrombosis; (4) thrombosis in an unusual site; and (5) pregnancies complicated by frequent miscarriage. Hypercoagulable states or diseases can be passed onto in family members that inherit particular diseases or abnormalties (e.g., Factor V Leiden Deficiency, Homocystinuria or Hyperhomocysteinemia, Antithrombin III deficiency, Protein C Deficiency, Protein S Deficiency, increased Factor VIII, Fibrinolysis, and Dysfibrinogenemia). Hypercoagulable states can be acquired as a result of other conditions (e.g., pregnancy, estrogen consumption (oral contraceptives, estrogen replacement therapy, tamoxifen), surgery, trauma, infection, bites of poisonous snakes, acute liver disease, sepsis, malignancy (cancer in idiopathic hypercoagulability), myeloproliferative disorder, hyperlipidemia, homocystinuria, systemic lupus erythematosus, burns, renal disease, eclampsia, heat stroke, antiphospholipid antibodies, nephrotic syndrome, neoplasms). Manipulation of body fluids can also result in an undesirable thrombus, particularly in blood transfusions or fluid sampling, as well as procedures involving extracorporeal circulation (e.g., cardiopulmonary bypass surgery) and dialysis.

"IgE mediated disorders" include atopic disorders, which are characterized by an inherited propensity to respond immunologically to many common naturally occurring inhaled and ingested antigens and the continual production of IgE antibodies. Specific atopic disorders includes allergic asthma, allergic rhinitis, atopic dermatitis and allergic gastroenteropathy. Atopic patients often have multiple allergies, meaning that they have IgE antibodies to, and symptoms from, many environmental allergens, including pollens, fungi (e.g., molds), animal and insect debris and certain foods. Disorders associated with elevated IgE levels are not limited to those with an inherited (atopic) etiology. Other disorders associated with elevated IgE levels, that appear to be IgE-mediated and are treatable with the formulations of this present invention include hypersensitivity (e.g., anaphylactic hypersensitivity), eczema, urticaria, allergic bronchopulmonary aspergillosis, parasitic diseases, hyper-IgE syndrome, ataxia-telangiectasia, Wiskott-Aldrich syndrome, thymic alymphoplasia, IgE myeloma and graft-versus-host reaction.

"Mammal" for purposes of treatment refers to any animal classified as a mammal, including humans, domestic and farm animals, nonhuman primates, and zoo, sports, or pet animals, such as dogs, horses, cats, cows, etc.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD).

The term "cytotoxic agent" as used herein refers to a substance that inhibits or prevents the function of cells and/or causes destruction of cells. The term is intended to include radioactive isotopes (e.g. At211, I131, I125, Y90, Re 186, Re188, Sm153, Bi212, P32 and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; GEMZAR® gemcitabine; 6- thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine (DMFO); retinoids such as retinoic acid;

capecitabine; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON, toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

An "isolated" nucleic acid molecule is a nucleic acid molecule that is identified and separated from at least one contaminant nucleic acid molecule with which it is ordinarily associated in the natural source of the antibody nucleic acid.

An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers.

It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "library" refers to a plurality of antibody or antibody fragment sequences (for example, altered antibodies of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to a coat protein on the surface of phage, e.g., filamentous phage, particles. One utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, Methods: A companion to *Methods in Enzymology*, 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucloside H-phosphonate intermediates as described by Froeshler et al., *Nucl. Acids, Res.*, 14:5399-5407 (1986)). Further methods include the polymerase chain reaction and other autoprimer methods and oligonucleotide syntheses on solid supports. All of these methods are described in Engels et al., *Agnew. Chem. Int. Ed. Engl.*, 28:716-734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation.

II. Modes for Carrying Out the Invention

A. Making and Selecting Altered Antibodies (i) Parent or Starting Antibody

The invention herein relates to a method for making or selecting an altered antibody. The parent antibody or starting antibody, generally a non-human antibody, is prepared using techniques available in the art for generating such antibodies.

The parent antibody is directed against a target antigen of interest. Preferably, the target antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as aFGF and bFGF; epidermal growth factor (EGF); transforming growth factor (TGF) such as TGF-alpha and TGF-beta; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred molecular targets for antibodies encompassed by the present invention include CD proteins such as CD3, CD4, CD8, CD19, CD20, CD22, CD40 and CD304; members of the ErbB receptor family such as the EGF receptor, HER2, HER3 or HER4 receptor; cell adhesion molecules such as LFA-1, Mac1, p150,95, VLA-4, ICAM-1, VCAM and αv/β3 integrin including either alpha or beta subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C; c-met; tissue factor; μ7 etc.

The antigen used to generate an antibody may be isolated from a natural source thereof, or may be produced recombinantly or made using other synthetic methods. Alternatively, cells comprising native or recombinant antigen can be used as immunogens for making antibodies.

The parent antibody may have pre-existing strong binding affinity for the target antigen. For example, the parent antibody may bind the antigen of interest with a binding affinity ($K_d$) value of no more than about $5 \times 10^{-7}$ M, more preferably no more than about $5 \times 10^{-8}$ M and optionally no more than about $5 \times 10^{-9}$ M. Generally, the antibody will bind antigen with an affinity in the nanomolar or better range.

Antibody "binding affinity" may be determined by equilibrium methods (e.g. enzyme-linked immunoabsorbent assay (ELISA) or radioimmunoassay (RIA)), or kinetics (e.g. BIACORE™ analysis), for example.

Also, the antibody may be subjected to other "biological activity assays", e.g., in order to evaluate its "potency" or pharmacological activity and potential efficacy as a therapeutic agent. Such assays are known in the art and depend on the target antigen and intended use for the antibody. Examples include the keratinocyte monolayer adhesion assay and the mixed lymphocyte response (MLR) assay for CD11a (see WO98/23761); tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); agonistic activity or hematopoiesis assays (see WO 95/27062); tritiated thymidine incorporation assay; and alamar blue assay to measure metabolic activity of cells in response to a molecule such as VEGF.

In a first step, the non-human antibody, usually, a rodent, murine or non-human primate antibody may be made, but an existing non-human antibody, or sequence information for an existing non-human antibody can also be used. Generally, hybridoma technology is used to generate the non-human antibody, exemplary techniques for generating such antibodies being provided herein. The amino acid sequences of the variable regions of the non-human antibody, or at least the hypervariable regions thereof, can be determined using techniques well known to the skilled artisan.

(ii) Human Framework Selection

The acceptor human frameworks are selected. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the non-human framework sequence by aligning the non-human framework sequence with various human framework sequences in a collection of human framework sequences, and selected the most homologous framework sequence as the acceptor.

The most preferred human consensus frameworks herein are from, or derived from, VH subgroup III and/or VL kappa subgroup I consensus framework sequences.

Thus, the VH acceptor human framework may comprise one, two, three or all of the following framework sequences:

```
FR1 comprising
                                        (SEQ ID NO: 1)
EVQLVESGGGLVQPGGSLRLSCAAS, FR2 comprising
                                        (SEQ ID NO: 2)
WVRQAPGKGLEWV, FR3 comprising FR3 comprises
                                        (SEQ ID NO: 9)
RFTISX1DX2SKNTX3YLQMNSLRAEDTAVYYC,
wherein X1 is A or R, X2 is T or N,
and X3 is A or L, FR4 comprising
                                        (SEQ ID NO: 4)
WGQGTLVTVSS.
```

Preferred VH consensus frameworks include:
human VH subgroup I consensus framework minus Kabat CDRs (SEQ ID NO:23);
human VH subgroup I consensus framework minus extended hypervariable regions (SEQ ID NOs:24-26);
human VH subgroup II consensus framework minus Kabat CDRs (SEQ ID NO:27);
human VH subgroup II consensus framework minus extended hypervariable regions (SEQ ID NOs:28-30);
human VH subgroup III consensus framework minus Kabat CDRs (SEQ ID NO:31);
human VH subgroup III consensus framework minus extended hypervariable regions (SEQ ID NO:32-34);
human VH acceptor framework minus Kabat CDRs (SEQ ID NO:35);
human VH acceptor framework minus extended hypervariable regions (SEQ ID NOs:36-37);
human VH acceptor 2 framework minus Kabat CDRs (SEQ ID NO:38); or
human VH acceptor 2 framework minus extended hypervariable regions (SEQ ID NOs:39-41).

Preferably, the VH acceptor human framework comprises one, two, three or all of the following framework sequences:

```
FR1 comprising
                                        (SEQ ID NO: 1)
EVQLVESGGGLVQPGGSLRLSCAAS, FR2 comprising
                                        (SEQ ID NO: 2)
WVRQAPGKGLEWV, FR3 comprising
                                        (SEQ ID NO: 10)
RFTISADTSKNTAYLQMNSLRAEDTAVYYC, (SEQ ID NO: 11)
RFTISADTSKNTAYLQMNSLRAEDTAVYYCA, (SEQ ID NO: 12)
RFTISADTSKNTAYLQMNSLRAEDTAVYYCAR, (SEQ ID NO: 13)
RFTISADTSKNTAYLQMNSLRAEDTAVYYCS,
or
                                        (SEQ ID NO: 14)
RFTISADTSKNTAYLQMNSLRAEDTAVYYCSR FR4 comprising
                                        (SEQ ID NO: 4)
WGQGTLVTVSS.
```

The VL acceptor human framework may comprise one, two, three or all of the following framework sequences:

```
FR1 comprising
                                        (SEQ ID NO: 5)
DIQMTQSPSSLSASVGDRVTITC, FR2 comprising
                                        (SEQ ID NO: 6)
WYQQKPGKAPKLLIY, FR3 comprising
                                        (SEQ ID NO: 7)
GVPSRFSGSGSGTDFTLTISSLQPEDFATYYC, FR4 comprising
                                        (SEQ ID NO: 8)
FGQGTKVEIK.
```

Preferred VL consensus frameworks include:
human VL kappa subgroup I consensus framework (SEQ ID NO:42);
human VL kappa subgroup II consensus framework (SEQ ID NO:43);
human VL kappa subgroup III consensus framework (SEQ ID NO:44); or
human VL kappa subgroup IV consensus framework (SEQ ID NO:45)

While the acceptor may be identical in sequence to the human framework sequence selected, whether that be from a human immunoglobulin or a human consensus framework, the present application contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

(iii) Incorporation of Hypervariable Region Residues into Human Frameworks

Hypervariable region residues of the non-human antibody Are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35 (H1), 50-65 or 49-65 (H2) and 93-102, 94-102, or 95-102 (H3).

While "incorporation" of hypervariable region residues is discussed herein, it will be appreciated that this can be achieved various ways, for example, nucleic acid encoding the desired amino acid sequence can be generated by mutating nucleic acid encoding the mouse variable domain sequence so that the framework residues thereof are changed to acceptor human framework residues, or by mutating nucleic acid encoding the human variable domain sequence so that the hypervariable domain residues are changed to non-human residues, or by synthesizing nucleic acid encoding the desired sequence, etc.

In the examples herein, hypervariable region-grafted variants were generated by Kunkel mutagenesis of nucleic acid encoding the human acceptor sequences, using a separate oligonucleotide for each hypervariable region. Kunkel et al., *Methods Enzymol.* 154:367-382 (1987). Correct clones were assessed by DNA sequencing.

Previous efforts to transfer the antigen binding information of non-human monoclonal antibodies onto a human acceptor have relied on the introduction of changes within the framework to correct and re-establish proper hypervariable region-antigen interactions. Rather than remodeling the hypervariable region-framework interface by altering framework residues, the present invention concerns selection of modified hypervariable regions that correct framework deficiencies while still maintaining antigen interactions.

(iv) Phage Display

According to the preferred method, the hypervariable region sequences are selected using phage display technology, as this provides a convenient and fast method for generating and screening many different altered antibodies. However, other methods for making and screening altered antibodies are available to the skilled person.

Phage display technology has provided a powerful tool for generating and selecting novel proteins which bind to a ligand, such as an antigen. Using the techniques of phage display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phage display systems where the nucleic acid sequence encoding the protein or polypeptide is fused to a nucleic acid sequence encoding a portion of the gene III protein have been developed. (Bass, S., *Proteins,* 8:309 (1990); Lowman and Wells, *Methods: A Companion to Methods in Enzymology,* 3:205 (1991)). In a monovalent phage display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, for e.g., Kunkel et al., *Methods Enzymol.* 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T) H
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. *Nucleic Acids Res.* 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA,* 75:5765 (1978).

The DNA template is generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. *Meth. Enzymol.*, 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

(v) Mutagenesis Method

According to the present invention, preferably large phage display libraries are used. Unfortunately as the number of oligonucleotides in a mutagenesis reaction increases the frequency of clones containing all mutagenic oligonucleotides decreases. To compensate for this, one could increase the oligonucleotide concentration to ensure that all sites are fully occupied during the annealing process; however, as the concentration of oligonucleotides in the polymerase reaction increases, the potential for side reactions also increases resulting in a decreased yield of mutagenized clones and an overall reduced library size. To overcome this problem, a "clean-up step" was developed herein, to remove excess unannealed oligonucleotides prior to the polymerase reaction. Aside from use with respect to selecting altered antibodies, namely CDR-repaired antibodies as described herein, it is believed that this methodology is useful in other situations where nucleic acid is mutated, particularly where a large number of oligonucleotides are employed during mutagenesis.

Accordingly, a 3-step method for mutating a nucleic acid sequence comprising:
(a) annealing from about two to about 20 oligonucleotides to a single stranded nucleic acid template, wherein the oligonucleotide:template ratio for each oligonucleotide is greater than 1;
(b) removing excess unannealed oligonucleotides; and
(c) filling in a nucleic acid strand which is complementary to the template.

The template in step (a) can be the coding (or complementary strand thereof) for an antibody or altered antibody (e.g. a CDR repaired antibody variant herein or an altered antibody with hypervariable regions from a non-human antibody incorporated into a acceptor human framework). In this embodiment, the mutagenesis may be used to substitute one or more hypervariable region residues of the antibody or altered antibody. Preferably the antibody or altered antibody is in the form of an antibody fragment, such as a scFv or Fab fragment, which may be displayed on phage.

Step (b) preferably comprises exposing a mixture of the template and annealed or unannealed oligonucleotides to a reagent that enables the template to bind to a silica matrix, but not oligonucleotides shorter than 100 base pairs in length. Following exposure to the reagent, the composition is run through a solid phase (e.g. silica column), the unannealed oligonucleotides are washed from the solid phase. Following this step, the template may be recovered from the solid phase. This step separates unannealed oligonucleotides away from the template with annealed oligonucleotides. Preferably the reagent comprises guanidine hydrochloride, e.g., PB (QIAquick®). In step (a), the oligo:template ratio for each oligo is greater than 1, such that the oligonucleotides saturate corresponding sites on the template. Generally, at least a 2-3 fold excess of each oligo, e.g. a 10 fold excess, is used.

Following the clean up step, the complementary second strand of nucleic acid is filled in, using e.g. polymerase, and ligase to complete synthesis of the second strand.

(vi) Soft Randomization

In the preferred embodiment of the present invention, a technique called "soft randomization" of the hypervariable regions is used. This maintains a bias towards the murine hypervariable region sequence, while introducing a 10-50 percent mutation at each selected position. This technique increases the capacity of the library screening employed and avoids a change in the antigen epitope recognized by the antibody. According to this soft randomization technique, sequence diversity is introduced into each hypervariable region using a strategy that maintains a bias towards the murine hypervariable region sequence. This was accomplished using a poisoned oligonucleotide synthesis strategy first described by Gallop et al., *J. Med. Chem.* 37:1233-1251 (1994). However, other methods for maintaining a bias towards the non-human hypervariable region residue are available, such as error prone PCR, DNA shuffling, etc.

According to the preferred method herein, for a given position within a hypervariable region to be mutated, the codon encoding the wild-type amino acid is poisoned with a mixture (e.g. a 70-10-10-10 mixture) of nucleotides resulting in an approximately 10-50 percent mutation rate at each selected hypervariable region position. To achieve this, the codon encoding the wild-type hypervariable region amino acid to be mutated is synthesized with a low level of contaminating mixture of the other three nucleotides, such as a 70-10-10-10 mixture of nucleotides. Thus, by way of example, for soft randomization of met (ATG), the first position synthesized is a mixture of 70% A, and 10% each of G, T and C; the second position is a mixture of 70% T, and 10% each of A, G, and C; and the third position is a mixture of 70% G, and 10% each of A, C and T.

Soft randomized oligonucleotides can be patterned after the murine hypervariable region sequences and encompass the same regions defined by the direct hypervariable region grafts. Optionally, two positions, amino acids at the beginning of H2 and H3 in the VH domain, may be limited in their diversity: the codon RGC may be used for position 49 encoding A, G, S or T and at position 94, the codon ARA may be used encoding R or K.

(vii) Expression Vectors and Transformed Hosts

Nucleic acid cassettes can be cloned into any suitable vector for expression of a portion or the entire light or heavy chain sequence containing the targeted amino acid substitutions generated via the PCR reaction. According to methods detailed in the invention, the nucleic acid cassette is cloned into a vector allowing production of a portion or the entire light or heavy chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art. In another embodiment, wherein a particular variant amino acid combination is to be expressed, the nucleic acid cassette contains a sequence that is able to encode all or a portion of the heavy or light chain variable domain, and is able to encode the variant amino acid combinations. For production of antibodies containing these variant amino acids or combinations of variant amino acids, as in a library, the nucleic acid cassettes can be inserted into an expression vector containing additional antibody sequence, for example all or portions of the variable or constant domains of the light and heavy chain variable regions. These additional antibody sequences can also be fused to other nucleic acids sequences, such as sequences which encode viral coat proteins and therefore allow production of a fusion protein.

The present invention provides a replicable expression vector comprising a nucleic acid sequence encoding a gene fusion, wherein the gene fusion encodes a fusion protein comprising an antibody variable domain, or an antibody variable domain and a constant domain, fused to all or a portion of a viral coat protein. Also included is a library of diverse replicable expression vectors comprising a plurality of gene fusions encoding a plurality of different fusion proteins including a plurality of the antibody variable domains generated with diverse sequences as described above. The vectors can include a variety of components and are preferably constructed to allow for movement of antibody variable domain between different vectors and/or to provide for display of the fusion proteins in different formats.

The preferred phagemid is a monovalent Fab-g3 display vector, which may consist of 2 open reading frames under control of an appropriate promoter, such as the phoA promoter. The first open reading frame may comprise a signal sequence (e.g. the stII signal sequence) fused to the light chain sequence and the second open reading frame may comprise a signal sequence (e.g. the stII signal sequence) fused to the VH and CH1 domains of the heavy chain sequence, optionally followed by the minor phage coat protein P3.

Examples of vectors include phage vectors. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII, major coat protein PVIII, p3, Soc, Hoc, gpD (of bacteriophage lambda), minor bacteriophage coat protein 6 (pVI) (filamentous phage; *J Immunol Methods.* 231(1-2):39-51 (1999)), variants of the M13 bacteriophage major coat protein (P8) (*Protein Sci* 9(4):647-54 (2000)). The fusion protein can be displayed on the surface of a phage and suitable phage systems include M13KO7 helper phage, M13R408, M13-VCS, and Phi X 174, pJuFo phage system (*J Virol.* 75(15): 7107-13.v (2001)), hyperphage (*Nat Biotechnol.* 19(1):75-8 (2001)). The preferred helper phage is M13KO7, and the preferred coat protein is the M13 Phage gene III coat protein. The preferred host is *E. coli*, and protease deficient strains of *E. coli*. Vectors, such as the fth1 vector (*Nucleic Acids Res.* 29(10):E50-0 (2001)) can be useful for the expression of the fusion protein.

The expression vector also can have a secretory signal sequence fused to the DNA encoding each subunit of the antibody or fragment thereof. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., *Gene,* 68:1931 (1983), MalE, PhoA and other genes. A preferred prokaryotic signal sequence for practicing this invention is the *E. coli* heat-stable enterotoxin II (STII) signal sequence as described by Chang et al., *Gene* 55:189 (1987), and malE.

The vector also typically includes a promoter to drive expression of the fusion protein. Promoters most commonly used in prokaryotic vectors include the lac Z promoter system, the alkaline phosphatase pho A promoter, the bacteriophage $\square_{PL}$ promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (e.g., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is preferably fused to an antibody variable domain which is not fused to the viral coat protein. Nucleic acid sequences encoding, for example, a polyhistidine tag, are useful for identifying fusion proteins including antibody variable domains that bind to a specific antigen using immunohistochemistry. Tags useful for detection of antigen binding can be fused to either an antibody variable domain not fused to a viral coat protein or an antibody variable domain fused to a viral coat protein.

Another useful component of the vectors used to practice this invention is phenotypic selection genes. Typical phenotypic selection genes are those encoding proteins that confer antibiotic resistance upon the host cell. By way of illustration, the ampicillin resistance gene (ampr), and the tetracycline resistance gene (tetr) are readily employed for this purpose.

The vector can also include nucleic acid sequences containing unique restriction sites and suppressible stop codons. The unique restriction sites are useful for moving antibody variable domains between different vectors and expression systems. The suppressible stop codons are useful to control the level of expression of the fusion protein and to facilitate purification of soluble antibody fragments. For example, an amber stop codon can be read as Gln in a supE host to enable phage display, while in a non-supE host it is read as a stop codon to produce soluble antibody fragments without fusion to phage coat proteins. These synthetic sequences can be fused to one or more antibody variable domains in the vector.

It is preferable to use vector systems that allow the nucleic acid encoding an antibody sequence of interest, for example a CDR-repaired antibody, to be easily removed from the vector system and placed into another vector system. For example, appropriate restriction sites can be engineered in a vector system to facilitate the removal of the nucleic acid sequence encoding an antibody or antibody variable domain having variant amino acids. The restriction sequences are usually chosen to be unique in the vectors to facilitate efficient excision and ligation into new vectors. Antibodies or antibody variable domains can then be expressed from vectors without extraneous fusion sequences, such as viral coat proteins or other sequence tags.

Between nucleic acid encoding antibody variable domain (gene 1) and the viral coat protein. (gene 2), DNA encoding a termination codon may be inserted, such termination codons including UAG (amber), UAA (ocher) and UGA (opel). (Davis et al. *Microbiology*, Harper & Row, New York, pp. 237, 245-47 and 374 (1980)). The termination codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as *E. coli* suppressor strain (Bullock et al., *BioTechniques* 5:376-379 (1987)). Any acceptable method may be used to place such a termination codon into the mRNA encoding the fusion polypeptide.

The suppressible codon may be inserted between the first gene encoding an antibody variable domain, and a second gene encoding at least a portion of a phage coat protein. Alternatively, the suppressible termination codon may be inserted adjacent to the fusion site by replacing the last amino acid triplet in the antibody variable domain or the first amino acid in the phage coat protein. When the plasmid containing the suppressible codon is grown in a suppressor host cell, it results in the detectable production of a fusion polypeptide containing the polypeptide and the coat protein. When the plasmid is grown in a non-suppressor host cell, the antibody variable domain is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

The light and/or heavy antibody variable domains can also be fused to an additional peptide sequence, the additional peptide sequence allowing the interaction of one or more fusion polypeptides on the surface of the viral particle or cell. These peptide sequences are herein referred to as "dimerization sequences", "dimerization peptides" or "dimerization domains". Suitable dimerization domains include those of proteins having amphipathic alpha helices in which hydrophobic residues are regularly spaced and allow the formation of a dimer by interaction of the hydrophobic residues of each protein; such proteins and portions of proteins include, for example, leucine zipper regions. The dimerization regions are preferably located between the antibody variable domain and the viral coat protein.

In some cases the vector encodes a single antibody-phage polypeptide in a single chain form containing, for example, both the heavy and light chain variable regions fused to a coat protein. In these cases the vector is considered to be "monocistronic", expressing one transcript under the control of a certain promoter. This cistronic sequence may be connected at the 5' end to an *E. coli* malE or heat-stable enterotoxin II (STII) signal sequence and at its 3' end to all or a portion of a viral coat.

In other cases, the variable regions of the heavy and light chains can be expressed as separate polypeptides, the vector thus being "bicistronic", allowing the expression of separate transcripts. In these vectors, a suitable promoter, such as the Ptac or PhoA promoter, can be used to drive expression of a bicistronic message. A first cistron, encoding, for example, a light chain variable domain, is connected at the 5' end to a *E. coli* malE or heat-stable enterotoxin II (STII) signal sequence and at the 3' end to a nucleic acid sequence encoding a gD tag. A second cistron, encoding, for example, a heavy chain variable domain, is connected at its 5' end to a *E. coli* malE or heat-stable enterotoxin II (STII) signal sequence and at the 3' end to all or a portion of a viral coat protein.

Fusion polypeptides with an antibody variable domain can be displayed on the surface of a cell or virus in a variety of formats. These formats include single chain Fv fragment (scFv), F(ab) fragment and multivalent forms of these fragments. The multivalent forms preferably are a dimer of ScFv, Fab, or F(ab)', herein referred to as (ScFv)$_2$, F(ab)$_2$ and F(ab)'$_2$, respectively. The multivalent forms of display are preferred in part because they have more than one antigen binding site which generally results in the identification of lower affinity clones and also allows for more efficient sorting of rare clones during the selection process.

Methods for displaying fusion polypeptides comprising antibody fragments, on the surface of bacteriophage, are well known in the art, for example as described in patent publication number WO 92/01047 and herein. Other patent publications WO 92/20791; WO 93/06213; WO 93/11236 and WO 93/19172, describe related methods and are all herein incorporated by reference. Other publications have shown the identification of antibodies with artificially rearranged V gene repertoires against a variety of antigens displayed on the surface of phage (for example, Hoogenboom & Winter *J. Mol. Biol.* 227 381-388 (1992); and as disclosed in WO 93/06213 and WO 93/11236).

When a vector is constructed for display in a scFv format, it includes nucleic acid sequences encoding an antibody variable light chain domain and an antibody variable heavy chain variable domain. Typically, the nucleic acid sequence encoding an antibody variable heavy chain domain is fused to a viral coat protein. The nucleic acid sequence encoding the antibody variable light chain is connected to the antibody variable heavy chain domain by a nucleic acid sequence encoding a peptide linker. The peptide linker typically contains about 5 to 15 amino acids. Optionally, other sequences encoding, for example, tags useful for purification or detection can be fused at the 3' end of either the nucleic acid sequence encoding the antibody variable light chain or antibody variable heavy chain domain or both.

When a vector is constructed for F(ab) display, it includes nucleic acid sequences encoding antibody variable domains and antibody constant domains. A nucleic acid encoding a variable light chain domain is fused to a nucleic acid sequence encoding a light chain constant domain. A nucleic acid sequence encoding an antibody heavy chain variable domain is fused to a nucleic acid sequence encoding a heavy chain constant CH1 domain. Typically, the nucleic acid sequence encoding the heavy chain variable and constant domains are fused to a nucleic acid sequence encoding all or part of a viral coat protein. The heavy chain variable and constant domains are preferably expressed as a fusion with at least a portion of a viral coat protein and the light chain variable and constant domains are expressed separately from the heavy chain viral coat fusion protein. The heavy and light chains associate with one another, via covalent or non-covalent bond(s). Optionally, other sequences encoding, for example, polypeptide tags useful for purification or detection, can be fused at the 3' end of either the nucleic acid sequence encoding the antibody light chain constant domain or antibody heavy chain constant domain or both.

Preferably a bivalent moiety, for example, a F(ab)$_2$ dimer or F(ab)'$_2$ dimer, is used for displaying antibody fragments with the variant amino acid substitutions on the surface of a particle. It has been found that F(ab)'$_2$ dimers have the same affinity as F(ab) dimers in a solution phase antigen binding assay but the off rate for F(ab)'$_2$ are reduced because of a higher avidity in an assay with immobilized antigen. Therefore the bivalent format (for example, F(ab)'$_2$) is a particularly useful format since it can allow the identification of lower affinity clones and also allows more efficient sorting of rare clones during the selection process.

Vectors may be introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using electroporation as described in WO/00106717. Cells are grown in culture in standard culture broth, optionally for about 6-48 hours (or to $OD_{600}$=0.6-0.8) at about 37° C., and then the broth is centrifuged and the supernatant removed (e.g. decanted). Initial purification may be achieved by resuspending the cell pellet in a buffer solution (e.g. 1.0 mM HEPES pH 7.4) followed by recentriguation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

An exemplary recipient cell is the electroporation competent *E. coli* strain of the present invention, which is *E. coli* strain SS320 (Sidhu et al., *Methods Enzymol.* 328:333-363 (2000)). Strain SS320 was prepared by mating MC1061 cells with XL1-BLUE cells under conditions sufficient to transfer the fertility episome (F' plasmid) or XL1-BLUE into the MC1061 cells. Strain SS320 has been deposited with the American Type Culture Collection (ATCC), 10801 University Boulevard, Manassas, Va. USA, on Jun. 18, 1998 and assigned Deposit Accession No. 98795. Any F' episome which enables phage replication in the strain may be used in the invention. Suitable episomes are available from strains deposited with ATCC or are commercially available (CJ236, CSH18, DHF', JM101, JM103, JM105, JM107, JM109, JM110, KS1000, XL1-BLUE, 71-18 and others).

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

(viii) Screening for altered antibodies that bind antigen

Phage display of proteins, peptides and mutated variants thereof, involves constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, contacting the recombinant phage particles with a target molecule so that at least a portion of the particle bind to the target, and separating the particles which bind from particle that do not bind.

Antibody variable domain fusion proteins expressing the variant amino acids can be expressed on the surface of a phage or a cell and then screened for the ability of members of the group of fusion proteins to bind a target molecule, such as a target protein, which is typically an antigen of interest. Target proteins can also include protein L which binds to antibody or antibody fragments and can be used to enrich for library members that display correctly folded antibody fragments (fusion polypeptides). Target proteins, such as receptors, may be isolated from natural sources or prepared by recombinant methods by procedures known in the art.

Screening for the ability of a fusion polypeptide to bind a target molecule can also be performed in solution phase. For example, a target molecule can be attached with a detectable moiety, such as biotin. Phage that binds to the target molecule in solution can be separated from unbound phage by a molecule that binds to the detectable moiety, such as streptavidin-coated beads where biotin is the detectable moiety. Affinity of binders (fusion polypeptide that binds to target) can be determined based on concentration of the target molecule used, using formulas and based on criteria known in the art.

The purified target protein may be attached to a suitable matrix such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by methods described in Methods in *Enzymology*, 44 (1976), or by other means known in the art.

After attachment of the target protein to the matrix, the immobilized target is contacted with the library expressing the fusion polypeptides under conditions suitable for binding of at least a portion of the phage particles with the immobilized target. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the higher affinity binders. Binders may be dissociated from the immobilized target by a variety of methods. These methods include competitive dissociation using the wild-type ligand, altering pH and/or ionic strength, and methods known in the art. Selection of binders typically involves elution from an affinity matrix with a ligand. Elution with increasing concentrations of ligand should elute displayed binding molecules of increasing affinity.

The binders can be isolated and then reamplified or expressed in a host cell and subjected to another round of selection for binding of target molecules. Any number of rounds of selection or sorting can be utilized. One of the selection or sorting procedures can involve isolating binders that bind to protein L or an antibody to a polypeptide tag such as antibody to the gD protein or polyhistidine tag.

In some cases, suitable host cells are infected with the binders and helper phage, and the host cells are cultured under conditions suitable for amplification of the phagemid particles. The phagemid particles are then collected and the selection process is repeated one or more times until binders having the desired affinity for the target molecule are selected. Preferably at least 2 rounds of selection are conducted.

After binders are identified by binding to the target antigen, the nucleic acid can be extracted. Extracted DNA can then be used directly to transform *E. coli* host cells or alternatively, the encoding sequences can be amplified, for example using PCR with suitable primers, and then inserted into a vector for expression.

A preferred strategy to isolate high affinity binders is to bind a population of phage to an affinity matrix which contains a low amount of ligand. Phage displaying high affinity polypeptide is preferentially bound and low affinity polypeptide is washed away. The high affinity polypeptide is then recovered by elution with the ligand or by other procedures which elute the phage from the affinity matrix.

Preferably, the process of screening is carried out by automated systems to allow for high-throughput screening of library candidates.

In some embodiments, libraries comprising polypeptides of the invention are subjected to a plurality of sorting rounds, wherein each sorting round comprises contacting the binders obtained from the previous round with a target molecule distinct from the target molecule(s) of the previous round(s). Preferably, but not necessarily, the target molecules are homologous in sequence, for example members of a family of related but distinct polypeptides, such as, but not limited to, cytokines (for example, alpha interferon subtypes).

In the preferred embodiment of the invention the antigen, or a fragment thereof is coated on microtiter plates and binding thereto is assessed, e.g. by phage ELISA as in the example below.

One or more rounds of selection may be carried out. Significant enrichment may be observed by the second, third or subsequent round of selection, and random clones may be selected from the first, second, third, fourth and/or subsequent rounds of panning and analyzed by phage ELISA and DNA sequence analysis.

The altered antibodies will have mutation(s) in one or more hypervariable regions thereof. In the examples herein, for the anti-IgE and anti-LFA-1 libraries, mutations were almost exclusively located in H1 and L2, respectively, while mutations in the anti-TF library were limited to one of the three hypervariable regions in the VL domain. Without being bound to any one theory, this indicates that these locations are the regions where solutions to a poor fit of the murine hypervariable regions on the human framework can be found.

The mutations may occur at position 34 and/or 35 of H1. Moreover, the mutated hypervariable region residue(s) may be buried and/or may interact with the framework according to the structure of the humanized antibody. Alternatively, or additionally, the mutated hypervariable region residue(s) may be centrally located near the surface of the VH domain so that they may also potentially affect the structural conformations of one or more other hypervariable regions, e.g. with H2 and/or H3.

Following production of the altered antibody, the activity of that molecule relative to the parent antibody may be determined. As noted above, this may involve determining the binding affinity and/or other biological activities of the antibody. In a preferred embodiment of the invention, a panel of antibody variants are prepared and are screened for binding affinity for the antigen and/or potency in one or more biological activity assays. The affinities achieved are preferably similar to, e.g. no less than 100 fold, or no less than 10 fold the affinity of the non-human parent antibody. For example, the antibody variant of interest may bind the antigen of interest with a binding affinity ($K_d$) value of no more than about $5 \times 10^{-7}$ M, more preferably no more than about $5 \times 10^{-8}$ M and, optionally, no more than about $5 \times 10^{-9}$ M. Generally, the binding affinity of the antibody variant of interest will, like the parent antibody, be in the nanomolar or better range.

One or more of the antibody variants selected from an initial screen are optionally subjected to one or more further biological activity assays to confirm that the antibody variant(s) have improved activity in more than one assay.

Techniques for producing antibodies, which may be the non-human or parent antibody and therefore require modification according to the techniques elaborated herein, follow:

B. Antibody Preparation (i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., *Nature,* 348: 552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA,* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Human Antibodies

Transgenic animals (e.g., mice) that are capable, upon immunization, of producing a full repertoire of human antibodies in the absence of endogenous immunoglobulin production are available in the art. For example, it has been described that the homozygous deletion of the antibody heavy-chain joining region ($J_H$) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and Duchosal et al. *Nature* 355:258 (1992).

Human antibodies can also be derived from phage-display libraries (Hoogenboom et al., *J. Mol. Biol.,* 227:381 (1991); Marks et al., *J. Mol. Biol.,* 222:581-597 (1991); Vaughan et al. *Nature Biotech* 14:309 (1996)).

(iv) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229: 81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(v) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); .BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)).

Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vi) Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. An especially preferred variant has amino acid substitutions at positions 298, 333 and 334 of the Fc region, and improved ADCC function.

Antibodies with altered Clq binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof.

(vii) Conjugates and Other Modifications of the Altered Antibody

The antibody variant herein is optionally conjugated to a cytotoxic agent.

Chemotherapeutic agents useful in the generation of such antibody variant-cytotoxic agent conjugates have been described above.

Conjugates of an antibody variant and one or more small molecule toxins, such as a calicheamicin, a maytansine (U.S. Pat. No. 5,208,020), a trichothene, and CC1065 are also contemplated herein. In one embodiment of the invention, the antibody variant is conjugated to one or more maytansine molecules (e.g. about 1 to about 10 maytansine molecules per antibody variant molecule). Maytansine may, for example, be converted to May-SS-Me which may be reduced to May-SH3 and reacted with modified antibody variant (Chari et al. *Cancer Research* 52: 127-131 (1992)) to generate a maytansinoid-antibody variant conjugate.

Alternatively, the antibody variant is conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al. *Cancer Research* 53: 3336-3342 (1993) and Lode et al. *Cancer Research* 58: 2925-2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates antibody variant conjugated with a compound with nucleolytic activity (e.g. a ribonuclease or a DNA endonuclease such as a deoxyribonuclease; DNase).

A variety of radioactive isotopes are available for the production of radioconjugated antibody variants. Examples include At$^{211}$, I$^{131}$, I$^{125}$, Y$^{90}$, Re$^{186}$, Re$^{188}$, Sm$^{153}$, Bi$^{212}$, P$^{32}$ and radioactive isotopes of Lu.

Conjugates of the antibody variant and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-l-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody variant. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody variant and cytotoxic agent may be made, e.g. by recombinant techniques or peptide synthesis.

The antibody variants of the present invention may also be conjugated with a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. The enzyme component of such conjugates includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody variant-abzyme conjugates can be prepared as described herein for delivery of the abzyme to a tumor cell population. The enzymes of this invention can be covalently bound to the antibody variant by techniques well known in the art such as the use of the heterobifunctional crosslinking reagents discussed above.

Alternatively, fusion proteins comprising at least the antigen binding region of an antibody variant of the invention linked to at least a functionally active portion of an enzyme of the invention can be constructed using recombinant DNA techniques well known in the art (see, e.g., Neuberger et al., *Nature*, 312: 604-608 (1984)).

Other modifications of the antibody variant are contemplated herein. For example, the antibody variant may be linked to one of a variety of nonproteinaceous polymers, e.g., polyethylene glycol (PEG), polypropylene glycol, polyoxyalkylenes, or copolymers of polyethylene glycol and polypropylene glycol. Antibody fragments, such as Fab', linked to one or more PEG molecules are an especially preferred embodiment of the invention.

The antibody variants disclosed herein may also be formulated as liposomes. Liposomes containing the antibody variant are prepared by methods known in the art, such as described in Epstein et al., *Proc. Natl. Acad. Sci. USA*, 82:3688 (1985); Hwang et al., *Proc. Natl Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Patent No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.*81(19)1484 (1989).

To increase the serum half life of the antagonist, one may incorporate a salvage receptor binding epitope into the antagonist (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO00/42072 (Presta, L.).

Engineered antibodies with three or more (preferably four) functional antigen binding sites are also contemplated (US Appln No. US2002/0004587 A1, Miller et al.).

(viii) Glycosylation Variants

Another type of amino acid variant of the antagonist alters the original glycosylation pattern of the antagonist. Such altering includes deleting one or more carbohydrate moieties found in the antagonist, and/or adding one or more glycosylation sites that are not present in the antagonist.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antagonist is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antagonist (for O-linked glycosylation sites).

Where the antibody comprises an Fc region, the carbohydrate attached thereto may be altered. For example, antibodies with a mature carbohydrate structure which lacks fucose attached to an Fc region of the antibody are described in US Pat Appl No US 2003/0157108 A1, Presta, L. Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

C. Pharmaceutical Formulations

Therapeutic formulations of the antibody variant are prepared for storage by mixing the antibody variant having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody variant, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-Therapeutic Uses for the Antibody Variant

The antibody variants of the invention may be used as affinity purification agents. In this process, the antibodies are immobilized on a solid phase such a Sephadex resin or filter paper, using methods well known in the art. The immobilized antibody variant is contacted with a sample containing the antigen to be purified, and thereafter the support is washed with a suitable solvent that will remove substantially all the material in the sample except the antigen to be purified, which is bound to the immobilized antibody variant. Finally, the support is washed with another suitable solvent, such as glycine buffer, pH 5.0, that will release the antigen from the antibody variant.

The variant antibodies may also be useful in diagnostic assays, e.g., for detecting expression of an antigen of interest in specific cells, tissues, or serum.

For diagnostic applications, the antibody variant typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody variant can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g.,orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) beta-D-galactosidase (beta-D-Gal) with a chromogenic substrate (e.g., p-nitrophenyl-beta-D-galactosidase) or fluorogenic substrate 4-methylumbelliferyl-beta-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody variant. The skilled artisan will be aware of various techniques for achieving this. For example, the antibody variant can be conjugated with biotin and any of the three broad categories of labels mentioned above can be conjugated with avidin, or vice versa. Biotin binds selectively to avidin and thus, the label can be conjugated with the antibody variant in this indirect manner. Alternatively, to achieve indirect conjugation of the label with the antibody variant, the antibody variant is conjugated with a small hapten (e.g., digoxin) and one of the different types of labels mentioned above is conjugated with an anti-hapten antibody variant (e.g., anti-digoxin antibody). Thus, indirect conjugation of the label with the antibody variant can be achieved.

In another embodiment of the invention, the antibody variant need not be labeled, and the presence thereof can be detected using a labeled antibody which binds to the antibody variant.

The antibodies of the present invention may be employed in any known assay method, such as competitive binding assays, direct and indirect sandwich assays, and immunoprecipitation assays. Zola, *Monoclonal Antibodies: A Manual of Techniques,* pp. 147-158 (CRC Press, Inc. 1987).

Competitive binding assays rely on the ability of a labeled standard to compete with the test sample analyze for binding with a limited amount of antibody variant. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyze is bound by a first antibody which is immobilized on a solid support, and thereafter a second antibody binds to the analyze, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example. The antibodies may also be used for in vivo diagnostic assays. Generally, the antibody variant is labeled with a radionuclide (such as $^{111}$In, $^{99}$Tc, $^{14}$C, $^{131}$I, $^{125}$I, $^{3}_{H,}$ $^{32}$P or $^{35}$S) so that the tumor can be localized using immunoscintigraphy.

E. Diagnostic Kits

As a matter of convenience, the antibody variant of the present invention can be provided in a kit, i.e., a packaged combination of reagents in predetermined amounts with instructions for performing the diagnostic assay. Where the antibody variant is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. In Vivo Uses for the Antibody Variant

For therapeutic applications, the antibody variants of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The antibodies also are suitably administered by intra-tumoral, peri-tumoral, intra-lesional, or peri-lesional routes, to exert local as well as systemic therapeutic effects. In addition, the antibody variant is suitably administered by pulse infusion, particularly with declining doses of the antibody variant. Preferably the dosing is given by injections, most preferably intravenous or subcutaneous injections, depending in part on whether the administration is brief or chronic.

With respect to the exemplified antibodies, IgE antibodies may be used to treat IgE-mediated disorders (see definitions above), including allergic asthma. LFA-1 or CD11a antibodies may be used to treat LFA-1 mediated disorders or autoimmune diseases including those listed above in the definitions section, but especially psoriasis, psoriatic arthritis, atopic dermatitis, multiple sclerosis, Crohn's disease, lupus, ankylosing spondylitis, organ transplant and rheumatoid arthritis. Tissue factor (TF) antibodies can be used to block binding of TF to Factor VII and/or Factor X. TF antibodies may treat hypercoagulable states, cancer, and inflammatory diseases, including the specific indications encompassed by these diseases or disorders as listed in the definitions section above.

For the prevention or treatment of disease, the appropriate dosage of antibody variant will depend on the type of disease to be treated, the severity and course of the disease, whether the antibody variant is administered for preventive or therapeutic purposes, previous therapy, the patient's clinical history and response to the antibody variant, and the discretion of the attending physician. The antibody variant is suitably administered to the patient at one time or over a series of treatments.

Depending on the type and severity of the disease, about 1 ug/kg to 15 mg/kg (e.g., 0.1-20mg/kg) of antibody variant is an initial candidate dosage for administration to the patient, whether, for example, by one or more separate administrations, or by continuous infusion. A typical daily dosage might range from about 1 ug/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody variant composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The "therapeutically effective amount" of the antibody variant to be administered will be governed by such considerations, and is the minimum amount necessary to prevent, ameliorate, or treat a disease or disorder. The antibody variant need not be, but is optionally formulated with one or more agents currently used to prevent or treat the disorder in question. The effective amount of such other agents depends on the amount of antibody variant present in the formulation, the type of disorder or treatment, and other factors discussed above. These are generally used in the same dosages and with administration routes as used hereinbefore or about from 1 to 99% of the heretofore employed dosages.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody variant. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLES

The examples herein demonstrate the applicability of the method of CDR-repairing for antibodies directed against three different antigens, namely tissue factor (TF), immunoglobulin E (IgE), and CD11a.

Materials and Methods

Residue numbers are according to Kabat (Kabat et al., *Sequences of proteins of immunological interest*, 5th Ed., Public Health Service, National Institutes of Health, Bethesda, Md. (1991)). Single letter amino acid abbreviations are used. DNA degeneracies are represented using the IUB code (N=A/C/G/T, D 32 A/G/T, V=A/C/G, B=C/G/T, H=A/C/T, K=G/T, M=A/C, R=A/G, S=G/C, W=A/T, Y=C/T).

Direct hypervariable region grafts onto the acceptor human consensus framework—The phagemid used for this work is a monovalent Fab-g3 display vector and consists of 2 open reading frames under control of the phoA promoter. The first open reading frame consists of the stII signal sequence fused to the acceptor light chain and the second consists of the stII signal sequence fused to the VH and CH1 domains of acceptor followed by the minor phage coat protein P3.

The VL and VH domains from murine antibodies to be humanized were aligned with the human consensus VL domain and the acceptor VH domain. The acceptor VH framework differs from the human consensus VH domain at 3 positions: R71A, N73T, and L78A (Carter et al., *Proc. Natl. Acad. Sci. USA* 89:4285 (1992)). Hypervariable regions from the murine antibody were engineered into the acceptor human consensus framework to generate a direct-graft of the murine antibody. In the VL domain the following regions were grafted to the human consensus acceptor: positions 24-34 (L1), 50-56 (L2) and 89-97 (L3). In the VH domain, positions 26-35 (H1), 49-65 (H2) and 93-102 (H3) were grafted (FIGS. 1A-1B).

The direct-graft variants were generated by Kunkel mutagenesis using a separate oligonucleotide for each hypervariable region. Correct clones were assessed by DNA sequencing.

Soft randomization of the hypervariable regions—Sequence diversity was introduced into each hypervariable region using a soft randomization strategy that maintains a bias towards the murine hypervariable region sequence. This was accomplished using a poisoned oligonucleotide synthesis strategy first described by Gallop et al., *J. Med. Chem.* 37:1233-1251 (1994). For a given position within a hypervariable region to be mutated, the codon encoding the wild-type amino acid is poisoned with a 70-10-10-10 mixture of nucleotides resulting in an average 50 percent mutation rate at each position.

Soft randomized oligonucleotides were patterned after the murine hypervariable region sequences and encompassed the same regions defined by the direct hypervariable region grafts. Only two positions, amino acids at the beginning of H2 and H3 in the VH domain, were limited in their diversity. The codon RGC was used for position 49 encoding A, G, S or T and at position 94, the codon ARA was used encoding R or K.

Generation of phage libraries—Randomized oligonucleotide pools designed for each hypervariable region were phosphorylated separately in six 20 µl reactions containing 660 ng of oligonucleotide, 50 mM Tris pH 7.5, 10 mM $MgCl_2$, 1 M ATP, 20 mM DTT, and 5 U polynucleotide kinase for 1 h at 37° C. The six phosphorylated oligonucleotide pools were then combined with 20µg of Kunkel template in 50 mM Tris pH 7.5, 10 mM $MgCl_2$ in a final volume of 500 µl resulting in a oligonucleotide to template ratio of 3. The mixture was annealed at 90° C. for 4 min, 50° C. for 5 min and then cooled on ice. Excess, unannealed oligonucleotide was removed with a QIAquick® PCR purification kit (Qiagen kit 28106) using a modified protocol to prevent excessive denaturation of the annealed DNA. To the 500 µl of annealed mixture, 150 µl of PB was added, and the mixture was split between 2 silica columns. Following a wash of each column with 750 µl of PE and an extra spin to dry the columns, each column was eluted with 110 µl of 10 mM Tris, 1 mM EDTA, pH 8. The annealed and cleaned-up template (220 µl) was then filled in by adding 1 µl 100 mM ATP, 10 µl 25 mM dNTPs (25 mM each of dATP, dCTP, dGTP and dTTP), 15 µl 100 mM DTT, 25 µl 10× 198 buffer (0.5 M Tris pH 7.5, 0.1 M $MgCl_2$), 2400 U T4 ligase, and 30 U T7 polymerase for 3 h at room temperature.

The filled in product was analyzed on Tris-Acetate-EDTA/agarose gels (Sidhu et al., *Methods in Enzymology* 328:333-363 (2000)). Three bands are usually visible: the bottom band is correctly filled and ligated product, the middle band is filled but unligated and the top band is strand displaced. The top band is produced by an intrinsic side activity of T7 polymerase and is difficult to avoid (Lechner et al., *J. Biol. Chem.* 258:11174-11184 (1983)); however, this band transforms 30-fold less efficiently than the top band and usually contributes little to the library. The middle band is due to the absence of a 5' phosphate for the final ligation reaction; this band transforms efficiently and unfortunately, gives mainly wild type sequence.

The filled in product was then cleaned-up and electroporated into SS320 cells and propagated in the presence of M13/K07 helper phage as described by Sidhu et al., *Methods in Enzymology* 328:333-363 (2000). Library sizes ranged from $1\text{-}2\times10^9$ independent clones. Random clones from the initial libraries were sequenced to assess library quality.

Phage Selection—Human LFA-1, IgE or TF were coated on MaxiSorp® microtiter plates (Nunc) at 5 µg/ml in PBS. For the first round of selection 8 wells of target were used; a single well of target was used for successive rounds of selection. Wells were blocked for 1 h using Casein Blocker (Pierce). Phage were harvested from the culture supernatant and suspended in PBS containing 1% BSA and 0.05% of the nonionic detergent TWEEN 20® (PBSBT). After binding to the wells for 2 h, unbound phage were removed by extensive washing with PBS containing 0.05% of the nonionic detergent TWEEN® 20 (PBST). Bound phage were eluted by incubating the wells with 50 mM HC1, 0.5 M KCl for 30 min. Phage were amplified using Top10 cells and M13/KO7 helper phage and grown overnight at 37° C. in 2YT, 50µg/ml carbanacillin. The titers of phage eluted from a target coated well were compared to titers of phage recovered from a non-target coated well to assess enrichment.

Phage ELISA—MaxiSorp® microtiter plates were coated with human LFA-1, IgE or TF at 5 µg/ml in PBS over night and then blocked with Casein Blocker. Phage from culture supernatants were incubated with serially diluted LFA-1, IgE or TF in PBSBT in a tissue culture microtiter plate for 1 h after which 80 µl of the mixture was transferred to the target coated wells for 15 min to capture unbound phage. The plate was washed with PBST and HRP conjugated anti-M13 (Amersham Pharmacia Biotech) was added (1:5000 in PBSBT) for 40 min. The plate was washed with PBST and developed by adding Tetramethylbenzidine substrate (Kirkegaard and Perry Laboratories, Gaithersburg, MD). The absorbance at 405 nm was plotted as a function of target concentration in solution to determine an $IC_{50}$. This was used as an affinity estimate for the Fab clone displayed on the surface of the phage.

Results

Generation of Large Phage Libraries Using Multiple Oligonucleotides

The potential sequence diversity encompassed in a strategy to completely randomize over 60 positions represented by the 6 hypervariable regions of an antibody is huge, far beyond the capacity of any library screening method. Further, complete randomization of the hypervariable regions would likely result in a change of the antigen epitope recognized by the antibody. To solve both of these problems a soft randomization strategy was used that maintained a bias towards the murine hypervariable region sequence while introducing a 50 percent mutation rate at each selected position.

Large phage display libraries have been generated using the method described by Sidhu (Sidhu et al., *Methods in Enzymology* 328:333-363 (2000)). Unfortunately as the number of oligonucleotides in a Kunkel mutagenesis reaction increases the frequency of clones containing all mutagenic oligonucleotides decreases. To compensate for this, one could increase the oligonucleotide concentration to ensure that all sites are fully occupied during the annealing process; however, as the concentration of oligonucleotides in the polymerase reaction increases, the potential for side reactions also increases resulting in a decreased yield of mutagenized clones and an overall reduced library size.

This problem was overcome by adding a clean-up step to remove excess un-annealed oligonucleotides prior to the polymerase reaction. The QIAquick® PCR purification kit is designed to remove single stranded DNA of less than 100 base pairs. A reagent, PB, is added to facilitate double stranded DNA binding to the silica matrix. While single stranded Kunkel template DNA would be expected to bind to the silica in the presence of reagent, high concentrations of reagent had the potential to dislodge bound oligonucleotides that were annealed to the template. In order to determine the minimum amount of reagent required for template binding to the silica column, the binding of DNA to the silica column was followed as a function of the reagent (PB) concentration provided in the purification kit (FIG. 2). As expected, in the presence of PB, an 81 base pair oligonucleotide did not interact with the silica column. The fraction of double stranded phagemid DNA that bound to the silica increased at higher concentrations of PB; however, only a quarter volume of PB was sufficient to attain significant binding of single stranded uracil template. Next, the effects of cleaning up annealed template with this method on retention of annealed oligonucleotides and yield of mutagenized clones was explored.

Analysis of Initial Libraries

Fab phage display libraries were generated starting with 20 µg of uracil template and annealed with a 3-fold molar excess each of 6 oligonucleotides followed by removal of un-annealed excess oligonucleotide prior to the polymerase reaction. Analysis of the polymerase reaction on a TAE/agarose gel revealed a significant reduction in side reaction products relative to a reaction that did not utilize the PCR purification clean-up step. The library size for the mutagenesis reaction utilizing the clean up step was $3.5\times10^9$ cfu, at least 100-fold larger than the yield of clones obtained without this step. DNA sequence analysis of unselected clones obtained from libraries generated with the clean-up step is shown in FIGS. 3A-1, 3A-2, 3B-1, 3B-2, 3C-1 and 3C-2. About 15 percent of the clones have all six hypervariable regions replaced; remaining clones were missing various combinations of hypervariable region replacements.

In order to maximize the potential library size, the direct-murine hypervariable region graft onto the templateconsensus framework was used as a template for the mutagenesis reaction. Therefore, if any combination of hypervariable regions were not replaced during the mutagenesis reaction, at least the wild-type murine hypervariable region would be present, thus leading to a potentially useful clone. Random sequences taken from an initial unselected library designed for humanization of the murine monoclonal antibody Maell are shown in FIGS. 3A-1, 3A-2, 3B-1, 3B-2, 3C-1 and 3C-2. While not all of the hypervariable regions have been replaced, the ones that are mutated reflect a clear murine hypervariable region sequence bias stemming from the soft randomization design of the library.

Affinity of Selected Clones

Fab phage display libraries based on the murine monoclonal antibodies Maell (anti-IgE), D3 (anti-TF) and MHM24 (anti-CD11α), were panned against immobilized IgE, TF and LFA-1, respectively. Significant enrichment was observed by the third round of selection. Random clones were selected from the third and fourth rounds of panning and analyzed by phage ELISA and DNA sequence analysis (FIGS. 4A-4B). The affinity of the clones generally ranged from 2 to 20 nM with many of the clones falling into the single digit nanomolar range regardless of the library and target. Although this is just an approximation of their true affinity, this places them in the affinity range of the original murine Fab or chimeric Fab affinity (D3=14 nM, Mae11=3.5 nM and MHM24=reported as IgG est. 0.1 nM) (Presta et al., *J. Immunol.* 151, 2623-2632 (1993); Werther et al., *J. Immunol. Methods* 157:4986-4995 (1996); and Presta et al., *Thromb. Haemost.* 85:379-389 (2001)).

Sequence Analysis of Selected Clones

Most surprising was the limited and highly concentrated mutations located in the hypervariable regions of the affinity selected clones (FIGS. 4A-4B). For the anti-IgE and anti-LFA-1 libraries, mutations were almost exclusively located in H1 and L2, respectively, while mutations in the anti-TF library were limited to one of the 3 hypervariable regions in the VL domain. This clustering suggests that these locations are the regions where solutions to a poor fit of the murine hypervariable regions on the human framework can be found. Particularly interesting is the fact that the mutations suggest a consensus solution for improving affinity.

For clones selected for binding to IgE, the changes S34K and W35L in CDR-H1 of the VH domain appear to be all that is needed to restore the affinity of the Mae11-based hypervariable region graft to that of the original murine monoclonal antibody. These residues are buried and interact with the framework according to the Fab structure of the humanized antibody. They are centrally located near the surface of the VH domain so that they may also potentially affect the structural conformations of H2 and H3. By comparison, humanization by the traditional method involved 12 changes scattered throughout the VL and VH domains (Presta et al., *J. Immunol.* 151, 2623-2632 (1993)).

Affinity of Templates Resulting from the Direct Murine Hypervariable Region Graft When initially humanizing D3, Mae11 and MHM24, no detectible binding was observed for the direct murine hypervariable region grafts into the human consensus framework that was used (Presta et al., *J. Immunol.* 151, 2623-2632 (1993); Werther et al., *J. Immunol. Methods* 157:4986-4995 (1996); and Presta et al., *Thromb. Haemost.* 85:379-389 (2001)). Unexpectedly, when the direct murine hypervariable region grafts were made for these antibodies using the acceptor consensus framework (which differs at 3 positions in VH: R71A, N73T, and A78L), binding was observed for the D3 and MHM24 grafts. By phage ELISA the direct grafts had IC50s of 20 and 6 nM respectively. Although most of the selected clones have slightly improved affinities, the presence of un-mutated, directly grafted hypervariable regions (i.e. template background) in these 2 libraries is explained by the initial affinity of the templates.

Importantly, the directly grafted Mae11 template had no measurable affinity for IgE. Thus the few changes made to H1 in these clones demonstrate the potential of restoring antigen binding affinity to directly grafted murine hypervariable regions on a new acceptor without requiring the change of any framework residues. This would suggest that this methodology could be applied to any framework acceptor.

Discussion

Previous efforts to transfer the antigen binding information of murine monoclonal antibodies onto a human acceptor have relied on the introduction of changes within the framework to correct and re-establish proper hypervariable region-antigen interactions. Rather than remodeling the hypervariable region-framework interface by altering framework residues, the examples herein demonstrate that modified hypervariable regions can be selected to correct framework deficiencies while still maintaining antigen interactions.

Phage display of antibody libraries designed to maintain a sequence bias towards the direct hypervariable region-grafted antibody are capable of identifying regions where proper framework-hypervariable region-antigen interactions are disrupted. Although the potential sequence diversity of the library is vastly under represented, potential solutions that can re-establish a beneficial framework-hypervariable region fit are offered. From the Fab sequences that were selected for binding to IgE, it appears that the disruption caused by a single poorly grafted hypervariable region was sufficient to completely disrupt antigen binding (FIGS. 4A-4B). It is surprising that by changing 2 residues in H1 of the VH domain, a change observed in 11 independent clones, high affinity binding can be restored. These residues reside near and interact with the VH domain framework and potentially influence the conformations of H1, H2 and H3.

The fact that the initial library was limited in size may explain why observed changes were targeted to a single hypervariable region, since the probability of selecting 2 independent changes simultaneously would be quite rare. Although additional improvements could potentially be gained by the generation of subsequent libraries targeting the remaining hypervariable regions, the fact that high affinity clones were selected by this method suggests that most hypervariable region-framework interactions are tolerated and that the identification and alteration of a single offending hypervariable region can lead to restored antigen binding.

Obviously since no changes were made to the framework, the sequence described for final humanized antibody (F(ab)-12, E25) reported by Presta et al. and that of these selected clones is vastly different (Presta et al., *J. Immunol.* 151, 2623-2632 (1993)). In addition, the selected clones in FIGS. 4A-4B do not incorporate any of the hypervariable region changes made during the traditional humanization process. Thus both humanization methods, despite producing antibodies with similar affinities for antigen result in variants with vastly different sequences. This demonstrates the malleability of the antibody surface and the ability to offer multiple binding solutions to the same problem.

Although the few framework changes that have been incorporated into human therapeutics have not resulted in any known immunological reactions, the absence of these changes would intuitively seem beneficial. Further, the approach taken here demonstrates changes to the framework are not necessary and through the use of antibody phage selection, variants with restored antigen binding can be rapidly identified.

What is claimed is:

1. A method of making an altered antibody comprising a heavy chain variable domain (VH) and a light chain variable domain (VL) comprising a first step of incorporating six non-human hypervariable regions (HVR-H1, HVR-H2, HVR-H3, HVR-L1, HVR-L2, and HVR-L3) obtained from a non-human parent antibody into VH and VL acceptor human frameworks, respectively, thereby making a direct hypervariable region-grafted antibody, wherein the direct hypervariable region-grafted antibody has an antigen binding affinity less than the parent antibody, and comprising a further step of randomizing one or more amino acids in one or more of the non-human hypervariable regions wherein the one or more amino acids maintain a sequence bias towards the sequence of the incorporated non-human hypervariable region and wherein the randomizing step comprises the codon RGC for position 49 of HVR-H2 and the codon ARA for position 94 of HVR -H3, wherein the numbering is according to Kabat, without modifying the VH or VL acceptor human framework sequence, and selecting an altered antibody with restored or improved binding affinity ($K_d$) compared to the parent antibody, and wherein the restored or improved binding affinity has a value of no more than about $5 \times 10^{-7}$ M.

2. The method of claim 1 wherein the altered antibody is displayed on a phage or phagemid.

3. The method of claim 2 wherein the phage or phagemid is in a library.

4. The method of claim 3 comprising introducing an approximately 10-50 percent mutation rate into a nucleic acid encoding each randomized amino acid.

5. The method of claim 4 wherein a codon encoding the amino acid to be mutated is contaminated with a mixture of other nucleotides.

6. The method of claim 5 wherein the mixture of other nucleotides is a 70-10-10-10 mixture.

7. A method of selecting an altered antibody comprising:

(a) preparing nucleic acid encoding at least the variable heavy (VH) and variable light (VL) domains of a direct hypervariable region-grafted antibody, each comprising VH and VL acceptor human frameworks and six hypervariable regions of a non-human antibody (HVR-H1, HVR-H2, HVR-H3, HVR-L1, HVR-L2, and HVR-L3, respectively), wherein the non-human antibody is a parent antibody;

(b) substituting hypervariable region residues by introducing an approximately 10-50 percent mutation rate into the nucleic acid so as to maintain a bias towards the non-human hypervariable region sequences region and comprising substituting the codon RGC for position 49 of HVR -H2 and the codon ARA for position 94 of HVR-H3, wherein the numbering is according to Kabat; and (c) selecting one or more altered antibodies that bind antigen with restored or improved binding affinity compared to the parent antibody.

8. The method of claim 7 wherein the altered antibodies are displayed on phage or phagemid.

* * * * *